US006461617B1

(12) United States Patent
Shone et al.

(10) Patent No.: US 6,461,617 B1
(45) Date of Patent: Oct. 8, 2002

(54) RECOMBINANT TOXIN FRAGMENTS

(75) Inventors: Clifford Charles Shone; Conrad Padraig Quinn, both of Wiltshire; Keith Alan Foster, Surrey, all of (GB)

(73) Assignees: Microbiological Research Authority, Salisbury (GB); The Speywood Laboratory Limited, London (GB)

( * ) Notice: Subject to any disclaimer, the term of this patent is extended or adjusted under 35 U.S.C. 154(b) by 0 days.

(21) Appl. No.: 09/255,829

(22) Filed: Feb. 23, 1999

Related U.S. Application Data

(63) Continuation of application No. PCT/GB97/02273, filed on Aug. 22, 1997, which is a continuation-in-part of application No. 08/782,893, filed on Dec. 27, 1996, now abandoned.

(30) Foreign Application Priority Data

Aug. 23, 1996 (GB) ............................................ 9617671
Dec. 13, 1996 (GB) ............................................ 9625996

(51) Int. Cl.$^7$ ........................ A61K 39/02; A61K 39/38; A61K 39/00; C12P 21/06; C12P 21/04
(52) U.S. Cl. ............................. 424/236.1; 424/157.1; 424/164.1; 424/167.1; 424/178.1; 424/179.1; 424/184.1; 424/235.1; 424/234.1; 424/236.1; 424/239.1; 424/247.1; 530/300; 530/350; 530/825; 435/69.1; 435/70.1; 435/71.1; 435/71.2; 435/69.7; 435/252.33; 536/23.4; 536/23.7
(58) Field of Search ........................... 424/236.1, 235.1, 424/234.1, 184.1, 237.1, 247.1, 183.1, 178.1, 179.1; 530/300, 350, 825; 426/167.1, 164.1, 157.1; 435/69.1, 70.1, 71.1, 71.2, 69.7, 252.35, 320.11; 536/23.7, 23.4

(56) References Cited

U.S. PATENT DOCUMENTS

| 4,594,336 A | * | 6/1986 | Bizzini |  |
| 5,919,665 A |  | 7/1999 | Williams | .................... 435/71.1 |
| 6,043,042 A |  | 3/2000 | Shone et al. | .................. 435/7.1 |

FOREIGN PATENT DOCUMENTS

| WO | WO 94/21300 |  | 9/1994 |
| WO | WO 94/21684 |  | 9/1994 |
| WO | WO96/2802 | * | 5/1996 |
| WO | WO 96/12802 |  | 5/1996 |
| WO | WO 96/33273 |  | 10/1996 |
| WO | WO 98/08540 |  | 3/1998 |

OTHER PUBLICATIONS

Rudinger et al ; Characteristics of the amino acids as components of a peptide hormone sequence; Peptide Hormones ; Edited byu Parsons ; University Park Press; Baltimore, 1976.*

Poulain et al, Inhibition of transmitter release by botulinum neurotoxin A, European Journal of Biochemistry, vol. 185, pp. 197–203, 1989.*

Niemann, H., "Molecular Biology of Clostridial Neurotoxins," In *Sourcebook of Bacterial Protein Toxins*, Ch. 15, Alouf, J.E. and Freer, J.H., editors, Academic Press Limited, London, pp. 303–348 (1991).

Poulain, B. et al., "Inhibition of transmitter release by botulinum neurotoxin A: Contribution of various fragments to the intoxication process," *J. Biochem.* 185:197–203 (1989).

Binz, T., et al., "The Complete Sequence of Botulinum Neurotoxin Type A and Comparison with Other Clostridial Neurotoxins," *J. Biol. Chem.* 265:9153–9158 (Jun. 1990).

Kurazono, H., et al., "Minimal Essential Domains Specifying Toxicity of the Light Chains of Tetanus Toxin and Botulinum Neurotoxin Type A," *J. Biol. Chem.* 267:14721–14729 (Jul. 1992).

Li et al., "A Single Mutation in the Recombinant Light Chain of Tetanus Toxin Abolishes its Proteolytic Activity and Removes the Toxicity Seen after Reconstitution with Native Heavy Chain," *Biochem.* 33:7014–7020 (Jun. 1994).

International Search Report of International Application No. PCT/GB97/02273, mailed Jan. 30, 1998.

Bizzini, B., "Investigation of the Mode of Action of Tetanus Toxin with the Aid of Hybrid Molecules Consisting in Part of Tetanus Toxin–Derived Fragments," in *Bacterial Protein Toxins*, pp. 427–434, Academic Press London (1984).

* cited by examiner

*Primary Examiner*—Lynette R. F. Smith
*Assistant Examiner*—Padma Baskar
(74) *Attorney, Agent, or Firm*—Sterne, Kessler, Goldstein & Fox P.L.L.C.

(57) ABSTRACT

A polypeptide has first and second domains which enable the polypeptide to be translocated into a target cell or which increase the solubility of the polypeptide, or both, and further enable the polypeptide to cleave one or more vesicle or plasma-membrane associated proteins essential to exocytosis. The polypeptide thus combines useful properties of a clostridial toxin, such as a botulinum or tetanus toxin, without the toxicity associated with the natural molecule. The polypeptide can also contain a third domain that targets it to a specific cell, rendering the polypeptide useful in inhibition of exocytosis in target cells. Fusion proteins comprising the polypeptide, nucleic acids encoding the polypeptide and methods of making the polypeptide are also provided. Controlled activation of the polypeptide is possible and the polypeptide can be incorporated into vaccines and toxin assays.

10 Claims, 11 Drawing Sheets

M [Q] F V N K Q F N Y K D P V N G V D I A Y I K I P [N A] G Q M Q P V (Seq I.D. 2)
  1

23LH₄₂₃/A
(Q₂E, N₂₆K, A₂₇Y)

G S P G I H M T S R L Q K L L E F E L P
1

G T M [E F V N K Q F N Y K D P V N G V D I A Y I K I P K Y] G Q M Q P V (Seq I.D. 4)
   24

2LH₄₂₃/A
(Q₂E, N₂₆K, A₂₇Y)

G S M E F V N K Q F N Y K D P V N G V D I A Y I K I P K Y G Q M Q P V (Seq I.D. 6)
1 2 3

Native BoNT/A,
C. botulinum 2169
Thompson et al.1990

M [Q] F V N K Q F N Y K D P V N G V D I A Y I K I P N A G Q M Q P V
  1

Native BoNT/A,
C. botulinum 62A
Binz et al.1990

M [P] F V N K Q F N Y K D P V N G V D I A Y I K I P [N A] G Q M Q P V
  1

[____] = REGIONS OF NON-IDENTITY WITH THE NATIVE SEQUENCES.

FIG. 4

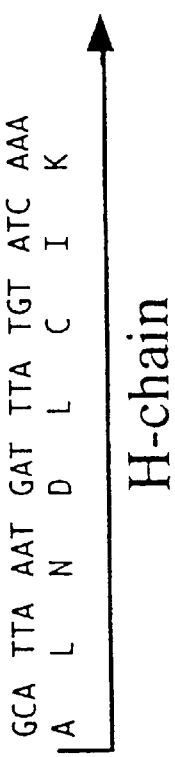
FIG. 5
FIG. 6

```
                                                                                    IGF-1
2587/863                                                                              ↑
TAC GTA GAT AAT CAA AGA TTA TCT ACA TTT ACT GAA TAT ATT AAG TCT AGG CCT GGA
 Y   V   D   N   Q   R   L   S   T   F   T   E   Y   I   K   S   R   P   G
2647/883                                              2677/893
CCG GAG ACG CTC TGC GGG GCT GAG CTG GTG GAT GCT CTT CAG TTC GTG TGT GGA GAC AGG
 P   E   T   L   C   G   A   E   L   V   D   A   L   Q   F   V   C   G   D   R
2707/903                                          2737/913
GGC TTT TAT TTC AAC AAG CCC ACA GGG TAT GGC TCC AGC AGT CGG AGG GCG CCT CAG ACA
 G   F   Y   F   N   K   P   T   G   Y   G   S   S   S   R   R   A   P   Q   T
2767/923                                      2797/933
GGT ATC GTG GAT GAG TGC TGC TTC CGG AGC TGT GAT CTA AGG AGG CTG GAG ATG TAT TGC
 G   I   V   D   E   C   C   F   R   S   C   D   L   R   R   L   E   M   Y   C
2827/943                                  2857/953
GCA CCC CTC AAG CCT GCC AAG TCA GCT GAA GCT TAG
 A   P   L   K   P   A   K   S   A   E   A  stop
```

FIG. 7

```
                                                                                    CtxA14
2587/863                                                                              ↑
TAC GTA GAT AAT CAA AGA TTA TCT ACA TTT ACT GAA TAT ATT AAG TCT AGG CCT CAA
 Y   V   D   N   Q   R   L   S   T   F   T   E   Y   I   K   S   R   P   Q
2647/883                                              2677/893
TCT AAA GTT AAA AGA CAA ATA TTT TCA GGC TAT CAA TCT GAT ATT GAT ACA CAT AAT AGA
 S   K   V   K   R   Q   I   F   S   G   Y   Q   S   D   I   D   T   H   N   R
2707/903
ATT AAG GAT GAA TTA TGA
 I   K   D   E   L  stop
```

FIG. 8

```
2587/863
TAC GTA GAT AAT CAA AGA TTA TTA TCT ACA GAA TAT ATT AAG TCA GGC CTG AAT
 Y   V   D   N   Q   R   L   L   S   T   E   Y   I   K   S   G   L   N
2647/883
TCC CCG GGT GCA GCT CAT TAT GCG CAA CAC TTT ACT GAA TAT ATT AAG TCA GGC CTG AAT
```
2617/873
```
                                             TTT ACT GAA TAT ATT AAG TCA GGC CTG AAT
                                              F   T   E   Y   I   K   S   G   L   N
2647/883
TCC CCG GGT GCA GCT CAT TAT GCG CAA CAC
 S   P   G   A   A   H   Y   A   Q   H
2677/893
                                        GAT GAA GCC GTA GAC AAC AAA TTC AAC AAA
                                         D   E   A   V   D   N   K   F   N   K
2707/903
GAA CAA CAA AAC GCG TTC TAT GAG ATC TTA CCT AAC TTA AAC GAA GAA CAA CGA GCA
 E   Q   Q   N   A   F   Y   E   I   L   P   N   L   N   E   E   Q   R   A
2737/913
2767/923
AAC GCC TTC ATC CAA AGT TTA AAA GAT GAC CAA AGC CAA AGC GCT AAC TTT AAC GCA
 N   A   F   I   Q   S   L   K   D   D   P   S   Q   S   A   N   F   N   A
2797/933
2827/943                                 2857/953
GCT AAA AAG CTA AAT GAT GCT CAG GCG CCG AAA GTA GAC AAC AAA TTC AAC GAA CAA
 A   K   K   L   N   D   A   Q   A   P   K   V   D   N   K   F   N   E   Q
2887/963                                 2917/973
CAA AAC GCG TTC TAT GAG ATC TTA CAT TTA CCT AAC TTA AAC GAA CAA CGA GAA GCA
 Q   N   A   F   Y   E   I   L   H   L   P   N   L   N   E   Q   R   E   A
2947/983                                 2977/993
TTC ATC CAA AGT TTA AAA GAT GAC CCA AGC CAA AGC GCT AAC CTT TTA GCA GAA GCT
 F   I   Q   S   L   K   D   D   P   S   Q   S   A   N   L   L   A   E   A
3007/1003                                3037/1013
AAG CTA AAT GAT GCT CAG GCG CCG AAA GTA GAC TAG
 K   L   N   D   A   Q   A   P   K   V   D    *
```

FIG. 9

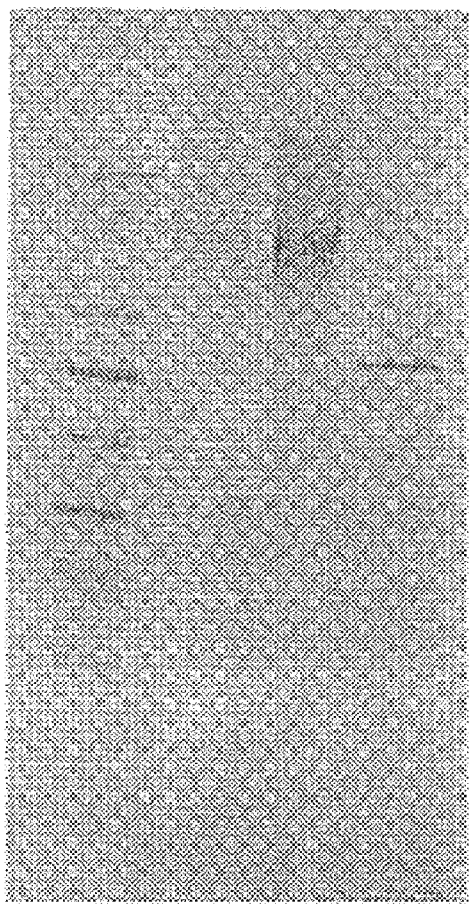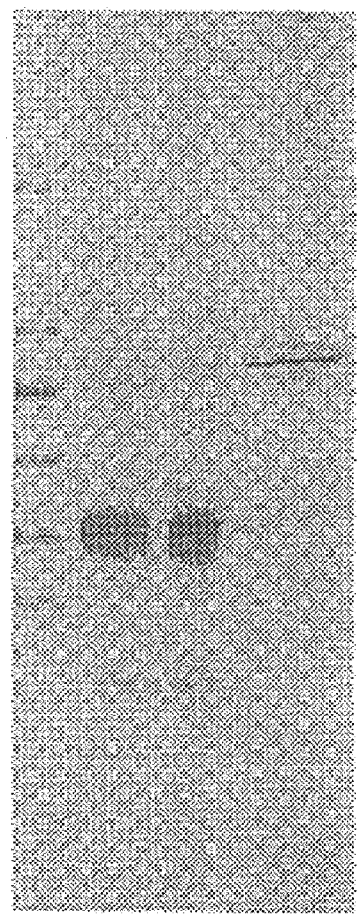
FIG. 13

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 2616 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION:1..2616

(xi) SEQUENCE DESCRIPTION: SEQ ID NO: 1:

```
ATG CAG TTC GTG AAC AAG CAG TTC AAC TAT AAG GAC CCT GTA AAC GGT      48
Met Gln Phe Val Asn Lys Gln Phe Asn Tyr Lys Asp Pro Val Asn Gly
 1               5                  10                  15

GTT GAC ATT GCC TAC ATC AAA ATT CCA AAC GCC GGC CAG ATG CAG CCG      96
Val Asp Ile Ala Tyr Ile Lys Ile Pro Asn Ala Gly Gln Met Gln Pro
                20                  25                  30

GTG AAG GCT TTC AAG ATT CAT AAC AAA ATC TGG GTT ATT CCG GAA CGC     144
Val Lys Ala Phe Lys Ile His Asn Lys Ile Trp Val Ile Pro Glu Arg
            35                  40                  45

GAT ACA TTT ACG AAC CCG GAA GAA GGA GAC TTG AAC CCG CCG CCG GAA     192
Asp Thr Phe Thr Asn Pro Glu Glu Gly Asp Leu Asn Pro Pro Pro Glu
        50                  55                  60

GCA AAG CAG GTG CCA GTT TCA TAC TAC GAT TCA ACC TAT CTG AGC ACA     240
Ala Lys Gln Val Pro Val Ser Tyr Tyr Asp Ser Thr Tyr Leu Ser Thr
    65                  70                  75                  80

GAC AAC GAG AAG GAT AAC TAC CTG AAG GGA GTG ACC AAA TTA TTC GAG     288
Asp Asn Glu Lys Asp Asn Tyr Leu Lys Gly Val Thr Lys Leu Phe Glu
                85                  90                  95
```

```
CGT ATT TAT TCC ACT GAC CTG GGC CGT ATG CTG CTG ACC TCA ATC GTC      336
Arg Ile Tyr Ser Thr Asp Leu Gly Arg Met Leu Leu Thr Ser Ile Val
            100                 105                 110

CGC GGA ATC CCA TTT TGG GGT GGC AGT ACC ATT GAC ACG GAG TTG AAG      384
Arg Gly Ile Pro Phe Trp Gly Gly Ser Thr Ile Asp Thr Glu Leu Lys
            115                 120                 125

GTT ATT GAC ACT AAC TGC ATT AAC GTG ATC CAA CCA GAC GGT AGC TAC      432
Val Ile Asp Thr Asn Cys Ile Asn Val Ile Gln Pro Asp Gly Ser Tyr
        130                 135                 140

AGA TCT GAA GAA CTT AAC CTC GTA ATC ATC GGG CCC TCC GCG GAC ATT      480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG      528
Ile Gln Phe Glu Cys Lys Ser Phe Gly His Glu Val Leu Asn Leu Thr
                165                 170                 175

CGT AAC GGT TAC GGC TCT ACT CAG TAC ATT CGT TTC AGC CCA GAC TTC      576
Arg Asn Gly Tyr Gly Ser Thr Gln Tyr Ile Arg Phe Ser Pro Asp Phe
            180                 185                 190

ACG TTC GGT TTC GAG GAG AGC CTG GAG GTT GAT ACC AAC CCG CTG TTG      624
Thr Phe Gly Phe Glu Glu Ser Leu Glu Val Asp Thr Asn Pro Leu Leu
            195                 200                 205

GGT GCA GGC AAG TTC GCA ACT GAT CCA GCG GTG ACC CTG GCA CAC GAG      672
Gly Ala Gly Lys Phe Ala Thr Asp Pro Ala Val Thr Leu Ala His Glu
        210                 215                 220

CTG ATC CAC GCC GGT CAT CGT CTG TAT GGC ATT GCG ATT AAC CCG AAC      720
Leu Ile His Ala Gly His Arg Leu Tyr Gly Ile Ala Ile Asn Pro Asn
225                 230                 235                 240

CGC GTG TTC AAG GTT AAC ACC AAC GCC TAC TAC GAG ATG AGT GGT TTA      768
Arg Val Phe Lys Val Asn Thr Asn Ala Tyr Tyr Glu Met Ser Gly Leu
                245                 250                 255

GAA GTA AGC TTC GAG GAA CTG CGC ACG TTC GGT GGC CAT GAT GCG AAG      816
Glu Val Ser Phe Glu Glu Leu Arg Thr Phe Gly Gly His Asp Ala Lys
            260                 265                 270

TTT ATC GAC AGC TTG CAG GAG AAC GAG TTC CGT CTG TAC TAC TAC AAC      864
Phe Ile Asp Ser Leu Gln Glu Asn Glu Phe Arg Leu Tyr Tyr Tyr Asn
            275                 280                 285

AAG TTT AAA GAT ATT GCA AGT ACA CTG AAC AAG GCT AAG TCC ATT GTG      912
Lys Phe Lys Asp Ile Ala Ser Thr Leu Asn Lys Ala Lys Ser Ile Val
290                 295                 300

GGT ACC ACT GCT TCA TTA CAG TAT ATG AAA AAT GTT TTT AAA GAG AAA      960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA     1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT     1056
Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT     1104
Asn Phe Val Lys Phe Phe Lys Val Leu Asn Arg Lys Thr Tyr Leu Asn
            355                 360                 365

TTT GAT AAA GCC GTA TTT AAG ATA AAT ATA GTA CCT AAG GTA AAT TAC     1152
Phe Asp Lys Ala Val Phe Lys Ile Asn Ile Val Pro Lys Val Asn Tyr
        370                 375                 380

ACA ATA TAT GAT GGA TTT AAT TTA AGA AAT ACA AAT TTA GCA GCA AAC     1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA     1248
Phe Asn Gly Gln Asn Thr Glu Ile Asn Asn Met Asn Phe Thr Lys Leu
```

-continued

```
                      405                 410                 415
AAA AAT TTT ACT GGA TTG TTT GAA TTT TAT AAG TTG CTA TGT GTA AGA       1296
Lys Asn Phe Thr Gly Leu Phe Glu Phe Tyr Lys Leu Leu Cys Val Arg
                420                 425                 430

GGG ATA ATA ACT TCT AAA ACT AAA TCA TTA GAT AAA GGA TAC AAT AAG       1344
Gly Ile Ile Thr Ser Lys Thr Lys Ser Leu Asp Lys Gly Tyr Asn Lys
                435                 440                 445

GCA TTA AAT GAT TTA TGT ATC AAA GTT AAT AAT TGG GAC TTG TTT TTT       1392
Ala Leu Asn Asp Leu Cys Ile Lys Val Asn Asn Trp Asp Leu Phe Phe
450                 455                 460

AGT CCT TCA GAA GAT AAT TTT ACT AAT GAT CTA AAT AAA GGA GAA GAA       1440
Ser Pro Ser Glu Asp Asn Phe Thr Asn Asp Leu Asn Lys Gly Glu Glu
465                 470                 475                 480

ATT ACA TCT GAT ACT AAT ATA GAA GCA GCA GAA GAA AAT ATT AGT TTA       1488
Ile Thr Ser Asp Thr Asn Ile Glu Ala Ala Glu Glu Asn Ile Ser Leu
                485                 490                 495

GAT TTA ATA CAA CAA TAT TAT TTA ACC TTT AAT TTT GAT AAT GAA CCT       1536
Asp Leu Ile Gln Gln Tyr Tyr Leu Thr Phe Asn Phe Asp Asn Glu Pro
                500                 505                 510

GAA AAT ATT TCA ATA GAA AAT CTT TCA AGT GAC ATT ATA GGC CAA TTA       1584
Glu Asn Ile Ser Ile Glu Asn Leu Ser Ser Asp Ile Ile Gly Gln Leu
                515                 520                 525

GAA CTT ATG CCT AAT ATA GAA AGA TTT CCT AAT GGA AAA AAG TAT GAG       1632
Glu Leu Met Pro Asn Ile Glu Arg Phe Pro Asn Gly Lys Lys Tyr Glu
530                 535                 540

TTA GAT AAA TAT ACT ATG TTC CAT TAT CTT CGT GCT CAA GAA TTT GAA       1680
Leu Asp Lys Tyr Thr Met Phe His Tyr Leu Arg Ala Gln Glu Phe Glu
545                 550                 555                 560

CAT GGT AAA TCT AGG ATT GCT TTA ACA AAT TCT GTT AAC GAA GCA TTA       1728
His Gly Lys Ser Arg Ile Ala Leu Thr Asn Ser Val Asn Glu Ala Leu
                565                 570                 575

TTA AAT CCT AGT CGT GTT TAT ACA TTT TTT TCT TCA GAC TAT GTA AAG       1776
Leu Asn Pro Ser Arg Val Tyr Thr Phe Phe Ser Ser Asp Tyr Val Lys
                580                 585                 590

AAA GTT AAT AAA GCT ACG GAG GCA GCT ATG TTT TTA GGC TGG GTA GAA       1824
Lys Val Asn Lys Ala Thr Glu Ala Ala Met Phe Leu Gly Trp Val Glu
                595                 600                 605

CAA TTA GTA TAT GAT TTT ACC GAT GAA ACT AGC GAA GTA AGT ACT ACG       1872
Gln Leu Val Tyr Asp Phe Thr Asp Glu Thr Ser Glu Val Ser Thr Thr
                610                 615                 620

GAT AAA ATT GCG GAT ATA ACT ATA ATT ATT CCA TAT ATA GGA CCT GCT       1920
Asp Lys Ile Ala Asp Ile Thr Ile Ile Ile Pro Tyr Ile Gly Pro Ala
625                 630                 635                 640

TTA AAT ATA GGT AAT ATG TTA TAT AAA GAT GAT TTT GTA GGT GCT TTA       1968
Leu Asn Ile Gly Asn Met Leu Tyr Lys Asp Asp Phe Val Gly Ala Leu
                645                 650                 655

ATA TTT TCA GGA GCT GTT ATT CTG TTA GAA TTT ATA CCA GAG ATT GCA       2016
Ile Phe Ser Gly Ala Val Ile Leu Leu Glu Phe Ile Pro Glu Ile Ala
                660                 665                 670

ATA CCT GTA TTA GGT ACT TTT GCA CTT GTA TCA TAT ATT GCG AAT AAG       2064
Ile Pro Val Leu Gly Thr Phe Ala Leu Val Ser Tyr Ile Ala Asn Lys
                675                 680                 685

GTT CTA ACC GTT CAA ACA ATA GAT AAT GCT TTA AGT AAA AGA AAT GAA       2112
Val Leu Thr Val Gln Thr Ile Asp Asn Ala Leu Ser Lys Arg Asn Glu
                690                 695                 700

AAA TGG GAT GAG GTC TAT AAA TAT ATA GTA ACA AAT TGG TTA GCA AAG       2160
Lys Trp Asp Glu Val Tyr Lys Tyr Ile Val Thr Asn Trp Leu Ala Lys
705                 710                 715                 720

GTT AAT ACA CAG ATT GAT CTA ATA AGA AAA AAA ATG AAA GAA GCT TTA       2208
```

```
Val Asn Thr Gln Ile Asp Leu Ile Arg Lys Lys Met Lys Glu Ala Leu
                725                 730                 735

GAA AAT CAA GCA GAA GCA ACA AAG GCT ATA ATA AAC TAT CAG TAT AAT          2256
Glu Asn Gln Ala Glu Ala Thr Lys Ala Ile Ile Asn Tyr Gln Tyr Asn
            740                 745                 750

CAA TAT ACT GAG GAA GAG AAA AAT AAT ATT AAT TTT AAT ATT GAT GAT          2304
Gln Tyr Thr Glu Glu Glu Lys Asn Asn Ile Asn Phe Asn Ile Asp Asp
        755                 760                 765

TTA AGT TCG AAA CTT AAT GAG TCT ATA AAT AAA GCT ATG ATT AAT ATA          2352
Leu Ser Ser Lys Leu Asn Glu Ser Ile Asn Lys Ala Met Ile Asn Ile
    770                 775                 780

AAT AAA TTT TTG AAT CAA TGC TCT GTT TCA TAT TTA ATG AAT TCT ATG          2400
Asn Lys Phe Leu Asn Gln Cys Ser Val Ser Tyr Leu Met Asn Ser Met
785                 790                 795                 800

ATC CCT TAT GGT GTT AAA CGG TTA GAA GAT TTT GAT GCT AGT CTT AAA          2448
Ile Pro Tyr Gly Val Lys Arg Leu Glu Asp Phe Asp Ala Ser Leu Lys
                805                 810                 815

GAT GCA TTA TTA AAG TAT ATA TAT GAT AAT AGA GGA ACT TTA ATT GGT          2496
Asp Ala Leu Leu Lys Tyr Ile Tyr Asp Asn Arg Gly Thr Leu Ile Gly
            820                 825                 830

CAA GTA GAT AGA TTA AAA GAT AAA GTT AAT AAT ACA CTT AGT ACA GAT          2544
Gln Val Asp Arg Leu Lys Asp Lys Val Asn Asn Thr Leu Ser Thr Asp
        835                 840                 845

ATA CCT TTT CAG CTT TCC AAA TAC GTA GAT AAT CAA AGA TTA TTA TCT          2592
Ile Pro Phe Gln Leu Ser Lys Tyr Val Asp Asn Gln Arg Leu Leu Ser
    850                 855                 860

ACA TTT ACT GAA TAT ATT AAG TAA                                          2616
Thr Phe Thr Glu Tyr Ile Lys
865                 870

(2) INFORMATION FOR SEQ ID NO: 2:

(i) SEQUENCE CHARACTERISTICS:
        (A) LENGTH: 871 amino acids
        (B) TYPE: amino acid
        (D) TOPOLOGY: linear (ii) MOLECULE TYPE: protein (xi) SEQUENCE DESCRIPTION: SEQ ID NO: 2:

Met Gln Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
             100                 105                 110

Arg Gly Ile Pro Phe Trp Gly Gly Ser Thr Ile Asp Thr Glu Leu Lys
         115                 120                 125

Val Ile Asp Thr Asn Cys Ile Asn Val Ile Gln Pro Asp Gly Ser Tyr
     130                 135                 140

Arg Ser Glu Glu Leu Asn Leu Val Ile Ile Gly Pro Ser Ala Asp Ile
```

-continued

```
            145                 150                 155                 160
    Ile Gln Phe Glu Cys Lys Ser Phe Gly His Glu Val Leu Asn Leu Thr
                    165                 170                 175

Arg Asn Gly Tyr Gly Ser Thr Gln Tyr Ile Arg Phe Ser Pro Asp Phe
                    180                 185                 190

Thr Phe Gly Phe Glu Glu Ser Leu Glu Val Asp Thr Asn Pro Leu Leu
                    195                 200                 205

Gly Ala Gly Lys Phe Ala Thr Asp Pro Ala Val Thr Leu Ala His Glu
                    210                 215                 220

Leu Ile His Ala Gly His Arg Leu Tyr Gly Ile Ala Ile Asn Pro Asn
    225                 230                 235                 240

Arg Val Phe Lys Val Asn Thr Asn Ala Tyr Tyr Glu Met Ser Gly Leu
                    245                 250                 255

Glu Val Ser Phe Glu Glu Leu Arg Thr Phe Gly Gly His Asp Ala Lys
                    260                 265                 270

Phe Ile Asp Ser Leu Gln Glu Asn Glu Phe Arg Leu Tyr Tyr Tyr Asn
                    275                 280                 285

Lys Phe Lys Asp Ile Ala Ser Thr Leu Asn Lys Ala Lys Ser Ile Val
                    290                 295                 300

Gly Thr Thr Ala Ser Leu Gln Tyr Met Lys Asn Val Phe Lys Glu Lys
    305                 310                 315                 320

Tyr Leu Leu Ser Glu Asp Thr Ser Gly Lys Phe Ser Val Asp Lys Leu
                    325                 330                 335

Lys Phe Asp Lys Leu Tyr Lys Met Leu Thr Glu Ile Tyr Thr Glu Asp
                    340                 345                 350

Asn Phe Val Lys Phe Phe Lys Val Leu Asn Arg Lys Thr Tyr Leu Asn
                    355                 360                 365

Phe Asp Lys Ala Val Phe Lys Ile Asn Ile Val Pro Lys Val Asn Tyr
                    370                 375                 380

Thr Ile Tyr Asp Gly Phe Asn Leu Arg Asn Thr Asn Leu Ala Ala Asn
    385                 390                 395                 400

Phe Asn Gly Gln Asn Thr Glu Ile Asn Asn Met Asn Phe Thr Lys Leu
                    405                 410                 415

Lys Asn Phe Thr Gly Leu Phe Glu Phe Tyr Lys Leu Leu Cys Val Arg
                    420                 425                 430

Gly Ile Ile Thr Ser Lys Thr Lys Ser Leu Asp Lys Gly Tyr Asn Lys
                    435                 440                 445

Ala Leu Asn Asp Leu Cys Ile Lys Val Asn Asn Trp Asp Leu Phe Phe
    450                 455                 460

Ser Pro Ser Glu Asp Asn Phe Thr Asn Asp Leu Asn Lys Gly Glu Glu
    465                 470                 475                 480

Ile Thr Ser Asp Thr Asn Ile Glu Ala Ala Glu Glu Asn Ile Ser Leu
                    485                 490                 495

Asp Leu Ile Gln Gln Tyr Tyr Leu Thr Phe Asn Phe Asp Asn Glu Pro
                    500                 505                 510

Glu Asn Ile Ser Ile Glu Asn Leu Ser Ser Asp Ile Ile Gly Gln Leu
                    515                 520                 525

Glu Leu Met Pro Asn Ile Glu Arg Phe Pro Asn Gly Lys Lys Tyr Glu
                    530                 535                 540

Leu Asp Lys Tyr Thr Met Phe His Tyr Leu Arg Ala Gln Glu Phe Glu
    545                 550                 555                 560

His Gly Lys Ser Arg Ile Ala Leu Thr Asn Ser Val Asn Glu Ala Leu
                    565                 570                 575
```

```
Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys
865             870
```

(2) INFORMATION FOR SEQ ID NO: 3:

(i) SEQUENCE CHARACTERISTICS:
        (A) LENGTH: 2685 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2685

(xi) SEQUENCE DESCRIPTION: SEQ ID NO: 3:

```
GGA TCC CCA GGA ATT CAT ATG ACG TCG ACG CGT CTG CAG AAG CTT CTA    48
Gly Ser Pro Gly Ile His Met Thr Ser Thr Arg Leu Gln Lys Leu Leu
  1               5                  10                  15
```

```
GAA TTC GAG CTC CCG GGT ACC ATG GAG TTC GTG AAC AAG CAG TTC AAC         96
Glu Phe Glu Leu Pro Gly Thr Met Glu Phe Val Asn Lys Gln Phe Asn
            20                  25                  30

TAT AAG GAC CCT GTA AAC GGT GTT GAC ATT GCC TAC ATC AAA ATT CCA        144
Tyr Lys Asp Pro Val Asn Gly Val Asp Ile Ala Tyr Ile Lys Ile Pro
        35                  40                  45

AAG TAC GGC CAG ATG CAG CCG GTG AAG GCT TTC AAG ATT CAT AAC AAA        192
Lys Tyr Gly Gln Met Gln Pro Val Lys Ala Phe Lys Ile His Asn Lys
    50                  55                  60

ATC TGG GTT ATT CCG GAA CGC GAT ACA TTT ACG AAC CCG GAA GAA GGA        240
Ile Trp Val Ile Pro Glu Arg Asp Thr Phe Thr Asn Pro Glu Glu Gly
65                  70                  75                  80

GAC TTG AAC CCG CCG CCG GAA GCA AAG CAG GTG CCA GTT TCA TAC TAC        288
Asp Leu Asn Pro Pro Pro Glu Ala Lys Gln Val Pro Val Ser Tyr Tyr
                85                  90                  95

GAT TCA ACC TAT CTG AGC ACA GAC AAC GAG AAG GAT AAC TAC CTG AAG        336
Asp Ser Thr Tyr Leu Ser Thr Asp Asn Glu Lys Asp Asn Tyr Leu Lys
            100                 105                 110

GGA GTG ACC AAA TTA TTC GAG CGT ATT TAT TCC ACT GAC CTG GGC CGT        384
Gly Val Thr Lys Leu Phe Glu Arg Ile Tyr Ser Thr Asp Leu Gly Arg
        115                 120                 125

ATG CTG CTG ACC TCA ATC GTC CGC GGA ATC CCA TTT TGG GGT GGC AGT        432
Met Leu Leu Thr Ser Ile Val Arg Gly Ile Pro Phe Trp Gly Gly Ser
    130                 135                 140

ACC ATT GAC ACG GAG TTG AAG GTT ATT GAC ACT AAC TGC ATT AAC GTG        480
Thr Ile Asp Thr Glu Leu Lys Val Ile Asp Thr Asn Cys Ile Asn Val
145                 150                 155                 160

ATC CAA CCA GAC GGT AGC TAC AGA TCT GAA GAA CTT AAC CTC GTA ATC        528
Ile Gln Pro Asp Gly Ser Tyr Arg Ser Glu Glu Leu Asn Leu Val Ile
                165                 170                 175

ATC GGG CCC TCC GCG GAC ATT ATC CAG TTT GAG TGC AAG AGC TTT GGC        576
Ile Gly Pro Ser Ala Asp Ile Ile Gln Phe Glu Cys Lys Ser Phe Gly
            180                 185                 190

CAC GAA GTG TTG AAC CTG ACG CGT AAC GGT TAC GGC TCT ACT CAG TAC        624
His Glu Val Leu Asn Leu Thr Arg Asn Gly Tyr Gly Ser Thr Gln Tyr
        195                 200                 205

ATT CGT TTC AGC CCA GAC TTC ACG TTC GGT TTC GAG GAG AGC CTG GAG        672
Ile Arg Phe Ser Pro Asp Phe Thr Phe Gly Phe Glu Glu Ser Leu Glu
    210                 215                 220

GTT GAT ACC AAC CCG CTG TTG GGT GCA GGC AAG TTC GCA ACT GAT CCA        720
Val Asp Thr Asn Pro Leu Leu Gly Ala Gly Lys Phe Ala Thr Asp Pro
225                 230                 235                 240

GCG GTG ACC CTG GCA CAC GAG CTG ATC CAC GCC GGT CAT CGT CTG TAT        768
Ala Val Thr Leu Ala His Glu Leu Ile His Ala Gly His Arg Leu Tyr
                245                 250                 255

GGC ATT GCG ATT AAC CCG AAC CGC GTG TTC AAG GTT AAC ACC AAC GCC        816
Gly Ile Ala Ile Asn Pro Asn Arg Val Phe Lys Val Asn Thr Asn Ala
            260                 265                 270

TAC TAC GAG ATG AGT GGT TTA GAA GTA AGC TTC GAG GAA CTG CGC ACG        864
Tyr Tyr Glu Met Ser Gly Leu Glu Val Ser Phe Glu Glu Leu Arg Thr
        275                 280                 285

TTC GGT GGC CAT GAT GCG AAG TTT ATC GAC AGC TTG CAG GAG AAC GAG        912
Phe Gly Gly His Asp Ala Lys Phe Ile Asp Ser Leu Gln Glu Asn Glu
    290                 295                 300

TTC CGT CTG TAC TAC TAC AAC AAG TTT AAA GAT ATT GCA AGT ACA CTG        960
Phe Arg Leu Tyr Tyr Tyr Asn Lys Phe Lys Asp Ile Ala Ser Thr Leu
305                 310                 315                 320

AAC AAG GCT AAG TCC ATT GTG GGT ACC ACT GCT TCA TTA CAG TAT ATG       1008
Asn Lys Ala Lys Ser Ile Val Gly Thr Thr Ala Ser Leu Gln Tyr Met
                325                 330                 335
```

```
AAA AAT GTT TTT AAA GAG AAA TAT CTC CTA TCT GAA GAT ACA TCT GGA      1056
Lys Asn Val Phe Lys Glu Lys Tyr Leu Leu Ser Glu Asp Thr Ser Gly
            340                 345                 350

AAA TTT TCG GTA GAT AAA TTA AAA TTT GAT AAG TTA TAC AAA ATG TTA      1104
Lys Phe Ser Val Asp Lys Leu Lys Phe Asp Lys Leu Tyr Lys Met Leu
            355                 360                 365

ACA GAG ATT TAC ACA GAG GAT AAT TTT GTT AAG TTT TTT AAA GTA CTT      1152
Thr Glu Ile Tyr Thr Glu Asp Asn Phe Val Lys Phe Phe Lys Val Leu
            370                 375                 380

AAC AGA AAA ACA TAT TTG AAT TTT GAT AAA GCC GTA TTT AAG ATA AAT      1200
Asn Arg Lys Thr Tyr Leu Asn Phe Asp Lys Ala Val Phe Lys Ile Asn
385                 390                 395                 400

ATA GTA CCT AAG GTA AAT TAC ACA ATA TAT GAT GGA TTT AAT TTA AGA      1248
Ile Val Pro Lys Val Asn Tyr Thr Ile Tyr Asp Gly Phe Asn Leu Arg
            405                 410                 415

AAT ACA AAT TTA GCA GCA AAC TTT AAT GGT CAA AAT ACA GAA ATT AAT      1296
Asn Thr Asn Leu Ala Ala Asn Phe Asn Gly Gln Asn Thr Glu Ile Asn
            420                 425                 430

AAT ATG AAT TTT ACT AAA CTA AAA AAT TTT ACT GGA TTG TTT GAA TTT      1344
Asn Met Asn Phe Thr Lys Leu Lys Asn Phe Thr Gly Leu Phe Glu Phe
            435                 440                 445

TAT AAG TTG CTA TGT GTA AGA GGG ATA ATA ACT TCT AAA ACT AAA TCA      1392
Tyr Lys Leu Leu Cys Val Arg Gly Ile Ile Thr Ser Lys Thr Lys Ser
450                 455                 460

TTA GAT AAA GGA TAC AAT AAG GCA TTA AAT GAT TTA TGT ATC AAA GTT      1440
Leu Asp Lys Gly Tyr Asn Lys Ala Leu Asn Asp Leu Cys Ile Lys Val
465                 470                 475                 480

AAT AAT TGG GAC TTG TTT TTT AGT CCT TCA GAA GAT AAT TTT ACT AAT      1488
Asn Asn Trp Asp Leu Phe Phe Ser Pro Ser Glu Asp Asn Phe Thr Asn
            485                 490                 495

GAT CTA AAT AAA GGA GAA GAA ATT ACA TCT GAT ACT AAT ATA GAA GCA      1536
Asp Leu Asn Lys Gly Glu Glu Ile Thr Ser Asp Thr Asn Ile Glu Ala
            500                 505                 510

GCA GAA GAA AAT ATT AGT TTA GAT TTA ATA CAA CAA TAT TAT TTA ACC      1584
Ala Glu Glu Asn Ile Ser Leu Asp Leu Ile Gln Gln Tyr Tyr Leu Thr
            515                 520                 525

TTT AAT TTT GAT AAT GAA CCT GAA AAT ATT TCA ATA GAA AAT CTT TCA      1632
Phe Asn Phe Asp Asn Glu Pro Glu Asn Ile Ser Ile Glu Asn Leu Ser
530                 535                 540

AGT GAC ATT ATA GGC CAA TTA GAA CTT ATG CCT AAT ATA GAA AGA TTT      1680
Ser Asp Ile Ile Gly Gln Leu Glu Leu Met Pro Asn Ile Glu Arg Phe
545                 550                 555                 560

CCT AAT GGA AAA AAG TAT GAG TTA GAT AAA TAT ACT ATG TTC CAT TAT      1728
Pro Asn Gly Lys Lys Tyr Glu Leu Asp Lys Tyr Thr Met Phe His Tyr
            565                 570                 575

CTT CGT GCT CAA GAA TTT GAA CAT GGT AAA TCT AGG ATT GCT TTA ACA      1776
Leu Arg Ala Gln Glu Phe Glu His Gly Lys Ser Arg Ile Ala Leu Thr
            580                 585                 590

AAT TCT GTT AAC GAA GCA TTA TTA AAT CCT AGT CGT GTT TAT ACA TTT      1824
Asn Ser Val Asn Glu Ala Leu Leu Asn Pro Ser Arg Val Tyr Thr Phe
            595                 600                 605

TTT TCT TCA GAC TAT GTA AAG AAA GTT AAT AAA GCT ACG GAG GCA GCT      1872
Phe Ser Ser Asp Tyr Val Lys Lys Val Asn Lys Ala Thr Glu Ala Ala
            610                 615                 620

ATG TTT TTA GGC TGG GTA GAA CAA TTA GTA TAT GAT TTT ACC GAT GAA      1920
Met Phe Leu Gly Trp Val Glu Gln Leu Val Tyr Asp Phe Thr Asp Glu
625                 630                 635                 640

ACT AGC GAA GTA AGT ACT ACG GAT AAA ATT GCG GAT ATA ACT ATA ATT      1968
Thr Ser Glu Val Ser Thr Thr Asp Lys Ile Ala Asp Ile Thr Ile Ile
```

```
                     645              650              655
ATT CCA TAT ATA GGA CCT GCT TTA AAT ATA GGT AAT ATG TTA TAT AAA     2016
Ile Pro Tyr Ile Gly Pro Ala Leu Asn Ile Gly Asn Met Leu Tyr Lys
            660              665              670

GAT GAT TTT GTA GGT GCT TTA ATA TTT TCA GGA GCT GTT ATT CTG TTA     2064
Asp Asp Phe Val Gly Ala Leu Ile Phe Ser Gly Ala Val Ile Leu Leu
        675              680              685

GAA TTT ATA CCA GAG ATT GCA ATA CCT GTA TTA GGT ACT TTT GCA CTT     2112
Glu Phe Ile Pro Glu Ile Ala Ile Pro Val Leu Gly Thr Phe Ala Leu
    690              695              700

GTA TCA TAT ATT GCG AAT AAG GTT CTA ACC GTT CAA ACA ATA GAT AAT     2160
Val Ser Tyr Ile Ala Asn Lys Val Leu Thr Val Gln Thr Ile Asp Asn
705             710              715              720

GCT TTA AGT AAA AGA AAT GAA AAA TGG GAT GAG GTC TAT AAA TAT ATA     2208
Ala Leu Ser Lys Arg Asn Glu Lys Trp Asp Glu Val Tyr Lys Tyr Ile
            725              730              735

GTA ACA AAT TGG TTA GCA AAG GTT AAT ACA CAG ATT GAT CTA ATA AGA     2256
Val Thr Asn Trp Leu Ala Lys Val Asn Thr Gln Ile Asp Leu Ile Arg
        740              745              750

AAA AAA ATG AAA GAA GCT TTA GAA AAT CAA GCA GAA GCA ACA AAG GCT     2304
Lys Lys Met Lys Glu Ala Leu Glu Asn Gln Ala Glu Ala Thr Lys Ala
    755              760              765

ATA ATA AAC TAT CAG TAT AAT CAA TAT ACT GAG GAA GAG AAA AAT AAT     2352
Ile Ile Asn Tyr Gln Tyr Asn Gln Tyr Thr Glu Glu Glu Lys Asn Asn
770             775              780

ATT AAT TTT AAT ATT GAT GAT TTA AGT TCG AAA CTT AAT GAG TCT ATA     2400
Ile Asn Phe Asn Ile Asp Asp Leu Ser Ser Lys Leu Asn Glu Ser Ile
785             790              795              800

AAT AAA GCT ATG ATT AAT ATA AAT AAA TTT TTG AAT CAA TGC TCT GTT     2448
Asn Lys Ala Met Ile Asn Ile Asn Lys Phe Leu Asn Gln Cys Ser Val
            805              810              815

TCA TAT TTA ATG AAT TCT ATG ATC CCT TAT GGT GTT AAA CGG TTA GAA     2496
Ser Tyr Leu Met Asn Ser Met Ile Pro Tyr Gly Val Lys Arg Leu Glu
        820              825              830

GAT TTT GAT GCT AGT CTT AAA GAT GCA TTA TTA AAG TAT ATA TAT GAT     2544
Asp Phe Asp Ala Ser Leu Lys Asp Ala Leu Leu Lys Tyr Ile Tyr Asp
    835              840              845

AAT AGA GGA ACT TTA ATT GGT CAA GTA GAT AGA TTA AAA GAT AAA GTT     2592
Asn Arg Gly Thr Leu Ile Gly Gln Val Asp Arg Leu Lys Asp Lys Val
850             855              860

AAT AAT ACA CTT AGT ACA GAT ATA CCT TTT CAG CTT TCC AAA TAC GTA     2640
Asn Asn Thr Leu Ser Thr Asp Ile Pro Phe Gln Leu Ser Lys Tyr Val
865             870              875              880

GAT AAT CAA AGA TTA TTA TCT ACA TTT ACT GAA TAT ATT AAG TAA          2685
Asp Asn Gln Arg Leu Leu Ser Thr Phe Thr Glu Tyr Ile Lys
            885              890
```

(2) INFORMATION FOR SEQ ID NO: 4:

(i) SEQUENCE CHARACTERISTICS:
        (A) LENGTH: 894 amino acids
        (B) TYPE: amino acid
        (D) TOPOLOGY: linear (ii) MOLECULE TYPE: protein (xi) SEQUENCE DESCRIPTION: SEQ ID NO: 4:

```
Gly Ser Pro Gly Ile His Met Thr Ser Thr Arg Leu Gln Lys Leu Leu
 1               5                  10                  15

Glu Phe Glu Leu Pro Gly Thr Met Glu Phe Val Asn Lys Gln Phe Asn
            20                  25                  30
```

-continued

```
Tyr Lys Asp Pro Val Asn Gly Val Asp Ile Ala Tyr Ile Lys Ile Pro
         35                  40                  45
Lys Tyr Gly Gln Met Gln Pro Val Lys Ala Phe Lys Ile His Asn Lys
         50                  55                  60
Ile Trp Val Ile Pro Glu Arg Asp Thr Phe Thr Asn Pro Glu Glu Gly
 65                  70                  75                  80
Asp Leu Asn Pro Pro Pro Glu Ala Lys Gln Val Pro Val Ser Tyr Tyr
                 85                  90                  95
Asp Ser Thr Tyr Leu Ser Thr Asp Asn Glu Lys Asp Asn Tyr Leu Lys
                100                 105                 110
Gly Val Thr Lys Leu Phe Glu Arg Ile Tyr Ser Thr Asp Leu Gly Arg
             115                 120                 125
Met Leu Leu Thr Ser Ile Val Arg Gly Ile Pro Phe Trp Gly Gly Ser
     130                 135                 140
Thr Ile Asp Thr Glu Leu Lys Val Ile Asp Thr Asn Cys Ile Asn Val
145                 150                 155                 160
Ile Gln Pro Asp Gly Ser Tyr Arg Ser Glu Glu Leu Asn Leu Val Ile
                 165                 170                 175
Ile Gly Pro Ser Ala Asp Ile Ile Gln Phe Glu Cys Lys Ser Phe Gly
             180                 185                 190
His Glu Val Leu Asn Leu Thr Arg Asn Gly Tyr Gly Ser Thr Gln Tyr
         195                 200                 205
Ile Arg Phe Ser Pro Asp Phe Thr Phe Gly Phe Glu Glu Ser Leu Glu
     210                 215                 220
Val Asp Thr Asn Pro Leu Leu Gly Ala Gly Lys Phe Ala Thr Asp Pro
225                 230                 235                 240
Ala Val Thr Leu Ala His Glu Leu Ile His Ala Gly His Arg Leu Tyr
                 245                 250                 255
Gly Ile Ala Ile Asn Pro Asn Arg Val Phe Lys Val Asn Thr Asn Ala
             260                 265                 270
Tyr Tyr Glu Met Ser Gly Leu Glu Val Ser Phe Glu Glu Leu Arg Thr
     275                 280                 285
Phe Gly Gly His Asp Ala Lys Phe Ile Asp Ser Leu Gln Glu Asn Glu
 290                 295                 300
Phe Arg Leu Tyr Tyr Tyr Asn Lys Phe Lys Asp Ile Ala Ser Thr Leu
305                 310                 315                 320
Asn Lys Ala Lys Ser Ile Val Gly Thr Thr Ala Ser Leu Gln Tyr Met
                 325                 330                 335
Lys Asn Val Phe Lys Glu Lys Tyr Leu Leu Ser Glu Asp Thr Ser Gly
             340                 345                 350
Lys Phe Ser Val Asp Lys Leu Lys Phe Asp Lys Leu Tyr Lys Met Leu
     355                 360                 365
Thr Glu Ile Tyr Thr Glu Asp Asn Phe Val Lys Phe Phe Lys Val Leu
 370                 375                 380
Asn Arg Lys Thr Tyr Leu Asn Phe Asp Lys Ala Val Phe Lys Ile Asn
385                 390                 395                 400
Ile Val Pro Lys Val Asn Tyr Thr Ile Tyr Asp Gly Phe Asn Leu Arg
                 405                 410                 415
Asn Thr Asn Leu Ala Ala Asn Phe Asn Gly Gln Asn Thr Glu Ile Asn
             420                 425                 430
Asn Met Asn Phe Thr Lys Leu Lys Asn Phe Thr Gly Leu Phe Glu Phe
     435                 440                 445
```

```
Tyr Lys Leu Leu Cys Val Arg Gly Ile Ile Thr Ser Lys Thr Lys Ser
    450                 455                 460
Leu Asp Lys Gly Tyr Asn Lys Ala Leu Asn Asp Leu Cys Ile Lys Val
465                 470                 475                 480
Asn Asn Trp Asp Leu Phe Phe Ser Pro Ser Glu Asp Asn Phe Thr Asn
                485                 490                 495
Asp Leu Asn Lys Gly Glu Glu Ile Thr Ser Asp Thr Asn Ile Glu Ala
                500                 505                 510
Ala Glu Glu Asn Ile Ser Leu Asp Leu Ile Gln Gln Tyr Tyr Leu Thr
            515                 520                 525
Phe Asn Phe Asp Asn Glu Pro Glu Asn Ile Ser Ile Glu Asn Leu Ser
    530                 535                 540
Ser Asp Ile Ile Gly Gln Leu Glu Leu Met Pro Asn Ile Glu Arg Phe
545                 550                 555                 560
Pro Asn Gly Lys Lys Tyr Glu Leu Asp Lys Tyr Thr Met Phe His Tyr
                565                 570                 575
Leu Arg Ala Gln Glu Phe Glu His Gly Lys Ser Arg Ile Ala Leu Thr
                580                 585                 590
Asn Ser Val Asn Glu Ala Leu Leu Asn Pro Ser Arg Val Tyr Thr Phe
    595                 600                 605
Phe Ser Ser Asp Tyr Val Lys Lys Val Asn Lys Ala Thr Glu Ala Ala
    610                 615                 620
Met Phe Leu Gly Trp Val Glu Gln Leu Val Tyr Asp Phe Thr Asp Glu
625                 630                 635                 640
Thr Ser Glu Val Ser Thr Thr Asp Lys Ile Ala Asp Ile Thr Ile Ile
                645                 650                 655
Ile Pro Tyr Ile Gly Pro Ala Leu Asn Ile Gly Asn Met Leu Tyr Lys
                660                 665                 670
Asp Asp Phe Val Gly Ala Leu Ile Phe Ser Gly Ala Val Ile Leu Leu
            675                 680                 685
Glu Phe Ile Pro Glu Ile Ala Ile Pro Val Leu Gly Thr Phe Ala Leu
    690                 695                 700
Val Ser Tyr Ile Ala Asn Lys Val Leu Thr Val Gln Thr Ile Asp Asn
705                 710                 715                 720
Ala Leu Ser Lys Arg Asn Glu Lys Trp Asp Glu Val Tyr Lys Tyr Ile
                725                 730                 735
Val Thr Asn Trp Leu Ala Lys Val Asn Thr Gln Ile Asp Leu Ile Arg
                740                 745                 750
Lys Lys Met Lys Glu Ala Leu Glu Asn Gln Ala Glu Ala Thr Lys Ala
            755                 760                 765
Ile Ile Asn Tyr Gln Tyr Asn Gln Tyr Thr Glu Glu Lys Asn Asn
    770                 775                 780
Ile Asn Phe Asn Ile Asp Asp Leu Ser Ser Lys Leu Asn Glu Ser Ile
785                 790                 795                 800
Asn Lys Ala Met Ile Asn Ile Asn Lys Phe Leu Asn Gln Cys Ser Val
                805                 810                 815
Ser Tyr Leu Met Asn Ser Met Ile Pro Tyr Gly Val Lys Arg Leu Glu
                820                 825                 830
Asp Phe Asp Ala Ser Leu Lys Asp Ala Leu Leu Lys Tyr Ile Tyr Asp
            835                 840                 845
Asn Arg Gly Thr Leu Ile Gly Gln Val Asp Arg Leu Lys Asp Lys Val
    850                 855                 860
Asn Asn Thr Leu Ser Thr Asp Ile Pro Phe Gln Leu Ser Lys Tyr Val
```

```
                865                 870                 875                 880
Asp Asn Gln Arg Leu Leu Ser Thr Phe Thr Glu Tyr Ile Lys
                    885                 890

(2) INFORMATION FOR SEQ ID NO: 5:

(i) SEQUENCE CHARACTERISTICS:
        (A) LENGTH: 2622 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2622

(xi) SEQUENCE DESCRIPTION: SEQ ID NO: 5:

GGA TCC ATG GAG TTC GTG AAC AAG CAG TTC AAC TAT AAG GAC CCT GTA        48
Gly Ser Met Glu Phe Val Asn Lys Gln Phe Asn Tyr Lys Asp Pro Val
  1               5                  10                  15

AAC GGT GTT GAC ATT GCC TAC ATC AAA ATT CCA AAG TAC GGC CAG ATG        96
Asn Gly Val Asp Ile Ala Tyr Ile Lys Ile Pro Lys Tyr Gly Gln Met
             20                  25                  30

CAG CCG GTG AAG GCT TTC AAG ATT CAT AAC AAA ATC TGG GTT ATT CCG       144
Gln Pro Val Lys Ala Phe Lys Ile His Asn Lys Ile Trp Val Ile Pro
         35                  40                  45

GAA CGC GAT ACA TTT ACG AAC CCG GAA GAA GGA GAC TTG AAC CCG CCG       192
Glu Arg Asp Thr Phe Thr Asn Pro Glu Glu Gly Asp Leu Asn Pro Pro
     50                  55                  60

CCG GAA GCA AAG CAG GTG CCA GTT TCA TAC TAC GAT TCA ACC TAT CTG       240
Pro Glu Ala Lys Gln Val Pro Val Ser Tyr Tyr Asp Ser Thr Tyr Leu
 65                  70                  75                  80

AGC ACA GAC AAC GAG AAG GAT AAC TAC CTG AAG GGA GTG ACC AAA TTA       288
Ser Thr Asp Asn Glu Lys Asp Asn Tyr Leu Lys Gly Val Thr Lys Leu
                 85                  90                  95

TTC GAG CGT ATT TAT TCC ACT GAC CTG GGC CGT ATG CTG CTG ACC TCA       336
Phe Glu Arg Ile Tyr Ser Thr Asp Leu Gly Arg Met Leu Leu Thr Ser
            100                 105                 110

ATC GTC CGC GGA ATC CCA TTT TGG GGT GGC AGT ACC ATT GAC ACG GAG       384
Ile Val Arg Gly Ile Pro Phe Trp Gly Gly Ser Thr Ile Asp Thr Glu
        115                 120                 125

TTG AAG GTT ATT GAC ACT AAC TGC ATT AAC GTG ATC CAA CCA GAC GGT       432
Leu Lys Val Ile Asp Thr Asn Cys Ile Asn Val Ile Gln Pro Asp Gly
    130                 135                 140

AGC TAC AGA TCT GAA GAA CTT AAC CTC GTA ATC ATC GGG CCC TCC GCG       480
Ser Tyr Arg Ser Glu Glu Leu Asn Leu Val Ile Ile Gly Pro Ser Ala
145                 150                 155                 160

GAC ATT ATC CAG TTT GAG TGC AAG AGC TTT GGC CAC GAA GTG TTG AAC       528
Asp Ile Ile Gln Phe Glu Cys Lys Ser Phe Gly His Glu Val Leu Asn
                165                 170                 175

CTG ACG CGT AAC GGT TAC GGC TCT ACT CAG TAC ATT CGT TTC AGC CCA       576
Leu Thr Arg Asn Gly Tyr Gly Ser Thr Gln Tyr Ile Arg Phe Ser Pro
            180                 185                 190

GAC TTC ACG TTC GGT TTC GAG GAG AGC CTG GAG GTT GAT ACC AAC CCG       624
Asp Phe Thr Phe Gly Phe Glu Glu Ser Leu Glu Val Asp Thr Asn Pro
        195                 200                 205

CTG TTG GGT GCA GGC AAG TTC GCA ACT GAT CCA GCG GTG ACC CTG GCA       672
Leu Leu Gly Ala Gly Lys Phe Ala Thr Asp Pro Ala Val Thr Leu Ala
    210                 215                 220

CAC GAG CTG ATC CAC GCC GGT CAT CGT CTG TAT GGC ATT GCG ATT AAC       720
```

-continued

```
His Glu Leu Ile His Ala Gly His Arg Leu Tyr Gly Ile Ala Ile Asn
225                 230                 235                 240

CCG AAC CGC GTG TTC AAG GTT AAC ACC AAC GCC TAC TAC GAG ATG AGT        768
Pro Asn Arg Val Phe Lys Val Asn Thr Asn Ala Tyr Tyr Glu Met Ser
                245                 250                 255

GGT TTA GAA GTA AGC TTC GAG GAA CTG CGC ACG TTC GGT GGC CAT GAT        816
Gly Leu Glu Val Ser Phe Glu Glu Leu Arg Thr Phe Gly Gly His Asp
            260                 265                 270

GCG AAG TTT ATC GAC AGC TTG CAG GAG AAC GAG TTC CGT CTG TAC TAC        864
Ala Lys Phe Ile Asp Ser Leu Gln Glu Asn Glu Phe Arg Leu Tyr Tyr
        275                 280                 285

TAC AAC AAG TTT AAA GAT ATT GCA AGT ACA CTG AAC AAG GCT AAG TCC        912
Tyr Asn Lys Phe Lys Asp Ile Ala Ser Thr Leu Asn Lys Ala Lys Ser
    290                 295                 300

ATT GTG GGT ACC ACT GCT TCA TTA CAG TAT ATG AAA AAT GTT TTT AAA        960
Ile Val Gly Thr Thr Ala Ser Leu Gln Tyr Met Lys Asn Val Phe Lys
305                 310                 315                 320

GAG AAA TAT CTC CTA TCT GAA GAT ACA TCT GGA AAA TTT TCG GTA GAT       1008
Glu Lys Tyr Leu Leu Ser Glu Asp Thr Ser Gly Lys Phe Ser Val Asp
                325                 330                 335

AAA TTA AAA TTT GAT AAG TTA TAC AAA ATG TTA ACA GAG ATT TAC ACA       1056
Lys Leu Lys Phe Asp Lys Leu Tyr Lys Met Leu Thr Glu Ile Tyr Thr
            340                 345                 350

GAG GAT AAT TTT GTT AAG TTT TTT AAA GTA CTT AAC AGA AAA ACA TAT       1104
Glu Asp Asn Phe Val Lys Phe Phe Lys Val Leu Asn Arg Lys Thr Tyr
        355                 360                 365

TTG AAT TTT GAT AAA GCC GTA TTT AAG ATA AAT ATA GTA CCT AAG GTA       1152
Leu Asn Phe Asp Lys Ala Val Phe Lys Ile Asn Ile Val Pro Lys Val
    370                 375                 380

AAT TAC ACA ATA TAT GAT GGA TTT AAT TTA AGA AAT ACA AAT TTA GCA       1200
Asn Tyr Thr Ile Tyr Asp Gly Phe Asn Leu Arg Asn Thr Asn Leu Ala
385                 390                 395                 400

GCA AAC TTT AAT GGT CAA AAT ACA GAA ATT AAT AAT ATG AAT TTT ACT       1248
Ala Asn Phe Asn Gly Gln Asn Thr Glu Ile Asn Asn Met Asn Phe Thr
                405                 410                 415

AAA CTA AAA AAT TTT ACT GGA TTG TTT GAA TTT TAT AAG TTG CTA TGT       1296
Lys Leu Lys Asn Phe Thr Gly Leu Phe Glu Phe Tyr Lys Leu Leu Cys
            420                 425                 430

GTA AGA GGG ATA ATA ACT TCT AAA ACT AAA TCA TTA GAT AAA GGA TAC       1344
Val Arg Gly Ile Ile Thr Ser Lys Thr Lys Ser Leu Asp Lys Gly Tyr
        435                 440                 445

AAT AAG GCA TTA AAT GAT TTA TGT ATC AAA GTT AAT AAT TGG GAC TTG       1392
Asn Lys Ala Leu Asn Asp Leu Cys Ile Lys Val Asn Asn Trp Asp Leu
    450                 455                 460

TTT TTT AGT CCT TCA GAA GAT AAT TTT ACT AAT GAT CTA AAT AAA GGA       1440
Phe Phe Ser Pro Ser Glu Asp Asn Phe Thr Asn Asp Leu Asn Lys Gly
465                 470                 475                 480

GAA GAA ATT ACA TCT GAT ACT AAT ATA GAA GCA GCA GAA GAA AAT ATT       1488
Glu Glu Ile Thr Ser Asp Thr Asn Ile Glu Ala Ala Glu Glu Asn Ile
                485                 490                 495

AGT TTA GAT TTA ATA CAA CAA TAT TAT TTA ACC TTT AAT TTT GAT AAT       1536
Ser Leu Asp Leu Ile Gln Gln Tyr Tyr Leu Thr Phe Asn Phe Asp Asn
            500                 505                 510

GAA CCT GAA AAT ATT TCA ATA GAA AAT CTT TCA AGT GAC ATT ATA GGC       1584
Glu Pro Glu Asn Ile Ser Ile Glu Asn Leu Ser Ser Asp Ile Ile Gly
        515                 520                 525

CAA TTA GAA CTT ATG CCT AAT ATA GAA AGA TTT CCT AAT GGA AAA AAG       1632
Gln Leu Glu Leu Met Pro Asn Ile Glu Arg Phe Pro Asn Gly Lys Lys
    530                 535                 540
```

```
TAT GAG TTA GAT AAA TAT ACT ATG TTC CAT TAT CTT CGT GCT CAA GAA    1680
Tyr Glu Leu Asp Lys Tyr Thr Met Phe His Tyr Leu Arg Ala Gln Glu
545                 550                 555                 560

TTT GAA CAT GGT AAA TCT AGG ATT GCT TTA ACA AAT TCT GTT AAC GAA    1728
Phe Glu His Gly Lys Ser Arg Ile Ala Leu Thr Asn Ser Val Asn Glu
                565                 570                 575

GCA TTA TTA AAT CCT AGT CGT GTT TAT ACA TTT TTT TCT TCA GAC TAT    1776
Ala Leu Leu Asn Pro Ser Arg Val Tyr Thr Phe Phe Ser Ser Asp Tyr
            580                 585                 590

GTA AAG AAA GTT AAT AAA GCT ACG GAG GCA GCT ATG TTT TTA GGC TGG    1824
Val Lys Lys Val Asn Lys Ala Thr Glu Ala Ala Met Phe Leu Gly Trp
        595                 600                 605

GTA GAA CAA TTA GTA TAT GAT TTT ACC GAT GAA ACT AGC GAA GTA AGT    1872
Val Glu Gln Leu Val Tyr Asp Phe Thr Asp Glu Thr Ser Glu Val Ser
610                 615                 620

ACT ACG GAT AAA ATT GCG GAT ATA ACT ATA ATT ATT CCA TAT ATA GGA    1920
Thr Thr Asp Lys Ile Ala Asp Ile Thr Ile Ile Ile Pro Tyr Ile Gly
625                 630                 635                 640

CCT GCT TTA AAT ATA GGT AAT ATG TTA TAT AAA GAT GAT TTT GTA GGT    1968
Pro Ala Leu Asn Ile Gly Asn Met Leu Tyr Lys Asp Asp Phe Val Gly
                645                 650                 655

GCT TTA ATA TTT TCA GGA GCT GTT ATT CTG TTA GAA TTT ATA CCA GAG    2016
Ala Leu Ile Phe Ser Gly Ala Val Ile Leu Leu Glu Phe Ile Pro Glu
            660                 665                 670

ATT GCA ATA CCT GTA TTA GGT ACT TTT GCA CTT GTA TCA TAT ATT GCG    2064
Ile Ala Ile Pro Val Leu Gly Thr Phe Ala Leu Val Ser Tyr Ile Ala
        675                 680                 685

AAT AAG GTT CTA ACC GTT CAA ACA ATA GAT AAT GCT TTA AGT AAA AGA    2112
Asn Lys Val Leu Thr Val Gln Thr Ile Asp Asn Ala Leu Ser Lys Arg
    690                 695                 700

AAT GAA AAA TGG GAT GAG GTC TAT AAA TAT ATA GTA ACA AAT TGG TTA    2160
Asn Glu Lys Trp Asp Glu Val Tyr Lys Tyr Ile Val Thr Asn Trp Leu
705                 710                 715                 720

GCA AAG GTT AAT ACA CAG ATT GAT CTA ATA AGA AAA AAA ATG AAA GAA    2208
Ala Lys Val Asn Thr Gln Ile Asp Leu Ile Arg Lys Lys Met Lys Glu
                725                 730                 735

GCT TTA GAA AAT CAA GCA GAA GCA ACA AAG GCT ATA ATA AAC TAT CAG    2256
Ala Leu Glu Asn Gln Ala Glu Ala Thr Lys Ala Ile Ile Asn Tyr Gln
            740                 745                 750

TAT AAT CAA TAT ACT GAG GAA GAG AAA AAT AAT ATT AAT TTT AAT ATT    2304
Tyr Asn Gln Tyr Thr Glu Glu Glu Lys Asn Asn Ile Asn Phe Asn Ile
        755                 760                 765

GAT GAT TTA AGT TCG AAA CTT AAT GAG TCT ATA AAT AAA GCT ATG ATT    2352
Asp Asp Leu Ser Ser Lys Leu Asn Glu Ser Ile Asn Lys Ala Met Ile
    770                 775                 780

AAT ATA AAT AAA TTT TTG AAT CAA TGC TCT GTT TCA TAT TTA ATG AAT    2400
Asn Ile Asn Lys Phe Leu Asn Gln Cys Ser Val Ser Tyr Leu Met Asn
785                 790                 795                 800

TCT ATG ATC CCT TAT GGT GTT AAA CGG TTA GAA GAT TTT GAT GCT AGT    2448
Ser Met Ile Pro Tyr Gly Val Lys Arg Leu Glu Asp Phe Asp Ala Ser
                805                 810                 815

CTT AAA GAT GCA TTA TTA AAG TAT ATA TAT GAT AAT AGA GGA ACT TTA    2496
Leu Lys Asp Ala Leu Leu Lys Tyr Ile Tyr Asp Asn Arg Gly Thr Leu
            820                 825                 830

ATT GGT CAA GTA GAT AGA TTA AAA GAT AAA GTT AAT AAT ACA CTT AGT    2544
Ile Gly Gln Val Asp Arg Leu Lys Asp Lys Val Asn Asn Thr Leu Ser
        835                 840                 845

ACA GAT ATA CCT TTT CAG CTT TCC AAA TAC GTA GAT AAT CAA AGA TTA    2592
Thr Asp Ile Pro Phe Gln Leu Ser Lys Tyr Val Asp Asn Gln Arg Leu
    850                 855                 860
```

```
TTA TCT ACA TTT ACT GAA TAT ATT AAG TAA                              2622
Leu Ser Thr Phe Thr Glu Tyr Ile Lys
865                 870
```

(2) INFORMATION FOR SEQ ID NO: 6:

(i) SEQUENCE CHARACTERISTICS:
        (A) LENGTH: 873 amino acids
        (B) TYPE: amino acid
        (D) TOPOLOGY: linear (ii) MOLECULE TYPE: protein (xi) SEQUENCE DESCRIPTION: SEQ ID NO: 6:

```
Gly Ser Met Glu Phe Val Asn Lys Gln Phe Asn Tyr Lys Asp Pro Val
 1               5                  10                  15

Asn Gly Val Asp Ile Ala Tyr Ile Lys Ile Pro Lys Tyr Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335
```

```
Lys Leu Lys Phe Asp Lys Leu Tyr Lys Met Leu Thr Glu Ile Tyr Thr
            340                 345                 350
Glu Asp Asn Phe Val Lys Phe Phe Lys Val Leu Asn Arg Lys Thr Tyr
            355                 360                 365
Leu Asn Phe Asp Lys Ala Val Phe Lys Ile Asn Ile Val Pro Lys Val
370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
            405                 410                 415
Lys Leu Lys Asn Phe Thr Gly Leu Phe Glu Phe Tyr Lys Leu Leu Cys
            420                 425                 430
Val Arg Gly Ile Ile Thr Ser Lys Thr Lys Ser Leu Asp Lys Gly Tyr
            435                 440                 445
Asn Lys Ala Leu Asn Asp Leu Cys Ile Lys Val Asn Asn Trp Asp Leu
450                 455                 460
Phe Phe Ser Pro Ser Glu Asp Asn Phe Thr Asn Asp Leu Asn Lys Gly
465                 470                 475                 480
Glu Glu Ile Thr Ser Asp Thr Asn Ile Glu Ala Ala Glu Asn Ile
            485                 490                 495
Ser Leu Asp Leu Ile Gln Gln Tyr Tyr Leu Thr Phe Asn Phe Asp Asn
            500                 505                 510
Glu Pro Glu Asn Ile Ser Ile Glu Asn Leu Ser Ser Asp Ile Ile Gly
            515                 520                 525
Gln Leu Glu Leu Met Pro Asn Ile Glu Arg Phe Pro Asn Gly Lys Lys
            530                 535                 540
Tyr Glu Leu Asp Lys Tyr Thr Met Phe His Tyr Leu Arg Ala Gln Glu
545                 550                 555                 560
Phe Glu His Gly Lys Ser Arg Ile Ala Leu Thr Asn Ser Val Asn Glu
            565                 570                 575
Ala Leu Leu Asn Pro Ser Arg Val Tyr Thr Phe Phe Ser Ser Asp Tyr
            580                 585                 590
Val Lys Lys Val Asn Lys Ala Thr Glu Ala Ala Met Phe Leu Gly Trp
            595                 600                 605
Val Glu Gln Leu Val Tyr Asp Phe Thr Asp Glu Thr Ser Glu Val Ser
610                 615                 620
Thr Thr Asp Lys Ile Ala Asp Ile Thr Ile Ile Pro Tyr Ile Gly
625                 630                 635                 640
Pro Ala Leu Asn Ile Gly Asn Met Leu Tyr Lys Asp Asp Phe Val Gly
            645                 650                 655
Ala Leu Ile Phe Ser Gly Ala Val Ile Leu Leu Glu Phe Ile Pro Glu
            660                 665                 670
Ile Ala Ile Pro Val Leu Gly Thr Phe Ala Leu Val Ser Tyr Ile Ala
            675                 680                 685
Asn Lys Val Leu Thr Val Gln Thr Ile Asp Asn Ala Leu Ser Lys Arg
            690                 695                 700
Asn Glu Lys Trp Asp Glu Val Tyr Lys Tyr Ile Val Thr Asn Trp Leu
705                 710                 715                 720
Ala Lys Val Asn Thr Gln Ile Asp Leu Ile Arg Lys Met Lys Glu
            725                 730                 735
Ala Leu Glu Asn Gln Ala Glu Ala Thr Lys Ala Ile Ile Asn Tyr Gln
            740                 745                 750
```

```
Tyr Asn Gln Tyr Thr Glu Glu Lys Asn Asn Ile Asn Phe Asn Ile
        755                 760                 765

Asp Asp Leu Ser Ser Lys Leu Asn Glu Ser Ile Asn Lys Ala Met Ile
        770                 775                 780

Asn Ile Asn Lys Phe Leu Asn Gln Cys Ser Val Ser Tyr Leu Met Asn
785                 790                 795                 800

Ser Met Ile Pro Tyr Gly Val Lys Arg Leu Glu Asp Phe Asp Ala Ser
                805                 810                 815

Leu Lys Asp Ala Leu Leu Lys Tyr Ile Tyr Asp Asn Arg Gly Thr Leu
        820                 825                 830

Ile Gly Gln Val Asp Arg Leu Lys Asp Lys Val Asn Asn Thr Leu Ser
        835                 840                 845

Thr Asp Ile Pro Phe Gln Leu Ser Lys Tyr Val Asp Asn Gln Arg Leu
        850                 855                 860

Leu Ser Thr Phe Thr Glu Tyr Ile Lys
865                 870
```

(2) INFORMATION FOR SEQ ID NO: 7:

(i) SEQUENCE CHARACTERISTICS:
        (A) LENGTH: 2613 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2613

(xi) SEQUENCE DESCRIPTION: SEQ ID NO: 7:

```
ATG CCA TTT GTT AAT AAA CAA TTT AAT TAT AAA GAT CCT GTA AAT GGT        48
Met Pro Phe Val Asn Lys Gln Phe Asn Tyr Lys Asp Pro Val Asn Gly
1               5                  10                  15

GTT GAT ATT GCT TAT ATA AAA ATT CCA AAT GCA GGA CAA ATG CAA CCA        96
Val Asp Ile Ala Tyr Ile Lys Ile Pro Asn Ala Gly Gln Met Gln Pro
            20                  25                  30

GTA AAA GCT TTT AAA ATT CAT AAT AAA ATA TGG GTT ATT CCA GAA AGA       144
Val Lys Ala Phe Lys Ile His Asn Lys Ile Trp Val Ile Pro Glu Arg
        35                  40                  45

GAT ACA TTT ACA AAT CCT GAA GAA GGA GAT TTA AAT CCA CCA CCA GAA       192
Asp Thr Phe Thr Asn Pro Glu Glu Gly Asp Leu Asn Pro Pro Pro Glu
    50                  55                  60

GCA AAA CAA GTT CCA GTT TCA TAT TAT GAT TCA ACA TAT TTA AGT ACA       240
Ala Lys Gln Val Pro Val Ser Tyr Tyr Asp Ser Thr Tyr Leu Ser Thr
65                  70                  75                  80

GAT AAT GAA AAA GAT AAT TAT TTA AAG GGA GTT ACA AAA TTA TTT GAG       288
Asp Asn Glu Lys Asp Asn Tyr Leu Lys Gly Val Thr Lys Leu Phe Glu
                85                  90                  95

AGA ATT TAT TCA ACT GAT CTT GGA AGA ATG TTG TTA ACA TCA ATA GTA       336
Arg Ile Tyr Ser Thr Asp Leu Gly Arg Met Leu Leu Thr Ser Ile Val
            100                 105                 110

AGG GGA ATA CCA TTT TGG GGT GGA AGT ACA ATA GAT ACA GAA TTA AAA       384
Arg Gly Ile Pro Phe Trp Gly Gly Ser Thr Ile Asp Thr Glu Leu Lys
        115                 120                 125

GTT ATT GAT ACT AAT TGT ATT AAT GTG ATA CAA CCA GAT GGT AGT TAT       432
Val Ile Asp Thr Asn Cys Ile Asn Val Ile Gln Pro Asp Gly Ser Tyr
    130                 135                 140

AGA TCA GAA GAA CTT AAT CTA GTA ATA ATA GGA CCC TCA GCT GAT ATT       480
Arg Ser Glu Glu Leu Asn Leu Val Ile Ile Gly Pro Ser Ala Asp Ile
```

```
                                                      -continued 145                     150                     155                     160
ATA CAG TTT GAA TGT AAA AGC TTT GGA CAT GAA GTT TTG AAT CTT ACG          528
Ile Gln Phe Glu Cys Lys Ser Phe Gly His Glu Val Leu Asn Leu Thr
                    165                     170                     175

CGA AAT GGT TAT GGC TCT ACT CAA TAC ATT AGA TTT AGC CCA GAT TTT          576
Arg Asn Gly Tyr Gly Ser Thr Gln Tyr Ile Arg Phe Ser Pro Asp Phe
                180                     185                     190

ACA TTT GGT TTT GAG GAG TCA CTT GAA GTT GAT ACA AAT CCT CTT TTA          624
Thr Phe Gly Phe Glu Glu Ser Leu Glu Val Asp Thr Asn Pro Leu Leu
                195                     200                     205

GGT GCA GGC AAA TTT GCT ACA GAT CCA GCA GTA ACA TTA GCA CAT GAA          672
Gly Ala Gly Lys Phe Ala Thr Asp Pro Ala Val Thr Leu Ala His Glu
        210                     215                     220

CTT ATA CAT GCT GGA CAT AGA TTA TAT GGA ATA GCA ATT AAT CCA AAT          720
Leu Ile His Ala Gly His Arg Leu Tyr Gly Ile Ala Ile Asn Pro Asn
225                     230                     235                     240

AGG GTT TTT AAA GTA AAT ACT AAT GCC TAT TAT GAA ATG AGT GGG TTA          768
Arg Val Phe Lys Val Asn Thr Asn Ala Tyr Tyr Glu Met Ser Gly Leu
                    245                     250                     255

GAA GTA AGC TTT GAG GAA CTT AGA ACA TTT GGG GGA CAT GAT GCA AAG          816
Glu Val Ser Phe Glu Glu Leu Arg Thr Phe Gly Gly His Asp Ala Lys
                260                     265                     270

TTT ATA GAT AGT TTA CAG GAA AAC GAA TTT CGT CTA TAT TAT TAT AAT          864
Phe Ile Asp Ser Leu Gln Glu Asn Glu Phe Arg Leu Tyr Tyr Tyr Asn
                275                     280                     285

AAG TTT AAA GAT ATA GCA AGT ACA CTT AAT AAA GCT AAA TCA ATA GTA          912
Lys Phe Lys Asp Ile Ala Ser Thr Leu Asn Lys Ala Lys Ser Ile Val
290                     295                     300

GGT ACT ACT GCT TCA TTA CAG TAT ATG AAA AAT GTT TTT AAA GAG AAA          960
Gly Thr Thr Ala Ser Leu Gln Tyr Met Lys Asn Val Phe Lys Glu Lys
305                     310                     315                     320

TAT CTC CTA TCT GAA GAT ACA TCT GGA AAA TTT TCG GTA GAT AAA TTA         1008
Tyr Leu Leu Ser Glu Asp Thr Ser Gly Lys Phe Ser Val Asp Lys Leu
                    325                     330                     335

AAA TTT GAT AAG TTA TAC AAA ATG TTA ACA GAG ATT TAC ACA GAG GAT         1056
Lys Phe Asp Lys Leu Tyr Lys Met Leu Thr Glu Ile Tyr Thr Glu Asp
                340                     345                     350

AAT TTT GTT AAG TTT TTT AAA GTA CTT AAC AGA AAA ACA TAT TTG AAT         1104
Asn Phe Val Lys Phe Phe Lys Val Leu Asn Arg Lys Thr Tyr Leu Asn
                355                     360                     365

TTT GAT AAA GCC GTA TTT AAG ATA AAT ATA GTA CCT AAG GTA AAT TAC         1152
Phe Asp Lys Ala Val Phe Lys Ile Asn Ile Val Pro Lys Val Asn Tyr
        370                     375                     380

ACA ATA TAT GAT GGA TTT AAT TTA AGA AAT ACA AAT TTA GCA GCA AAC         1200
Thr Ile Tyr Asp Gly Phe Asn Leu Arg Asn Thr Asn Leu Ala Ala Asn
385                     390                     395                     400

TTT AAT GGT CAA AAT ACA GAA ATT AAT AAT ATG AAT TTT ACT AAA CTA         1248
Phe Asn Gly Gln Asn Thr Glu Ile Asn Asn Met Asn Phe Thr Lys Leu
                    405                     410                     415

AAA AAT TTT ACT GGA TTG TTT GAA TTT TAT AAG TTG CTA TGT GTA AGA         1296
Lys Asn Phe Thr Gly Leu Phe Glu Phe Tyr Lys Leu Leu Cys Val Arg
                420                     425                     430

GGG ATA ATA ACT TCT AAA ACT AAA TCA TTA GAT AAA GGA TAC AAT AAG         1344
Gly Ile Ile Thr Ser Lys Thr Lys Ser Leu Asp Lys Gly Tyr Asn Lys
                435                     440                     445

GCA TTA AAT GAT TTA TGT ATC AAA GTT AAT AAT TGG GAC TTG TTT TTT         1392
Ala Leu Asn Asp Leu Cys Ile Lys Val Asn Asn Trp Asp Leu Phe Phe
450                     455                     460

AGT CCT TCA GAA GAT AAT TTT ACT AAT GAT CTA AAT AAA GGA GAA GAA         1440
```

```
                        -continued

Ser Pro Ser Glu Asp Asn Phe Thr Asn Asp Leu Asn Lys Gly Glu Glu
465                 470                 475                 480

ATT ACA TCT GAT ACT AAT ATA GAA GCA GCA GAA GAA AAT ATT AGT TTA      1488
Ile Thr Ser Asp Thr Asn Ile Glu Ala Ala Glu Glu Asn Ile Ser Leu
                485                 490                 495

GAT TTA ATA CAA CAA TAT TAT TTA ACC TTT AAT TTT GAT AAT GAA CCT      1536
Asp Leu Ile Gln Gln Tyr Tyr Leu Thr Phe Asn Phe Asp Asn Glu Pro
                500                 505                 510

GAA AAT ATT TCA ATA GAA AAT CTT TCA AGT GAC ATT ATA GGC CAA TTA      1584
Glu Asn Ile Ser Ile Glu Asn Leu Ser Ser Asp Ile Ile Gly Gln Leu
                515                 520                 525

GAA CTT ATG CCT AAT ATA GAA AGA TTT CCT AAT GGA AAA AAG TAT GAG      1632
Glu Leu Met Pro Asn Ile Glu Arg Phe Pro Asn Gly Lys Lys Tyr Glu
530                 535                 540

TTA GAT AAA TAT ACT ATG TTC CAT TAT CTT CGT GCT CAA GAA TTT GAA      1680
Leu Asp Lys Tyr Thr Met Phe His Tyr Leu Arg Ala Gln Glu Phe Glu
545                 550                 555                 560

CAT GGT AAA TCT AGG ATT GCT TTA ACA AAT TCT GTT AAC GAA GCA TTA      1728
His Gly Lys Ser Arg Ile Ala Leu Thr Asn Ser Val Asn Glu Ala Leu
                565                 570                 575

TTA AAT CCT AGT CGT GTT TAT ACA TTT TTT TCT TCA GAC TAT GTA AAG      1776
Leu Asn Pro Ser Arg Val Tyr Thr Phe Phe Ser Ser Asp Tyr Val Lys
                580                 585                 590

AAA GTT AAT AAA GCT ACG GAG GCA GCT ATG TTT TTA GGC TGG GTA GAA      1824
Lys Val Asn Lys Ala Thr Glu Ala Ala Met Phe Leu Gly Trp Val Glu
                595                 600                 605

CAA TTA GTA TAT GAT TTT ACC GAT GAA ACT AGC GAA GTA AGT ACT ACG      1872
Gln Leu Val Tyr Asp Phe Thr Asp Glu Thr Ser Glu Val Ser Thr Thr
610                 615                 620

GAT AAA ATT GCG GAT ATA ACT ATA ATT ATT CCA TAT ATA GGA CCT GCT      1920
Asp Lys Ile Ala Asp Ile Thr Ile Ile Ile Pro Tyr Ile Gly Pro Ala
625                 630                 635                 640

TTA AAT ATA GGT AAT ATG TTA TAT AAA GAT GAT TTT GTA GGT GCT TTA      1968
Leu Asn Ile Gly Asn Met Leu Tyr Lys Asp Asp Phe Val Gly Ala Leu
                645                 650                 655

ATA TTT TCA GGA GCT GTT ATT CTG TTA GAA TTT ATA CCA GAG ATT GCA      2016
Ile Phe Ser Gly Ala Val Ile Leu Leu Glu Phe Ile Pro Glu Ile Ala
                660                 665                 670

ATA CCT GTA TTA GGT ACT TTT GCA CTT GTA TCA TAT ATT GCG AAT AAG      2064
Ile Pro Val Leu Gly Thr Phe Ala Leu Val Ser Tyr Ile Ala Asn Lys
                675                 680                 685

GTT CTA ACC GTT CAA ACA ATA GAT AAT GCT TTA AGT AAA AGA AAT GAA      2112
Val Leu Thr Val Gln Thr Ile Asp Asn Ala Leu Ser Lys Arg Asn Glu
                690                 695                 700

AAA TGG GAT GAG GTC TAT AAA TAT ATA GTA ACA AAT TGG TTA GCA AAG      2160
Lys Trp Asp Glu Val Tyr Lys Tyr Ile Val Thr Asn Trp Leu Ala Lys
705                 710                 715                 720

GTT AAT ACA CAG ATT GAT CTA ATA AGA AAA AAA ATG AAA GAA GCT TTA      2208
Val Asn Thr Gln Ile Asp Leu Ile Arg Lys Lys Met Lys Glu Ala Leu
                725                 730                 735

GAA AAT CAA GCA GAA GCA ACA AAG GCT ATA ATA AAC TAT CAG TAT AAT      2256
Glu Asn Gln Ala Glu Ala Thr Lys Ala Ile Ile Asn Tyr Gln Tyr Asn
                740                 745                 750

CAA TAT ACT GAG GAA GAG AAA AAT AAT ATT AAT TTT AAT ATT GAT GAT      2304
Gln Tyr Thr Glu Glu Glu Lys Asn Asn Ile Asn Phe Asn Ile Asp Asp
                755                 760                 765

TTA AGT TCG AAA CTT AAT GAG TCT ATA AAT AAA GCT ATG ATT AAT ATA      2352
Leu Ser Ser Lys Leu Asn Glu Ser Ile Asn Lys Ala Met Ile Asn Ile
                770                 775                 780
```

-continued

```
AAT AAA TTT TTG AAT CAA TGC TCT GTT TCA TAT TTA ATG AAT TCT ATG      2400
Asn Lys Phe Leu Asn Gln Cys Ser Val Ser Tyr Leu Met Asn Ser Met
785                 790                 795                 800

ATC CCT TAT GGT GTT AAA CGG TTA GAA GAT TTT GAT GCT AGT CTT AAA      2448
Ile Pro Tyr Gly Val Lys Arg Leu Glu Asp Phe Asp Ala Ser Leu Lys
            805                 810                 815

GAT GCA TTA TTA AAG TAT ATA TAT GAT AAT AGA GGA ACT TTA ATT GGT      2496
Asp Ala Leu Leu Lys Tyr Ile Tyr Asp Asn Arg Gly Thr Leu Ile Gly
        820                 825                 830

CAA GTA GAT AGA TTA AAA GAT AAA GTT AAT AAT ACA CTT AGT ACA GAT      2544
Gln Val Asp Arg Leu Lys Asp Lys Val Asn Asn Thr Leu Ser Thr Asp
    835                 840                 845

ATA CCT TTT CAG CTT TCC AAA TAC GTA GAT AAT CAA AGA TTA TTA TCT      2592
Ile Pro Phe Gln Leu Ser Lys Tyr Val Asp Asn Gln Arg Leu Leu Ser
850                 855                 860

ACA TTT ACT GAA TAT ATT AAG                                          2613
Thr Phe Thr Glu Tyr Ile Lys
865                 870
```

(2) INFORMATION FOR SEQ ID NO: 8:

(i) SEQUENCE CHARACTERISTICS:
        (A) LENGTH: 871 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
```

```
                225                 230                 235                 240
Arg Val Phe Lys Val Asn Thr Asn Ala Tyr Tyr Glu Met Ser Gly Leu
                    245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
                290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                    325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
            370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                    405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
                435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                    485                 490                 495
Asp Leu Ile Gln Gln Tyr Tyr Leu Thr Phe Asn Phe Asp Asn Glu Pro
                500                 505                 510
Glu Asn Ile Ser Ile Glu Asn Leu Ser Ser Asp Ile Ile Gly Gln Leu
                515                 520                 525
Glu Leu Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                    565                 570                 575
Leu Asn Pro Ser Arg Val Tyr Thr Phe Phe Ser Ser Asp Tyr Val Lys
                580                 585                 590
Lys Val Asn Lys Ala Thr Glu Ala Ala Met Phe Leu Gly Trp Val Glu
                595                 600                 605
Gln Leu Val Tyr Asp Phe Thr Asp Glu Thr Ser Glu Val Ser Thr Thr
            610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                    645                 650                 655
```

```
Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
            770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
            850                 855                 860

Thr Phe Thr Glu Tyr Ile Lys
865                 870

(2) INFORMATION FOR SEQ ID NO: 9:

(i) SEQUENCE CHARACTERISTICS:
        (A) LENGTH: 2628 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2628

(xi) SEQUENCE DESCRIPTION: SEQ ID NO: 9:

ATG CAG TTC GTG AAC AAG CAG TTC AAC TAT AAG GAC CCT GTA AAC GGT      48
Met Gln Phe Val Asn Lys Gln Phe Asn Tyr Lys Asp Pro Val Asn Gly
1               5                   10                  15

GTT GAC ATT GCC TAC ATC AAA ATT CCA AAC GCC GGC CAG ATG CAG CCG      96
Val Asp Ile Ala Tyr Ile Lys Ile Pro Asn Ala Gly Gln Met Gln Pro
                20                  25                  30

GTG AAG GCT TTC AAG ATT CAT AAC AAA ATC TGG GTT ATT CCG GAA CGC     144
Val Lys Ala Phe Lys Ile His Asn Lys Ile Trp Val Ile Pro Glu Arg
            35                  40                  45

GAT ACA TTT ACG AAC CCG GAA GAA GGA GAC TTG AAC CCG CCG CCG GAA     192
Asp Thr Phe Thr Asn Pro Glu Glu Gly Asp Leu Asn Pro Pro Pro Glu
        50                  55                  60

GCA AAG CAG GTG CCA GTT TCA TAC TAC GAT TCA ACC TAT CTG AGC ACA     240
Ala Lys Gln Val Pro Val Ser Tyr Tyr Asp Ser Thr Tyr Leu Ser Thr
65                  70                  75                  80
```

```
GAC AAC GAG AAG GAT AAC TAC CTG AAG GGA GTG ACC AAA TTA TTC GAG      288
Asp Asn Glu Lys Asp Asn Tyr Leu Lys Gly Val Thr Lys Leu Phe Glu
                 85                  90                  95

CGT ATT TAT TCC ACT GAC CTG GGC CGT ATG CTG CTG ACC TCA ATC GTC      336
Arg Ile Tyr Ser Thr Asp Leu Gly Arg Met Leu Leu Thr Ser Ile Val
            100                 105                 110

CGC GGA ATC CCA TTT TGG GGT GGC AGT ACC ATT GAC ACG GAG TTG AAG      384
Arg Gly Ile Pro Phe Trp Gly Gly Ser Thr Ile Asp Thr Glu Leu Lys
        115                 120                 125

GTT ATT GAC ACT AAC TGC ATT AAC GTG ATC CAA CCA GAC GGT AGC TAC      432
Val Ile Asp Thr Asn Cys Ile Asn Val Ile Gln Pro Asp Gly Ser Tyr
    130                 135                 140

AGA TCT GAA GAA CTT AAC CTC GTA ATC ATC GGG CCC TCC GCG GAC ATT      480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG      528
Ile Gln Phe Glu Cys Lys Ser Phe Gly His Glu Val Leu Asn Leu Thr
                165                 170                 175

CGT AAC GGT TAC GGC TCT ACT CAG TAC ATT CGT TTC AGC CCA GAC TTC      576
Arg Asn Gly Tyr Gly Ser Thr Gln Tyr Ile Arg Phe Ser Pro Asp Phe
            180                 185                 190

ACG TTC GGT TTC GAG GAG AGC CTG GAG GTT GAT ACC AAC CCG CTG TTG      624
Thr Phe Gly Phe Glu Glu Ser Leu Glu Val Asp Thr Asn Pro Leu Leu
        195                 200                 205

GGT GCA GGC AAG TTC GCA ACT GAT CCA GCG GTG ACC CTG GCA CAC GAG      672
Gly Ala Gly Lys Phe Ala Thr Asp Pro Ala Val Thr Leu Ala His Glu
    210                 215                 220

CTG ATC CAC GCC GGT CAT CGT CTG TAT GGC ATT GCG ATT AAC CCG AAC      720
Leu Ile His Ala Gly His Arg Leu Tyr Gly Ile Ala Ile Asn Pro Asn
225                 230                 235                 240

CGC GTG TTC AAG GTT AAC ACC AAC GCC TAC TAC GAG ATG AGT GGT TTA      768
Arg Val Phe Lys Val Asn Thr Asn Ala Tyr Tyr Glu Met Ser Gly Leu
                245                 250                 255

GAA GTA AGC TTC GAG GAA CTG CGC ACG TTC GGT GGC CAT GAT GCG AAG      816
Glu Val Ser Phe Glu Glu Leu Arg Thr Phe Gly Gly His Asp Ala Lys
            260                 265                 270

TTT ATC GAC AGC TTG CAG GAG AAC GAG TTC CGT CTG TAC TAC TAC AAC      864
Phe Ile Asp Ser Leu Gln Glu Asn Glu Phe Arg Leu Tyr Tyr Tyr Asn
        275                 280                 285

AAG TTT AAA GAT ATT GCA AGT ACA CTG AAC AAG GCT AAG TCC ATT GTG      912
Lys Phe Lys Asp Ile Ala Ser Thr Leu Asn Lys Ala Lys Ser Ile Val
    290                 295                 300

GGT ACC ACT GCT TCA TTA CAG TAT ATG AAA AAT GTT TTT AAA GAG AAA      960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA     1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT     1056
Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT     1104
Asn Phe Val Lys Phe Phe Lys Val Leu Asn Arg Lys Thr Tyr Leu Asn
        355                 360                 365

TTT GAT AAA GCC GTA TTT AAG ATA AAT ATA GTA CCT AAG GTA AAT TAC     1152
Phe Asp Lys Ala Val Phe Lys Ile Asn Ile Val Pro Lys Val Asn Tyr
    370                 375                 380

ACA ATA TAT GAT GGA TTT AAT TTA AGA AAT ACA AAT TTA GCA GCA AAC     1200
Thr Ile Tyr Asp Gly Phe Asn Leu Arg Asn Thr Asn Leu Ala Ala Asn
```

```
                -continued 385                390                395                400
TTT AAT GGT CAA AAT ACA GAA ATT AAT AAT ATG AAT TTT ACT AAA CTA    1248
Phe Asn Gly Gln Asn Thr Glu Ile Asn Asn Met Asn Phe Thr Lys Leu
                405                410                415

AAA AAT TTT ACT GGA TTG TTT GAA TTT TAT AAG TTG CTA TGT GTA AGA    1296
Lys Asn Phe Thr Gly Leu Phe Glu Phe Tyr Lys Leu Leu Cys Val Arg
                420                425                430

GGG ATA ATA ACT TCT AAA ACT AAA TCA TTA GAT AAA GGA TAC AAT AAG    1344
Gly Ile Ile Thr Ser Lys Thr Lys Ser Leu Asp Lys Gly Tyr Asn Lys
                435                440                445

AGC GCT GAT GGG GCA TTA AAT GAT TTA TGT ATC AAA GTT AAT AAT TGG    1392
Ser Ala Asp Gly Ala Leu Asn Asp Leu Cys Ile Lys Val Asn Asn Trp
    450                455                460

GAC TTG TTT TTT AGT CCT TCA GAA GAT AAT TTT ACT AAT GAT CTA AAT    1440
Asp Leu Phe Phe Ser Pro Ser Glu Asp Asn Phe Thr Asn Asp Leu Asn
465                470                475                480

AAA GGA GAA GAA ATT ACA TCT GAT ACT AAT ATA GAA GCA GCA GAA GAA    1488
Lys Gly Glu Glu Ile Thr Ser Asp Thr Asn Ile Glu Ala Ala Glu Glu
                485                490                495

AAT ATT AGT TTA GAT TTA ATA CAA CAA TAT TAT TTA ACC TTT AAT TTT    1536
Asn Ile Ser Leu Asp Leu Ile Gln Gln Tyr Tyr Leu Thr Phe Asn Phe
                500                505                510

GAT AAT GAA CCT GAA AAT ATT TCA ATA GAA AAT CTT TCA AGT GAC ATT    1584
Asp Asn Glu Pro Glu Asn Ile Ser Ile Glu Asn Leu Ser Ser Asp Ile
                515                520                525

ATA GGC CAA TTA GAA CTT ATG CCT AAT ATA GAA AGA TTT CCT AAT GGA    1632
Ile Gly Gln Leu Glu Leu Met Pro Asn Ile Glu Arg Phe Pro Asn Gly
    530                535                540

AAA AAG TAT GAG TTA GAT AAA TAT ACT ATG TTC CAT TAT CTT CGT GCT    1680
Lys Lys Tyr Glu Leu Asp Lys Tyr Thr Met Phe His Tyr Leu Arg Ala
545                550                555                560

CAA GAA TTT GAA CAT GGT AAA TCT AGG ATT GCT TTA ACA AAT TCT GTT    1728
Gln Glu Phe Glu His Gly Lys Ser Arg Ile Ala Leu Thr Asn Ser Val
                565                570                575

AAC GAA GCA TTA TTA AAT CCT AGT CGT GTT TAT ACA TTT TTT TCT TCA    1776
Asn Glu Ala Leu Leu Asn Pro Ser Arg Val Tyr Thr Phe Phe Ser Ser
                580                585                590

GAC TAT GTA AAG AAA GTT AAT AAA GCT ACG GAG GCA GCT ATG TTT TTA    1824
Asp Tyr Val Lys Lys Val Asn Lys Ala Thr Glu Ala Ala Met Phe Leu
                595                600                605

GGC TGG GTA GAA CAA TTA GTA TAT GAT TTT ACC GAT GAA ACT AGC GAA    1872
Gly Trp Val Glu Gln Leu Val Tyr Asp Phe Thr Asp Glu Thr Ser Glu
    610                615                620

GTA AGT ACT ACG GAT AAA ATT GCG GAT ATA ACT ATA ATT ATT CCA TAT    1920
Val Ser Thr Thr Asp Lys Ile Ala Asp Ile Thr Ile Ile Ile Pro Tyr
625                630                635                640

ATA GGA CCT GCT TTA AAT ATA GGT AAT ATG TTA TAT AAA GAT GAT TTT    1968
Ile Gly Pro Ala Leu Asn Ile Gly Asn Met Leu Tyr Lys Asp Asp Phe
                645                650                655

GTA GGT GCT TTA ATA TTT TCA GGA GCT GTT ATT CTG TTA GAA TTT ATA    2016
Val Gly Ala Leu Ile Phe Ser Gly Ala Val Ile Leu Leu Glu Phe Ile
                660                665                670

CCA GAG ATT GCA ATA CCT GTA TTA GGT ACT TTT GCA CTT GTA TCA TAT    2064
Pro Glu Ile Ala Ile Pro Val Leu Gly Thr Phe Ala Leu Val Ser Tyr
                675                680                685

ATT GCG AAT AAG GTT CTA ACC GTT CAA ACA ATA GAT AAT GCT TTA AGT    2112
Ile Ala Asn Lys Val Leu Thr Val Gln Thr Ile Asp Asn Ala Leu Ser
                690                695                700

AAA AGA AAT GAA AAA TGG GAT GAG GTC TAT AAA TAT ATA GTA ACA AAT    2160
```

```
Lys Arg Asn Glu Lys Trp Asp Glu Val Tyr Lys Tyr Ile Val Thr Asn
705                 710                 715                 720

TGG TTA GCA AAG GTT AAT ACA CAG ATT GAT CTA ATA AGA AAA AAA ATG    2208
Trp Leu Ala Lys Val Asn Thr Gln Ile Asp Leu Ile Arg Lys Lys Met
                725                 730                 735

AAA GAA GCT TTA GAA AAT CAA GCA GAA GCA ACA AAG GCT ATA ATA AAC    2256
Lys Glu Ala Leu Glu Asn Gln Ala Glu Ala Thr Lys Ala Ile Ile Asn
                740                 745                 750

TAT CAG TAT AAT CAA TAT ACT GAG GAA GAG AAA AAT AAT ATT AAT TTT    2304
Tyr Gln Tyr Asn Gln Tyr Thr Glu Glu Glu Lys Asn Asn Ile Asn Phe
                755                 760                 765

AAT ATT GAT GAT TTA AGT TCG AAA CTT AAT GAG TCT ATA AAT AAA GCT    2352
Asn Ile Asp Asp Leu Ser Ser Lys Leu Asn Glu Ser Ile Asn Lys Ala
770                 775                 780

ATG ATT AAT ATA AAT AAA TTT TTG AAT CAA TGC TCT GTT TCA TAT TTA    2400
Met Ile Asn Ile Asn Lys Phe Leu Asn Gln Cys Ser Val Ser Tyr Leu
785                 790                 795                 800

ATG AAT TCT ATG ATC CCT TAT GGT GTT AAA CGG TTA GAA GAT TTT GAT    2448
Met Asn Ser Met Ile Pro Tyr Gly Val Lys Arg Leu Glu Asp Phe Asp
                805                 810                 815

GCT AGT CTT AAA GAT GCA TTA TTA AAG TAT ATA TAT GAT AAT AGA GGA    2496
Ala Ser Leu Lys Asp Ala Leu Leu Lys Tyr Ile Tyr Asp Asn Arg Gly
                820                 825                 830

ACT TTA ATT GGT CAA GTA GAT AGA TTA AAA GAT AAA GTT AAT AAT ACA    2544
Thr Leu Ile Gly Gln Val Asp Arg Leu Lys Asp Lys Val Asn Asn Thr
                835                 840                 845

CTT AGT ACA GAT ATA CCT TTT CAG CTT TCC AAA TAC GTA GAT AAT CAA    2592
Leu Ser Thr Asp Ile Pro Phe Gln Leu Ser Lys Tyr Val Asp Asn Gln
850                 855                 860

AGA TTA TTA TCT ACA TTT ACT GAA TAT ATT AAG TAA                   2628
Arg Leu Leu Ser Thr Phe Thr Glu Tyr Ile Lys
865                 870                 875

(2) INFORMATION FOR SEQ ID NO: 10:

(i) SEQUENCE CHARACTERISTICS:
        (A) LENGTH: 875 amino acids
        (B) TYPE: amino acid
        (D) TOPOLOGY: linear (ii) MOLECULE TYPE: protein (xi) SEQUENCE DESCRIPTION: SEQ ID NO: 10:

Met Gln Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
                35                  40                  45

Asp Thr Phe Thr Asn Pro Glu Glu Gly Asp Leu Asn Pro Pro Pro Glu
                50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
                115                 120                 125
```

```
Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ser Ala Asp Gly Ala Leu Asn Asp Leu Cys Ile Lys Val Asn Asn Trp
    450                 455                 460

Asp Leu Phe Phe Ser Pro Ser Glu Asp Asn Phe Thr Asn Asp Leu Asn
465                 470                 475                 480

Lys Gly Glu Glu Ile Thr Ser Asp Thr Asn Ile Glu Ala Ala Glu Glu
                485                 490                 495

Asn Ile Ser Leu Asp Leu Ile Gln Gln Tyr Tyr Leu Thr Phe Asn Phe
            500                 505                 510

Asp Asn Glu Pro Glu Asn Ile Ser Ile Glu Asn Leu Ser Ser Asp Ile
        515                 520                 525

Ile Gly Gln Leu Glu Leu Met Pro Asn Ile Glu Arg Phe Pro Asn Gly
    530                 535                 540

Lys Lys Tyr Glu Leu Asp Lys Tyr Thr Met Phe His Tyr Leu Arg Ala
```

-continued

```
                     545                 550                 555                 560
Gln Glu Phe Glu His Gly Lys Ser Arg Ile Ala Leu Thr Asn Ser Val
                565                 570                 575

Asn Glu Ala Leu Leu Asn Pro Ser Arg Val Tyr Thr Phe Phe Ser Ser
                580                 585                 590

Asp Tyr Val Lys Lys Val Asn Lys Ala Thr Glu Ala Ala Met Phe Leu
                595                 600                 605

Gly Trp Val Glu Gln Leu Val Tyr Asp Phe Thr Asp Glu Thr Ser Glu
                610                 615                 620

Val Ser Thr Thr Asp Lys Ile Ala Asp Ile Thr Ile Ile Pro Tyr
625                 630                 635                 640

Ile Gly Pro Ala Leu Asn Ile Gly Asn Met Leu Tyr Lys Asp Asp Phe
                645                 650                 655

Val Gly Ala Leu Ile Phe Ser Gly Ala Val Ile Leu Glu Phe Ile
                660                 665                 670

Pro Glu Ile Ala Ile Pro Val Leu Gly Thr Phe Ala Leu Val Ser Tyr
                675                 680                 685

Ile Ala Asn Lys Val Leu Thr Val Gln Thr Ile Asp Asn Ala Leu Ser
                690                 695                 700

Lys Arg Asn Glu Lys Trp Asp Glu Val Tyr Lys Tyr Ile Val Thr Asn
705                 710                 715                 720

Trp Leu Ala Lys Val Asn Thr Gln Ile Asp Leu Ile Arg Lys Lys Met
                725                 730                 735

Lys Glu Ala Leu Glu Asn Gln Ala Glu Ala Thr Lys Ala Ile Ile Asn
                740                 745                 750

Tyr Gln Tyr Asn Gln Tyr Thr Glu Glu Glu Lys Asn Asn Ile Asn Phe
                755                 760                 765

Asn Ile Asp Asp Leu Ser Ser Lys Leu Asn Glu Ser Ile Asn Lys Ala
                770                 775                 780

Met Ile Asn Ile Asn Lys Phe Leu Asn Gln Cys Ser Val Ser Tyr Leu
785                 790                 795                 800

Met Asn Ser Met Ile Pro Tyr Gly Val Lys Arg Leu Glu Asp Phe Asp
                805                 810                 815

Ala Ser Leu Lys Asp Ala Leu Leu Lys Tyr Ile Tyr Asp Asn Arg Gly
                820                 825                 830

Thr Leu Ile Gly Gln Val Asp Arg Leu Lys Asp Lys Val Asn Asn Thr
                835                 840                 845

Leu Ser Thr Asp Ile Pro Phe Gln Leu Ser Lys Tyr Val Asp Asn Gln
850                 855                 860

Arg Leu Leu Ser Thr Phe Thr Glu Tyr Ile Lys
865                 870                 875
```

(2) INFORMATION FOR SEQ ID NO: 11:

(i) SEQUENCE CHARACTERISTICS:
        (A) LENGTH: 2637 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2637

(xi) SEQUENCE DESCRIPTION: SEQ ID NO: 11:

```
ATG CAG TTC GTG AAC AAG CAG TTC AAC TAT AAG GAC CCT GTA AAC GGT        48
Met Gln Phe Val Asn Lys Gln Phe Asn Tyr Lys Asp Pro Val Asn Gly
  1               5                  10                  15

GTT GAC ATT GCC TAC ATC AAA ATT CCA AAC GCC GGC CAG ATG CAG CCG        96
Val Asp Ile Ala Tyr Ile Lys Ile Pro Asn Ala Gly Gln Met Gln Pro
                 20                  25                  30

GTG AAG GCT TTC AAG ATT CAT AAC AAA ATC TGG GTT ATT CCG GAA CGC       144
Val Lys Ala Phe Lys Ile His Asn Lys Ile Trp Val Ile Pro Glu Arg
             35                  40                  45

GAT ACA TTT ACG AAC CCG GAA GAA GGA GAC TTG AAC CCG CCG CCG GAA       192
Asp Thr Phe Thr Asn Pro Glu Glu Gly Asp Leu Asn Pro Pro Pro Glu
         50                  55                  60

GCA AAG CAG GTG CCA GTT TCA TAC TAC GAT TCA ACC TAT CTG AGC ACA       240
Ala Lys Gln Val Pro Val Ser Tyr Tyr Asp Ser Thr Tyr Leu Ser Thr
 65                  70                  75                  80

GAC AAC GAG AAG GAT AAC TAC CTG AAG GGA GTG ACC AAA TTA TTC GAG       288
Asp Asn Glu Lys Asp Asn Tyr Leu Lys Gly Val Thr Lys Leu Phe Glu
                 85                  90                  95

CGT ATT TAT TCC ACT GAC CTG GGC CGT ATG CTG CTG ACC TCA ATC GTC       336
Arg Ile Tyr Ser Thr Asp Leu Gly Arg Met Leu Leu Thr Ser Ile Val
             100                 105                 110

CGC GGA ATC CCA TTT TGG GGT GGC AGT ACC ATT GAC ACG GAG TTG AAG       384
Arg Gly Ile Pro Phe Trp Gly Gly Ser Thr Ile Asp Thr Glu Leu Lys
         115                 120                 125

GTT ATT GAC ACT AAC TGC ATT AAC GTG ATC CAA CCA GAC GGT AGC TAC       432
Val Ile Asp Thr Asn Cys Ile Asn Val Ile Gln Pro Asp Gly Ser Tyr
 130                 135                 140

AGA TCT GAA GAA CTT AAC CTC GTA ATC ATC GGG CCC TCC GCG GAC ATT       480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG       528
Ile Gln Phe Glu Cys Lys Ser Phe Gly His Glu Val Leu Asn Leu Thr
                 165                 170                 175

CGT AAC GGT TAC GGC TCT ACT CAG TAC ATT CGT TTC AGC CCA GAC TTC       576
Arg Asn Gly Tyr Gly Ser Thr Gln Tyr Ile Arg Phe Ser Pro Asp Phe
             180                 185                 190

ACG TTC GGT TTC GAG GAG AGC CTG GAG GTT GAT ACC AAC CCG CTG TTG       624
Thr Phe Gly Phe Glu Glu Ser Leu Glu Val Asp Thr Asn Pro Leu Leu
         195                 200                 205

GGT GCA GGC AAG TTC GCA ACT GAT CCA GCG GTG ACC CTG GCA CAC GAG       672
Gly Ala Gly Lys Phe Ala Thr Asp Pro Ala Val Thr Leu Ala His Glu
 210                 215                 220

CTG ATC CAC GCC GGT CAT CGT CTG TAT GGC ATT GCG ATT AAC CCG AAC       720
Leu Ile His Ala Gly His Arg Leu Tyr Gly Ile Ala Ile Asn Pro Asn
225                 230                 235                 240

CGC GTG TTC AAG GTT AAC ACC AAC GCC TAC TAC GAG ATG AGT GGT TTA       768
Arg Val Phe Lys Val Asn Thr Asn Ala Tyr Tyr Glu Met Ser Gly Leu
                 245                 250                 255

GAA GTA AGC TTC GAG GAA CTG CGC ACG TTC GGT GGC CAT GAT GCG AAG       816
Glu Val Ser Phe Glu Glu Leu Arg Thr Phe Gly Gly His Asp Ala Lys
             260                 265                 270

TTT ATC GAC AGC TTG CAG GAG AAC GAG TTC CGT CTG TAC TAC TAC AAC       864
Phe Ile Asp Ser Leu Gln Glu Asn Glu Phe Arg Leu Tyr Tyr Tyr Asn
         275                 280                 285

AAG TTT AAA GAT ATT GCA AGT ACA CTG AAC AAG GCT AAG TCC ATT GTG       912
Lys Phe Lys Asp Ile Ala Ser Thr Leu Asn Lys Ala Lys Ser Ile Val
 290                 295                 300

GGT ACC ACT GCT TCA TTA CAG TAT ATG AAA AAT GTT TTT AAA GAG AAA       960
Gly Thr Thr Ala Ser Leu Gln Tyr Met Lys Asn Val Phe Lys Glu Lys
305                 310                 315                 320
```

```
TAT CTC CTA TCT GAA GAT ACA TCT GGA AAA TTT TCG GTA GAT AAA TTA        1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT        1056
Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT        1104
Asn Phe Val Lys Phe Phe Lys Val Leu Asn Arg Lys Thr Tyr Leu Asn
        355                 360                 365

TTT GAT AAA GCC GTA TTT AAG ATA AAT ATA GTA CCT AAG GTA AAT TAC        1152
Phe Asp Lys Ala Val Phe Lys Ile Asn Ile Val Pro Lys Val Asn Tyr
    370                 375                 380

ACA ATA TAT GAT GGA TTT AAT TTA AGA AAT ACA AAT TTA GCA GCA AAC        1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA        1248
Phe Asn Gly Gln Asn Thr Glu Ile Asn Asn Met Asn Phe Thr Lys Leu
                405                 410                 415

AAA AAT TTT ACT GGA TTG TTT GAA TTT TAT AAG TTG CTA TGT GTA AGA        1296
Lys Asn Phe Thr Gly Leu Phe Glu Phe Tyr Lys Leu Leu Cys Val Arg
            420                 425                 430

GGG ATA ATA ACT TCT AAA ACT AAA TCA TTA GAT AAA GGA TAC AAT AAG        1344
Gly Ile Ile Thr Ser Lys Thr Lys Ser Leu Asp Lys Gly Tyr Asn Lys
        435                 440                 445

ATC GAA GGT CGT TGC GAT GGG GCA TTA AAT GAT TTA TGT ATC AAA GTT        1392
Ile Glu Gly Arg Cys Asp Gly Ala Leu Asn Asp Leu Cys Ile Lys Val
    450                 455                 460

AAT AAT TGG GAC TTG TTT TTT AGT CCT TCA GAA GAT AAT TTT ACT AAT        1440
Asn Asn Trp Asp Leu Phe Phe Ser Pro Ser Glu Asp Asn Phe Thr Asn
465                 470                 475                 480

GAT CTA AAT AAA GGA GAA GAA ATT ACA TCT GAT ACT AAT ATA GAA GCA        1488
Asp Leu Asn Lys Gly Glu Glu Ile Thr Ser Asp Thr Asn Ile Glu Ala
                485                 490                 495

GCA GAA GAA AAT ATT AGT TTA GAT TTA ATA CAA CAA TAT TAT TTA ACC        1536
Ala Glu Glu Asn Ile Ser Leu Asp Leu Ile Gln Gln Tyr Tyr Leu Thr
            500                 505                 510

TTT AAT TTT GAT AAT GAA CCT GAA AAT ATT TCA ATA GAA AAT CTT TCA        1584
Phe Asn Phe Asp Asn Glu Pro Glu Asn Ile Ser Ile Glu Asn Leu Ser
        515                 520                 525

AGT GAC ATT ATA GGC CAA TTA GAA CTT ATG CCT AAT ATA GAA AGA TTT        1632
Ser Asp Ile Ile Gly Gln Leu Glu Leu Met Pro Asn Ile Glu Arg Phe
    530                 535                 540

CCT AAT GGA AAA AAG TAT GAG TTA GAT AAA TAT ACT ATG TTC CAT TAT        1680
Pro Asn Gly Lys Lys Tyr Glu Leu Asp Lys Tyr Thr Met Phe His Tyr
545                 550                 555                 560

CTT CGT GCT CAA GAA TTT GAA CAT GGT AAA TCT AGG ATT GCT TTA ACA        1728
Leu Arg Ala Gln Glu Phe Glu His Gly Lys Ser Arg Ile Ala Leu Thr
                565                 570                 575

AAT TCT GTT AAC GAA GCA TTA TTA AAT CCT AGT CGT GTT TAT ACA TTT        1776
Asn Ser Val Asn Glu Ala Leu Leu Asn Pro Ser Arg Val Tyr Thr Phe
            580                 585                 590

TTT TCT TCA GAC TAT GTA AAG AAA GTT AAT AAA GCT ACG GAG GCA GCT        1824
Phe Ser Ser Asp Tyr Val Lys Lys Val Asn Lys Ala Thr Glu Ala Ala
        595                 600                 605

ATG TTT TTA GGC TGG GTA GAA CAA TTA GTA TAT GAT TTT ACC GAT GAA        1872
Met Phe Leu Gly Trp Val Glu Gln Leu Val Tyr Asp Phe Thr Asp Glu
    610                 615                 620

ACT AGC GAA GTA AGT ACT ACG GAT AAA ATT GCG GAT ATA ACT ATA ATT        1920
Thr Ser Glu Val Ser Thr Thr Asp Lys Ile Ala Asp Ile Thr Ile Ile
```

-continued

```
        625                 630                 635                 640
ATT CCA TAT ATA GGA CCT GCT TTA AAT ATA GGT AAT ATG TTA TAT AAA                     1968
Ile Pro Tyr Ile Gly Pro Ala Leu Asn Ile Gly Asn Met Leu Tyr Lys
                    645                 650                 655

GAT GAT TTT GTA GGT GCT TTA ATA TTT TCA GGA GCT GTT ATT CTG TTA                     2016
Asp Asp Phe Val Gly Ala Leu Ile Phe Ser Gly Ala Val Ile Leu Leu
                660                 665                 670

GAA TTT ATA CCA GAG ATT GCA ATA CCT GTA TTA GGT ACT TTT GCA CTT                     2064
Glu Phe Ile Pro Glu Ile Ala Ile Pro Val Leu Gly Thr Phe Ala Leu
                675                 680                 685

GTA TCA TAT ATT GCG AAT AAG GTT CTA ACC GTT CAA ACA ATA GAT AAT                     2112
Val Ser Tyr Ile Ala Asn Lys Val Leu Thr Val Gln Thr Ile Asp Asn
            690                 695                 700

GCT TTA AGT AAA AGA AAT GAA AAA TGG GAT GAG GTC TAT AAA TAT ATA                     2160
Ala Leu Ser Lys Arg Asn Glu Lys Trp Asp Glu Val Tyr Lys Tyr Ile
705                 710                 715                 720

GTA ACA AAT TGG TTA GCA AAG GTT AAT ACA CAG ATT GAT CTA ATA AGA                     2208
Val Thr Asn Trp Leu Ala Lys Val Asn Thr Gln Ile Asp Leu Ile Arg
                725                 730                 735

AAA AAA ATG AAA GAA GCT TTA GAA AAT CAA GCA GAA GCA ACA AAG GCT                     2256
Lys Lys Met Lys Glu Ala Leu Glu Asn Gln Ala Glu Ala Thr Lys Ala
                740                 745                 750

ATA ATA AAC TAT CAG TAT AAT CAA TAT ACT GAG GAA GAG AAA AAT AAT                     2304
Ile Ile Asn Tyr Gln Tyr Asn Gln Tyr Thr Glu Glu Glu Lys Asn Asn
                755                 760                 765

ATT AAT TTT AAT ATT GAT GAT TTA AGT TCG AAA CTT AAT GAG TCT ATA                     2352
Ile Asn Phe Asn Ile Asp Asp Leu Ser Ser Lys Leu Asn Glu Ser Ile
            770                 775                 780

AAT AAA GCT ATG ATT AAT ATA AAT AAA TTT TTG AAT CAA TGC TCT GTT                     2400
Asn Lys Ala Met Ile Asn Ile Asn Lys Phe Leu Asn Gln Cys Ser Val
785                 790                 795                 800

TCA TAT TTA ATG AAT TCT ATG ATC CCT TAT GGT GTT AAA CGG TTA GAA                     2448
Ser Tyr Leu Met Asn Ser Met Ile Pro Tyr Gly Val Lys Arg Leu Glu
                805                 810                 815

GAT TTT GAT GCT AGT CTT AAA GAT GCA TTA TTA AAG TAT ATA TAT GAT                     2496
Asp Phe Asp Ala Ser Leu Lys Asp Ala Leu Leu Lys Tyr Ile Tyr Asp
                820                 825                 830

AAT AGA GGA ACT TTA ATT GGT CAA GTA GAT AGA TTA AAA GAT AAA GTT                     2544
Asn Arg Gly Thr Leu Ile Gly Gln Val Asp Arg Leu Lys Asp Lys Val
                835                 840                 845

AAT AAT ACA CTT AGT ACA GAT ATA CCT TTT CAG CTT TCC AAA TAC GTA                     2592
Asn Asn Thr Leu Ser Thr Asp Ile Pro Phe Gln Leu Ser Lys Tyr Val
            850                 855                 860

GAT AAT CAA AGA TTA TTA TCT ACA TTT ACT GAA TAT ATT AAG TAA                         2637
Asp Asn Gln Arg Leu Leu Ser Thr Phe Thr Glu Tyr Ile Lys
865                 870                 875
```

(2) INFORMATION FOR SEQ ID NO: 12:

(i) SEQUENCE CHARACTERISTICS:
        (A) LENGTH: 878 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Gln Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30
```

-continued

```
Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Glu
         50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                     85                  90                  95

Arg Ile Tyr Ser Thr Asp Leu Gly Arg Met Leu Leu Thr Ser Ile Val
                 100                 105                 110

Arg Gly Ile Pro Phe Trp Gly Gly Ser Thr Ile Asp Thr Glu Leu Lys
             115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                 165                 170                 175

Arg Asn Gly Tyr Gly Ser Thr Gln Tyr Ile Arg Phe Ser Pro Asp Phe
             180                 185                 190

Thr Phe Gly Phe Glu Glu Ser Leu Glu Val Asp Thr Asn Pro Leu Leu
         195                 200                 205

Gly Ala Gly Lys Phe Ala Thr Asp Pro Ala Val Thr Leu Ala His Glu
         210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                 245                 250                 255

Glu Val Ser Phe Glu Glu Leu Arg Thr Phe Gly Gly His Asp Ala Lys
                 260                 265                 270

Phe Ile Asp Ser Leu Gln Glu Asn Glu Phe Arg Leu Tyr Tyr Tyr Asn
             275                 280                 285

Lys Phe Lys Asp Ile Ala Ser Thr Leu Asn Lys Ala Lys Ser Ile Val
         290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                 325                 330                 335

Lys Phe Asp Lys Leu Tyr Lys Met Leu Thr Glu Ile Tyr Thr Glu Asp
             340                 345                 350

Asn Phe Val Lys Phe Phe Lys Val Leu Asn Arg Lys Thr Tyr Leu Asn
         355                 360                 365

Phe Asp Lys Ala Val Phe Lys Ile Asn Ile Val Pro Lys Val Asn Tyr
         370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                 405                 410                 415

Lys Asn Phe Thr Gly Leu Phe Glu Phe Tyr Lys Leu Leu Cys Val Arg
                 420                 425                 430

Gly Ile Ile Thr Ser Lys Thr Lys Ser Leu Asp Lys Gly Tyr Asn Lys
             435                 440                 445
```

-continued

```
Ile Glu Gly Arg Cys Asp Gly Ala Leu Asn Asp Leu Cys Ile Lys Val
    450                 455                 460

Asn Asn Trp Asp Leu Phe Phe Ser Pro Ser Glu Asp Asn Phe Thr Asn
465                 470                 475                 480

Asp Leu Asn Lys Gly Glu Ile Thr Ser Asp Thr Asn Ile Glu Ala
                485                 490                 495

Ala Glu Glu Asn Ile Ser Leu Asp Leu Ile Gln Gln Tyr Tyr Leu Thr
            500                 505                 510

Phe Asn Phe Asp Asn Glu Pro Glu Asn Ile Ser Ile Glu Asn Leu Ser
            515                 520                 525

Ser Asp Ile Ile Gly Gln Leu Glu Leu Met Pro Asn Ile Glu Arg Phe
    530                 535                 540

Pro Asn Gly Lys Lys Tyr Glu Leu Asp Lys Tyr Thr Met Phe His Tyr
545                 550                 555                 560

Leu Arg Ala Gln Glu Phe Glu His Gly Lys Ser Arg Ile Ala Leu Thr
                565                 570                 575

Asn Ser Val Asn Glu Ala Leu Leu Asn Pro Ser Arg Val Tyr Thr Phe
            580                 585                 590

Phe Ser Ser Asp Tyr Val Lys Lys Val Asn Lys Ala Thr Glu Ala Ala
    595                 600                 605

Met Phe Leu Gly Trp Val Glu Gln Leu Val Tyr Asp Phe Thr Asp Glu
610                 615                 620

Thr Ser Glu Val Ser Thr Thr Asp Lys Ile Ala Asp Ile Thr Ile Ile
625                 630                 635                 640

Ile Pro Tyr Ile Gly Pro Ala Leu Asn Ile Gly Asn Met Leu Tyr Lys
                645                 650                 655

Asp Asp Phe Val Gly Ala Leu Ile Phe Ser Gly Ala Val Ile Leu Leu
            660                 665                 670

Glu Phe Ile Pro Glu Ile Ala Ile Pro Val Leu Gly Thr Phe Ala Leu
    675                 680                 685

Val Ser Tyr Ile Ala Asn Lys Val Leu Thr Val Gln Thr Ile Asp Asn
690                 695                 700

Ala Leu Ser Lys Arg Asn Glu Lys Trp Asp Glu Val Tyr Lys Tyr Ile
705                 710                 715                 720

Val Thr Asn Trp Leu Ala Lys Val Asn Thr Gln Ile Asp Leu Ile Arg
                725                 730                 735

Lys Lys Met Lys Glu Ala Leu Glu Asn Gln Ala Glu Ala Thr Lys Ala
            740                 745                 750

Ile Ile Asn Tyr Gln Tyr Asn Gln Tyr Thr Glu Glu Lys Asn Asn
    755                 760                 765

Ile Asn Phe Asn Ile Asp Asp Leu Ser Ser Lys Leu Asn Glu Ser Ile
770                 775                 780

Asn Lys Ala Met Ile Asn Ile Asn Lys Phe Leu Asn Gln Cys Ser Val
785                 790                 795                 800

Ser Tyr Leu Met Asn Ser Met Ile Pro Tyr Gly Val Lys Arg Leu Glu
                805                 810                 815

Asp Phe Asp Ala Ser Leu Lys Asp Ala Leu Leu Lys Tyr Ile Tyr Asp
            820                 825                 830

Asn Arg Gly Thr Leu Ile Gly Gln Val Asp Arg Leu Lys Asp Lys Val
    835                 840                 845

Asn Asn Thr Leu Ser Thr Asp Ile Pro Phe Gln Leu Ser Lys Tyr Val
850                 855                 860

Asp Asn Gln Arg Leu Leu Ser Thr Phe Thr Glu Tyr Ile Lys
```

-continued (2) INFORMATION FOR SEQ ID NO: 13:

(i) SEQUENCE CHARACTERISTICS:
        (A) LENGTH: 2862 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2862

(xi) SEQUENCE DESCRIPTION: SEQ ID NO: 13:

```
ATG CAG TTC GTG AAC AAG CAG TTC AAC TAT AAG GAC CCT GTA AAC GGT      48
Met Gln Phe Val Asn Lys Gln Phe Asn Tyr Lys Asp Pro Val Asn Gly
 1               5                  10                  15

GTT GAC ATT GCC TAC ATC AAA ATT CCA AAC GCC GGC CAG ATG CAG CCG      96
Val Asp Ile Ala Tyr Ile Lys Ile Pro Asn Ala Gly Gln Met Gln Pro
            20                  25                  30

GTG AAG GCT TTC AAG ATT CAT AAC AAA ATC TGG GTT ATT CCG GAA CGC     144
Val Lys Ala Phe Lys Ile His Asn Lys Ile Trp Val Ile Pro Glu Arg
        35                  40                  45

GAT ACA TTT ACG AAC CCG GAA GAA GGA GAC TTG AAC CCG CCG CCG GAA     192
Asp Thr Phe Thr Asn Pro Glu Glu Gly Asp Leu Asn Pro Pro Pro Glu
    50                  55                  60

GCA AAG CAG GTG CCA GTT TCA TAC TAC GAT TCA ACC TAT CTG AGC ACA     240
Ala Lys Gln Val Pro Val Ser Tyr Tyr Asp Ser Thr Tyr Leu Ser Thr
65                  70                  75                  80

GAC AAC GAG AAG GAT AAC TAC CTG AAG GGA GTG ACC AAA TTA TTC GAG     288
Asp Asn Glu Lys Asp Asn Tyr Leu Lys Gly Val Thr Lys Leu Phe Glu
                85                  90                  95

CGT ATT TAT TCC ACT GAC CTG GGC CGT ATG CTG CTG ACC TCA ATC GTC     336
Arg Ile Tyr Ser Thr Asp Leu Gly Arg Met Leu Leu Thr Ser Ile Val
            100                 105                 110

CGC GGA ATC CCA TTT TGG GGT GGC AGT ACC ATT GAC ACG GAG TTG AAG     384
Arg Gly Ile Pro Phe Trp Gly Gly Ser Thr Ile Asp Thr Glu Leu Lys
        115                 120                 125

GTT ATT GAC ACT AAC TGC ATT AAC GTG ATC CAA CCA GAC GGT AGC TAC     432
Val Ile Asp Thr Asn Cys Ile Asn Val Ile Gln Pro Asp Gly Ser Tyr
    130                 135                 140

AGA TCT GAA GAA CTT AAC CTC GTA ATC ATC GGG CCC TCC GCG GAC ATT     480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG     528
Ile Gln Phe Glu Cys Lys Ser Phe Gly His Glu Val Leu Asn Leu Thr
                165                 170                 175

CGT AAC GGT TAC GGC TCT ACT CAG TAC ATT CGT TTC AGC CCA GAC TTC     576
Arg Asn Gly Tyr Gly Ser Thr Gln Tyr Ile Arg Phe Ser Pro Asp Phe
            180                 185                 190

ACG TTC GGT TTC GAG GAG AGC CTG GAG GTT GAT ACC AAC CCG CTG TTG     624
Thr Phe Gly Phe Glu Glu Ser Leu Glu Val Asp Thr Asn Pro Leu Leu
        195                 200                 205

GGT GCA GGC AAG TTC GCA ACT GAT CCA GCG GTG ACC CTG GCA CAC GAG     672
Gly Ala Gly Lys Phe Ala Thr Asp Pro Ala Val Thr Leu Ala His Glu
    210                 215                 220

CTG ATC CAC GCC GGT CAT CGT CTG TAT GGC ATT GCG ATT AAC CCG AAC     720
Leu Ile His Ala Gly His Arg Leu Tyr Gly Ile Ala Ile Asn Pro Asn
225                 230                 235                 240
```

```
CGC GTG TTC AAG GTT AAC ACC AAC GCC TAC TAC GAG ATG AGT GGT TTA        768
Arg Val Phe Lys Val Asn Thr Asn Ala Tyr Tyr Glu Met Ser Gly Leu
                245                 250                 255

GAA GTA AGC TTC GAG GAA CTG CGC ACG TTC GGT GGC CAT GAT GCG AAG        816
Glu Val Ser Phe Glu Glu Leu Arg Thr Phe Gly Gly His Asp Ala Lys
            260                 265                 270

TTT ATC GAC AGC TTG CAG GAG AAC GAG TTC CGT CTG TAC TAC TAC AAC        864
Phe Ile Asp Ser Leu Gln Glu Asn Glu Phe Arg Leu Tyr Tyr Tyr Asn
                275                 280                 285

AAG TTT AAA GAT ATT GCA AGT ACA CTG AAC AAG GCT AAG TCC ATT GTG        912
Lys Phe Lys Asp Ile Ala Ser Thr Leu Asn Lys Ala Lys Ser Ile Val
            290                 295                 300

GGT ACC ACT GCT TCA TTA CAG TAT ATG AAA AAT GTT TTT AAA GAG AAA        960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA       1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT       1056
Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT       1104
Asn Phe Val Lys Phe Phe Lys Val Leu Asn Arg Lys Thr Tyr Leu Asn
                355                 360                 365

TTT GAT AAA GCC GTA TTT AAG ATA AAT ATA GTA CCT AAG GTA AAT TAC       1152
Phe Asp Lys Ala Val Phe Lys Ile Asn Ile Val Pro Lys Val Asn Tyr
370                 375                 380

ACA ATA TAT GAT GGA TTT AAT TTA AGA AAT ACA AAT TTA GCA GCA AAC       1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA       1248
Phe Asn Gly Gln Asn Thr Glu Ile Asn Asn Met Asn Phe Thr Lys Leu
                405                 410                 415

AAA AAT TTT ACT GGA TTG TTT GAA TTT TAT AAG TTG CTA TGT GTA AGA       1296
Lys Asn Phe Thr Gly Leu Phe Glu Phe Tyr Lys Leu Leu Cys Val Arg
            420                 425                 430

GGG ATA ATA ACT TCT AAA ACT AAA TCA TTA GAT AAA GGA TAC AAT AAG       1344
Gly Ile Ile Thr Ser Lys Thr Lys Ser Leu Asp Lys Gly Tyr Asn Lys
                435                 440                 445

ATC GAA GGT CGT TGC GAT GGG GCA TTA AAT GAT TTA TGT ATC AAA GTT       1392
Ile Glu Gly Arg Cys Asp Gly Ala Leu Asn Asp Leu Cys Ile Lys Val
450                 455                 460

AAT AAT TGG GAC TTG TTT TTT AGT CCT TCA GAA GAT AAT TTT ACT AAT       1440
Asn Asn Trp Asp Leu Phe Phe Ser Pro Ser Glu Asp Asn Phe Thr Asn
465                 470                 475                 480

GAT CTA AAT AAA GGA GAA GAA ATT ACA TCT GAT ACT AAT ATA GAA GCA       1488
Asp Leu Asn Lys Gly Glu Glu Ile Thr Ser Asp Thr Asn Ile Glu Ala
                485                 490                 495

GCA GAA GAA AAT ATT AGT TTA GAT TTA ATA CAA CAA TAT TAT TTA ACC       1536
Ala Glu Glu Asn Ile Ser Leu Asp Leu Ile Gln Gln Tyr Tyr Leu Thr
            500                 505                 510

TTT AAT TTT GAT AAT GAA CCT GAA AAT ATT TCA ATA GAA AAT CTT TCA       1584
Phe Asn Phe Asp Asn Glu Pro Glu Asn Ile Ser Ile Glu Asn Leu Ser
            515                 520                 525

AGT GAC ATT ATA GGC CAA TTA GAA CTT ATG CCT AAT ATA GAA AGA TTT       1632
Ser Asp Ile Ile Gly Gln Leu Glu Leu Met Pro Asn Ile Glu Arg Phe
530                 535                 540

CCT AAT GGA AAA AAG TAT GAG TTA GAT AAA TAT ACT ATG TTC CAT TAT       1680
Pro Asn Gly Lys Lys Tyr Glu Leu Asp Lys Tyr Thr Met Phe His Tyr
545                 550                 555                 560
```

| | | |
|---|---|---|
| CTT CGT GCT CAA GAA TTT GAA CAT GGT AAA TCT AGG ATT GCT TTA ACA<br>Leu Arg Ala Gln Glu Phe Glu His Gly Lys Ser Arg Ile Ala Leu Thr<br>565 570 575 | 1728 | |
| AAT TCT GTT AAC GAA GCA TTA TTA AAT CCT AGT CGT GTT TAT ACA TTT<br>Asn Ser Val Asn Glu Ala Leu Leu Asn Pro Ser Arg Val Tyr Thr Phe<br>580 585 590 | 1776 | |
| TTT TCT TCA GAC TAT GTA AAG AAA GTT AAT AAA GCT ACG GAG GCA GCT<br>Phe Ser Ser Asp Tyr Val Lys Lys Val Asn Lys Ala Thr Glu Ala Ala<br>595 600 605 | 1824 | |
| ATG TTT TTA GGC TGG GTA GAA CAA TTA GTA TAT GAT TTT ACC GAT GAA<br>Met Phe Leu Gly Trp Val Glu Gln Leu Val Tyr Asp Phe Thr Asp Glu<br>610 615 620 | 1872 | |
| ACT AGC GAA GTA AGT ACT ACG GAT AAA ATT GCG GAT ATA ACT ATA ATT<br>Thr Ser Glu Val Ser Thr Thr Asp Lys Ile Ala Asp Ile Thr Ile Ile<br>625 630 635 640 | 1920 | |
| ATT CCA TAT ATA GGA CCT GCT TTA AAT ATA GGT AAT ATG TTA TAT AAA<br>Ile Pro Tyr Ile Gly Pro Ala Leu Asn Ile Gly Asn Met Leu Tyr Lys<br>645 650 655 | 1968 | |
| GAT GAT TTT GTA GGT GCT TTA ATA TTT TCA GGA GCT GTT ATT CTG TTA<br>Asp Asp Phe Val Gly Ala Leu Ile Phe Ser Gly Ala Val Ile Leu Leu<br>660 665 670 | 2016 | |
| GAA TTT ATA CCA GAG ATT GCA ATA CCT GTA TTA GGT ACT TTT GCA CTT<br>Glu Phe Ile Pro Glu Ile Ala Ile Pro Val Leu Gly Thr Phe Ala Leu<br>675 680 685 | 2064 | |
| GTA TCA TAT ATT GCG AAT AAG GTT CTA ACC GTT CAA ACA ATA GAT AAT<br>Val Ser Tyr Ile Ala Asn Lys Val Leu Thr Val Gln Thr Ile Asp Asn<br>690 695 700 | 2112 | |
| GCT TTA AGT AAA AGA AAT GAA AAA TGG GAT GAG GTC TAT AAA TAT ATA<br>Ala Leu Ser Lys Arg Asn Glu Lys Trp Asp Glu Val Tyr Lys Tyr Ile<br>705 710 715 720 | 2160 | |
| GTA ACA AAT TGG TTA GCA AAG GTT AAT ACA CAG ATT GAT CTA ATA AGA<br>Val Thr Asn Trp Leu Ala Lys Val Asn Thr Gln Ile Asp Leu Ile Arg<br>725 730 735 | 2208 | |
| AAA AAA ATG AAA GAA GCT TTA GAA AAT CAA GCA GAA GCA ACA AAG GCT<br>Lys Lys Met Lys Glu Ala Leu Glu Asn Gln Ala Glu Ala Thr Lys Ala<br>740 745 750 | 2256 | |
| ATA ATA AAC TAT CAG TAT AAT CAA TAT ACT GAG GAA GAG AAA AAT AAT<br>Ile Ile Asn Tyr Gln Tyr Asn Gln Tyr Thr Glu Glu Glu Lys Asn Asn<br>755 760 765 | 2304 | |
| ATT AAT TTT AAT ATT GAT GAT TTA AGT TCG AAA CTT AAT GAG TCT ATA<br>Ile Asn Phe Asn Ile Asp Asp Leu Ser Ser Lys Leu Asn Glu Ser Ile<br>770 775 780 | 2352 | |
| AAT AAA GCT ATG ATT AAT ATA AAT AAA TTT TTG AAT CAA TGC TCT GTT<br>Asn Lys Ala Met Ile Asn Ile Asn Lys Phe Leu Asn Gln Cys Ser Val<br>785 790 795 800 | 2400 | |
| TCA TAT TTA ATG AAT TCT ATG ATC CCT TAT GGT GTT AAA CGG TTA GAA<br>Ser Tyr Leu Met Asn Ser Met Ile Pro Tyr Gly Val Lys Arg Leu Glu<br>805 810 815 | 2448 | |
| GAT TTT GAT GCT AGT CTT AAA GAT GCA TTA TTA AAG TAT ATA TAT GAT<br>Asp Phe Asp Ala Ser Leu Lys Asp Ala Leu Leu Lys Tyr Ile Tyr Asp<br>820 825 830 | 2496 | |
| AAT AGA GGA ACT TTA ATT GGT CAA GTA GAT AGA TTA AAA GAT AAA GTT<br>Asn Arg Gly Thr Leu Ile Gly Gln Val Asp Arg Leu Lys Asp Lys Val<br>835 840 845 | 2544 | |
| AAT AAT ACA CTT AGT ACA GAT ATA CCT TTT CAG CTT TCC AAA TAC GTA<br>Asn Asn Thr Leu Ser Thr Asp Ile Pro Phe Gln Leu Ser Lys Tyr Val<br>850 855 860 | 2592 | |
| GAT AAT CAA AGA TTA TTA TCT ACA TTT ACT GAA TAT ATT AAG TCT AGG<br>Asp Asn Gln Arg Leu Leu Ser Thr Phe Thr Glu Tyr Ile Lys Ser Arg | 2640 | |

```
                865                 870                 875                 880
CCT GGA CCG GAG ACG CTC TGC GGG GCT GAG CTG GTG GAT GCT CTT CAG                2688
Pro Gly Pro Glu Thr Leu Cys Gly Ala Glu Leu Val Asp Ala Leu Gln
                            885                 890                 895

TTC GTG TGT GGA GAC AGG GGC TTT TAT TTC AAC AAG CCC ACA GGG TAT                2736
Phe Val Cys Gly Asp Arg Gly Phe Tyr Phe Asn Lys Pro Thr Gly Tyr
                900                 905                 910

GGC TCC AGC AGT CGG AGG GCG CCT CAG ACA GGT ATC GTG GAT GAG TGC                2784
Gly Ser Ser Ser Arg Arg Ala Pro Gln Thr Gly Ile Val Asp Glu Cys
            915                 920                 925

TGC TTC CGG AGC TGT GAT CTA AGG AGG CTG GAG ATG TAT TGC GCA CCC                2832
Cys Phe Arg Ser Cys Asp Leu Arg Arg Leu Glu Met Tyr Cys Ala Pro
        930                 935                 940

CTC AAG CCT GCC AAG TCA GCT GAA GCT TAG                                        2862
Leu Lys Pro Ala Lys Ser Ala Glu Ala
945                 950
```

(2) INFORMATION FOR SEQ ID NO: 14:

(i) SEQUENCE CHARACTERISTICS:
        (A) LENGTH: 953 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Gln Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240
```

```
Arg Val Phe Lys Val Asn Thr Asn Ala Tyr Tyr Glu Met Ser Gly Leu
            245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
            325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
            405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ile Glu Gly Arg Cys Asp Gly Ala Leu Asn Asp Leu Cys Ile Lys Val
            450                 455                 460

Asn Asn Trp Asp Leu Phe Phe Ser Pro Ser Glu Asp Asn Phe Thr Asn
465                 470                 475                 480

Asp Leu Asn Lys Gly Glu Glu Ile Thr Ser Asp Thr Asn Ile Glu Ala
            485                 490                 495

Ala Glu Glu Asn Ile Ser Leu Asp Leu Ile Gln Gln Tyr Tyr Leu Thr
            500                 505                 510

Phe Asn Phe Asp Asn Glu Pro Glu Asn Ile Ser Ile Glu Asn Leu Ser
            515                 520                 525

Ser Asp Ile Ile Gly Gln Leu Glu Leu Met Pro Asn Ile Glu Arg Phe
            530                 535                 540

Pro Asn Gly Lys Lys Tyr Glu Leu Asp Lys Tyr Thr Met Phe His Tyr
545                 550                 555                 560

Leu Arg Ala Gln Glu Phe Glu His Gly Lys Ser Arg Ile Ala Leu Thr
            565                 570                 575

Asn Ser Val Asn Glu Ala Leu Leu Asn Pro Ser Arg Val Tyr Thr Phe
            580                 585                 590

Phe Ser Ser Asp Tyr Val Lys Lys Val Asn Lys Ala Thr Glu Ala Ala
            595                 600                 605

Met Phe Leu Gly Trp Val Glu Gln Leu Val Tyr Asp Phe Thr Asp Glu
            610                 615                 620

Thr Ser Glu Val Ser Thr Thr Asp Lys Ile Ala Asp Ile Thr Ile Ile
625                 630                 635                 640

Ile Pro Tyr Ile Gly Pro Ala Leu Asn Ile Gly Asn Met Leu Tyr Lys
            645                 650                 655

Asp Asp Phe Val Gly Ala Leu Ile Phe Ser Gly Ala Val Ile Leu Leu
```

-continued

```
                    660                 665                 670
Glu Phe Ile Pro Glu Ile Ala Ile Pro Val Leu Gly Thr Phe Ala Leu
            675                 680                 685

Val Ser Tyr Ile Ala Asn Lys Val Leu Thr Val Gln Thr Ile Asp Asn
            690                 695                 700

Ala Leu Ser Lys Arg Asn Glu Lys Trp Asp Glu Val Tyr Lys Tyr Ile
705                 710                 715                 720

Val Thr Asn Trp Leu Ala Lys Val Asn Thr Gln Ile Asp Leu Ile Arg
                725                 730                 735

Lys Lys Met Lys Glu Ala Leu Glu Asn Gln Ala Glu Ala Thr Lys Ala
            740                 745                 750

Ile Ile Asn Tyr Gln Tyr Asn Gln Tyr Thr Glu Glu Lys Asn Asn
            755                 760                 765

Ile Asn Phe Asn Ile Asp Asp Leu Ser Ser Lys Leu Asn Glu Ser Ile
            770                 775                 780

Asn Lys Ala Met Ile Asn Ile Asn Lys Phe Leu Asn Gln Cys Ser Val
785                 790                 795                 800

Ser Tyr Leu Met Asn Ser Met Ile Pro Tyr Gly Val Lys Arg Leu Glu
            805                 810                 815

Asp Phe Asp Ala Ser Leu Lys Asp Ala Leu Leu Lys Tyr Ile Tyr Asp
            820                 825                 830

Asn Arg Gly Thr Leu Ile Gly Gln Val Asp Arg Leu Lys Asp Lys Val
            835                 840                 845

Asn Asn Thr Leu Ser Thr Asp Ile Pro Phe Gln Leu Ser Lys Tyr Val
            850                 855                 860

Asp Asn Gln Arg Leu Leu Ser Thr Phe Thr Glu Tyr Ile Lys Ser Arg
865                 870                 875                 880

Pro Gly Pro Glu Thr Leu Cys Gly Ala Glu Leu Val Asp Ala Leu Gln
            885                 890                 895

Phe Val Cys Gly Asp Arg Gly Phe Tyr Phe Asn Lys Pro Thr Gly Tyr
            900                 905                 910

Gly Ser Ser Ser Arg Arg Ala Pro Gln Thr Gly Ile Val Asp Glu Cys
            915                 920                 925

Cys Phe Arg Ser Cys Asp Leu Arg Arg Leu Glu Met Tyr Cys Ala Pro
930                 935                 940

Leu Lys Pro Ala Lys Ser Ala Glu Ala
945                 950
```

(2) INFORMATION FOR SEQ ID NO: 15:

(i) SEQUENCE CHARACTERISTICS:
        (A) LENGTH: 2724 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2724

(xi) SEQUENCE DESCRIPTION: SEQ ID NO: 15:

```
ATG CAG TTC GTG AAC AAG CAG TTC AAC TAT AAG GAC CCT GTA AAC GGT       48
Met Gln Phe Val Asn Lys Gln Phe Asn Tyr Lys Asp Pro Val Asn Gly
  1               5                  10                  15

GTT GAC ATT GCC TAC ATC AAA ATT CCA AAC GCC GGC CAG ATG CAG CCG       96
Val Asp Ile Ala Tyr Ile Lys Ile Pro Asn Ala Gly Gln Met Gln Pro
```

```
                    20                      25                         30
GTG AAG GCT TTC AAG ATT CAT AAC AAA ATC TGG GTT ATT CCG GAA CGC        144
Val Lys Ala Phe Lys Ile His Asn Lys Ile Trp Val Ile Pro Glu Arg
             35                  40                  45

GAT ACA TTT ACG AAC CCG GAA GAA GGA GAC TTG AAC CCG CCG CCG GAA        192
Asp Thr Phe Thr Asn Pro Glu Glu Gly Asp Leu Asn Pro Pro Pro Glu
         50                  55                  60

GCA AAG CAG GTG CCA GTT TCA TAC TAC GAT TCA ACC TAT CTG AGC ACA        240
Ala Lys Gln Val Pro Val Ser Tyr Tyr Asp Ser Thr Tyr Leu Ser Thr
 65                  70                  75                  80

GAC AAC GAG AAG GAT AAC TAC CTG AAG GGA GTG ACC AAA TTA TTC GAG        288
Asp Asn Glu Lys Asp Asn Tyr Leu Lys Gly Val Thr Lys Leu Phe Glu
                 85                  90                  95

CGT ATT TAT TCC ACT GAC CTG GGC CGT ATG CTG CTG ACC TCA ATC GTC        336
Arg Ile Tyr Ser Thr Asp Leu Gly Arg Met Leu Leu Thr Ser Ile Val
             100                 105                 110

CGC GGA ATC CCA TTT TGG GGT GGC AGT ACC ATT GAC ACG GAG TTG AAG        384
Arg Gly Ile Pro Phe Trp Gly Gly Ser Thr Ile Asp Thr Glu Leu Lys
         115                 120                 125

GTT ATT GAC ACT AAC TGC ATT AAC GTG ATC CAA CCA GAC GGT AGC TAC        432
Val Ile Asp Thr Asn Cys Ile Asn Val Ile Gln Pro Asp Gly Ser Tyr
 130                 135                 140

AGA TCT GAA GAA CTT AAC CTC GTA ATC ATC GGG CCC TCC GCG GAC ATT        480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG        528
Ile Gln Phe Glu Cys Lys Ser Phe Gly His Glu Val Leu Asn Leu Thr
             165                 170                 175

CGT AAC GGT TAC GGC TCT ACT CAG TAC ATT CGT TTC AGC CCA GAC TTC        576
Arg Asn Gly Tyr Gly Ser Thr Gln Tyr Ile Arg Phe Ser Pro Asp Phe
         180                 185                 190

ACG TTC GGT TTC GAG GAG AGC CTG GAG GTT GAT ACC AAC CCG CTG TTG        624
Thr Phe Gly Phe Glu Glu Ser Leu Glu Val Asp Thr Asn Pro Leu Leu
 195                 200                 205

GGT GCA GGC AAG TTC GCA ACT GAT CCA GCG GTG ACC CTG GCA CAC GAG        672
Gly Ala Gly Lys Phe Ala Thr Asp Pro Ala Val Thr Leu Ala His Glu
             210                 215                 220

CTG ATC CAC GCC GGT CAT CGT CTG TAT GGC ATT GCG ATT AAC CCG AAC        720
Leu Ile His Ala Gly His Arg Leu Tyr Gly Ile Ala Ile Asn Pro Asn
225                 230                 235                 240

CGC GTG TTC AAG GTT AAC ACC AAC GCC TAC TAC GAG ATG AGT GGT TTA        768
Arg Val Phe Lys Val Asn Thr Asn Ala Tyr Tyr Glu Met Ser Gly Leu
             245                 250                 255

GAA GTA AGC TTC GAG GAA CTG CGC ACG TTC GGT GGC CAT GAT GCG AAG        816
Glu Val Ser Phe Glu Glu Leu Arg Thr Phe Gly Gly His Asp Ala Lys
         260                 265                 270

TTT ATC GAC AGC TTG CAG GAG AAC GAG TTC CGT CTG TAC TAC TAC AAC        864
Phe Ile Asp Ser Leu Gln Glu Asn Glu Phe Arg Leu Tyr Tyr Tyr Asn
 275                 280                 285

AAG TTT AAA GAT ATT GCA AGT ACA CTG AAC AAG GCT AAG TCC ATT GTG        912
Lys Phe Lys Asp Ile Ala Ser Thr Leu Asn Lys Ala Lys Ser Ile Val
             290                 295                 300

GGT ACC ACT GCT TCA TTA CAG TAT ATG AAA AAT GTT TTT AAA GAG AAA        960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA       1008
Tyr Leu Leu Ser Glu Asp Thr Ser Gly Lys Phe Ser Val Asp Lys Leu
             325                 330                 335

AAA TTT GAT AAG TTA TAC AAA ATG TTA ACA GAG ATT TAC ACA GAG GAT       1056
```

```
                                                    -continued

Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT      1104
Asn Phe Val Lys Phe Phe Lys Val Leu Asn Arg Lys Thr Tyr Leu Asn
            355                 360                 365

TTT GAT AAA GCC GTA TTT AAG ATA AAT ATA GTA CCT AAG GTA AAT TAC      1152
Phe Asp Lys Ala Val Phe Lys Ile Asn Ile Val Pro Lys Val Asn Tyr
            370                 375                 380

ACA ATA TAT GAT GGA TTT AAT TTA AGA AAT ACA AAT TTA GCA GCA AAC      1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA      1248
Phe Asn Gly Gln Asn Thr Glu Ile Asn Asn Met Asn Phe Thr Lys Leu
            405                 410                 415

AAA AAT TTT ACT GGA TTG TTT GAA TTT TAT AAG TTG CTA TGT GTA AGA      1296
Lys Asn Phe Thr Gly Leu Phe Glu Phe Tyr Lys Leu Leu Cys Val Arg
            420                 425                 430

GGG ATA ATA ACT TCT AAA ACT AAA TCA TTA GAT AAA GGA TAC AAT AAG      1344
Gly Ile Ile Thr Ser Lys Thr Lys Ser Leu Asp Lys Gly Tyr Asn Lys
            435                 440                 445

ATC GAA GGT CGT TGC GAT GGG GCA TTA AAT GAT TTA TGT ATC AAA GTT      1392
Ile Glu Gly Arg Cys Asp Gly Ala Leu Asn Asp Leu Cys Ile Lys Val
            450                 455                 460

AAT AAT TGG GAC TTG TTT TTT AGT CCT TCA GAA GAT AAT TTT ACT AAT      1440
Asn Asn Trp Asp Leu Phe Phe Ser Pro Ser Glu Asp Asn Phe Thr Asn
465                 470                 475                 480

GAT CTA AAT AAA GGA GAA GAA ATT ACA TCT GAT ACT AAT ATA GAA GCA      1488
Asp Leu Asn Lys Gly Glu Glu Ile Thr Ser Asp Thr Asn Ile Glu Ala
            485                 490                 495

GCA GAA GAA AAT ATT AGT TTA GAT TTA ATA CAA CAA TAT TAT TTA ACC      1536
Ala Glu Glu Asn Ile Ser Leu Asp Leu Ile Gln Gln Tyr Tyr Leu Thr
            500                 505                 510

TTT AAT TTT GAT AAT GAA CCT GAA AAT ATT TCA ATA GAA AAT CTT TCA      1584
Phe Asn Phe Asp Asn Glu Pro Glu Asn Ile Ser Ile Glu Asn Leu Ser
            515                 520                 525

AGT GAC ATT ATA GGC CAA TTA GAA CTT ATG CCT AAT ATA GAA AGA TTT      1632
Ser Asp Ile Ile Gly Gln Leu Glu Leu Met Pro Asn Ile Glu Arg Phe
            530                 535                 540

CCT AAT GGA AAA AAG TAT GAG TTA GAT AAA TAT ACT ATG TTC CAT TAT      1680
Pro Asn Gly Lys Lys Tyr Glu Leu Asp Lys Tyr Thr Met Phe His Tyr
545                 550                 555                 560

CTT CGT GCT CAA GAA TTT GAA CAT GGT AAA TCT AGG ATT GCT TTA ACA      1728
Leu Arg Ala Gln Glu Phe Glu His Gly Lys Ser Arg Ile Ala Leu Thr
            565                 570                 575

AAT TCT GTT AAC GAA GCA TTA TTA AAT CCT AGT CGT GTT TAT ACA TTT      1776
Asn Ser Val Asn Glu Ala Leu Leu Asn Pro Ser Arg Val Tyr Thr Phe
            580                 585                 590

TTT TCT TCA GAC TAT GTA AAG AAA GTT AAT AAA GCT ACG GAG GCA GCT      1824
Phe Ser Ser Asp Tyr Val Lys Lys Val Asn Lys Ala Thr Glu Ala Ala
            595                 600                 605

ATG TTT TTA GGC TGG GTA GAA CAA TTA GTA TAT GAT TTT ACC GAT GAA      1872
Met Phe Leu Gly Trp Val Glu Gln Leu Val Tyr Asp Phe Thr Asp Glu
            610                 615                 620

ACT AGC GAA GTA AGT ACT ACG GAT AAA ATT GCG GAT ATA ACT ATA ATT      1920
Thr Ser Glu Val Ser Thr Thr Asp Lys Ile Ala Asp Ile Thr Ile Ile
625                 630                 635                 640

ATT CCA TAT ATA GGA CCT GCT TTA AAT ATA GGT AAT ATG TTA TAT AAA      1968
Ile Pro Tyr Ile Gly Pro Ala Leu Asn Ile Gly Asn Met Leu Tyr Lys
            645                 650                 655
```

```
GAT GAT TTT GTA GGT GCT TTA ATA TTT TCA GGA GCT GTT ATT CTG TTA      2016
Asp Asp Phe Val Gly Ala Leu Ile Phe Ser Gly Ala Val Ile Leu Leu
            660                 665                 670

GAA TTT ATA CCA GAG ATT GCA ATA CCT GTA TTA GGT ACT TTT GCA CTT      2064
Glu Phe Ile Pro Glu Ile Ala Ile Pro Val Leu Gly Thr Phe Ala Leu
                675                 680                 685

GTA TCA TAT ATT GCG AAT AAG GTT CTA ACC GTT CAA ACA ATA GAT AAT      2112
Val Ser Tyr Ile Ala Asn Lys Val Leu Thr Val Gln Thr Ile Asp Asn
        690                 695                 700

GCT TTA AGT AAA AGA AAT GAA AAA TGG GAT GAG GTC TAT AAA TAT ATA      2160
Ala Leu Ser Lys Arg Asn Glu Lys Trp Asp Glu Val Tyr Lys Tyr Ile
705                 710                 715                 720

GTA ACA AAT TGG TTA GCA AAG GTT AAT ACA CAG ATT GAT CTA ATA AGA      2208
Val Thr Asn Trp Leu Ala Lys Val Asn Thr Gln Ile Asp Leu Ile Arg
                725                 730                 735

AAA AAA ATG AAA GAA GCT TTA GAA AAT CAA GCA GAA GCA ACA AAG GCT      2256
Lys Lys Met Lys Glu Ala Leu Glu Asn Gln Ala Glu Ala Thr Lys Ala
            740                 745                 750

ATA ATA AAC TAT CAG TAT AAT CAA TAT ACT GAG GAA GAG AAA AAT AAT      2304
Ile Ile Asn Tyr Gln Tyr Asn Gln Tyr Thr Glu Glu Glu Lys Asn Asn
        755                 760                 765

ATT AAT TTT AAT ATT GAT GAT TTA AGT TCG AAA CTT AAT GAG TCT ATA      2352
Ile Asn Phe Asn Ile Asp Asp Leu Ser Ser Lys Leu Asn Glu Ser Ile
770                 775                 780

AAT AAA GCT ATG ATT AAT ATA AAT AAA TTT TTG AAT CAA TGC TCT GTT      2400
Asn Lys Ala Met Ile Asn Ile Asn Lys Phe Leu Asn Gln Cys Ser Val
785                 790                 795                 800

TCA TAT TTA ATG AAT TCT ATG ATC CCT TAT GGT GTT AAA CGG TTA GAA      2448
Ser Tyr Leu Met Asn Ser Met Ile Pro Tyr Gly Val Lys Arg Leu Glu
                805                 810                 815

GAT TTT GAT GCT AGT CTT AAA GAT GCA TTA TTA AAG TAT ATA TAT GAT      2496
Asp Phe Asp Ala Ser Leu Lys Asp Ala Leu Leu Lys Tyr Ile Tyr Asp
            820                 825                 830

AAT AGA GGA ACT TTA ATT GGT CAA GTA GAT AGA TTA AAA GAT AAA GTT      2544
Asn Arg Gly Thr Leu Ile Gly Gln Val Asp Arg Leu Lys Asp Lys Val
        835                 840                 845

AAT AAT ACA CTT AGT ACA GAT ATA CCT TTT CAG CTT TCC AAA TAC GTA      2592
Asn Asn Thr Leu Ser Thr Asp Ile Pro Phe Gln Leu Ser Lys Tyr Val
850                 855                 860

GAT AAT CAA AGA TTA TTA TCT ACA TTT ACT GAA TAT ATT AAG TCT AGG      2640
Asp Asn Gln Arg Leu Leu Ser Thr Phe Thr Glu Tyr Ile Lys Ser Arg
865                 870                 875                 880

CCT CAA TCT AAA GTT AAA AGA CAA ATA TTT TCA GGC TAT CAA TCT GAT      2688
Pro Gln Ser Lys Val Lys Arg Gln Ile Phe Ser Gly Tyr Gln Ser Asp
                885                 890                 895

ATT GAT ACA CAT AAT AGA ATT AAG GAT GAA TTA TGA                      2724
Ile Asp Thr His Asn Arg Ile Lys Asp Glu Leu
            900                 905
```

(2) INFORMATION FOR SEQ ID NO: 16:

(i) SEQUENCE CHARACTERISTICS:
        (A) LENGTH: 907 amino acids
        (B) TYPE: amino acid
        (D) TOPOLOGY: linear (ii) MOLECULE TYPE: protein (xi) SEQUENCE DESCRIPTION: SEQ ID NO: 16:

```
Met Gln Phe Val Asn Lys Gln Phe Asn Tyr Lys Asp Pro Val Asn Gly
 1               5                  10                  15
```

```
Val Asp Ile Ala Tyr Ile Lys Ile Pro Asn Ala Gly Gln Met Gln Pro
         20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
         50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
```

```
                435                 440                 445
Ile Glu Gly Arg Cys Asp Gly Ala Leu Asn Asp Leu Cys Ile Lys Val
    450                 455                 460

Asn Asn Trp Asp Leu Phe Phe Ser Pro Ser Glu Asp Asn Phe Thr Asn
465                 470                 475                 480

Asp Leu Asn Lys Gly Glu Glu Ile Thr Ser Asp Thr Asn Ile Glu Ala
                485                 490                 495

Ala Glu Glu Asn Ile Ser Leu Asp Leu Ile Gln Gln Tyr Tyr Leu Thr
            500                 505                 510

Phe Asn Phe Asp Asn Glu Pro Glu Asn Ile Ser Ile Glu Asn Leu Ser
            515                 520                 525

Ser Asp Ile Ile Gly Gln Leu Glu Leu Met Pro Asn Ile Glu Arg Phe
    530                 535                 540

Pro Asn Gly Lys Lys Tyr Glu Leu Asp Lys Tyr Thr Met Phe His Tyr
545                 550                 555                 560

Leu Arg Ala Gln Glu Phe Glu His Gly Lys Ser Arg Ile Ala Leu Thr
                565                 570                 575

Asn Ser Val Asn Glu Ala Leu Leu Asn Pro Ser Arg Val Tyr Thr Phe
            580                 585                 590

Phe Ser Ser Asp Tyr Val Lys Lys Val Asn Lys Ala Thr Glu Ala Ala
        595                 600                 605

Met Phe Leu Gly Trp Val Glu Gln Leu Val Tyr Asp Phe Thr Asp Glu
    610                 615                 620

Thr Ser Glu Val Ser Thr Thr Asp Lys Ile Ala Asp Ile Thr Ile Ile
625                 630                 635                 640

Ile Pro Tyr Ile Gly Pro Ala Leu Asn Ile Gly Asn Met Leu Tyr Lys
                645                 650                 655

Asp Asp Phe Val Gly Ala Leu Ile Phe Ser Gly Ala Val Ile Leu Leu
            660                 665                 670

Glu Phe Ile Pro Glu Ile Ala Ile Pro Val Leu Gly Thr Phe Ala Leu
            675                 680                 685

Val Ser Tyr Ile Ala Asn Lys Val Leu Thr Val Gln Thr Ile Asp Asn
    690                 695                 700

Ala Leu Ser Lys Arg Asn Glu Lys Trp Asp Glu Val Tyr Lys Tyr Ile
705                 710                 715                 720

Val Thr Asn Trp Leu Ala Lys Val Asn Thr Gln Ile Asp Leu Ile Arg
                725                 730                 735

Lys Lys Met Lys Glu Ala Leu Glu Asn Gln Ala Glu Ala Thr Lys Ala
            740                 745                 750

Ile Ile Asn Tyr Gln Tyr Asn Gln Tyr Thr Glu Glu Lys Asn Asn
            755                 760                 765

Ile Asn Phe Asn Ile Asp Asp Leu Ser Ser Lys Leu Asn Glu Ser Ile
770                 775                 780

Asn Lys Ala Met Ile Asn Ile Asn Lys Phe Leu Asn Gln Cys Ser Val
785                 790                 795                 800

Ser Tyr Leu Met Asn Ser Met Ile Pro Tyr Gly Val Lys Arg Leu Glu
                805                 810                 815

Asp Phe Asp Ala Ser Leu Lys Asp Ala Leu Leu Lys Tyr Ile Tyr Asp
            820                 825                 830

Asn Arg Gly Thr Leu Ile Gly Gln Val Asp Arg Leu Lys Asp Lys Val
            835                 840                 845

Asn Asn Thr Leu Ser Thr Asp Ile Pro Phe Gln Leu Ser Lys Tyr Val
850                 855                 860
```

```
Asp Asn Gln Arg Leu Leu Ser Thr Phe Thr Glu Tyr Ile Lys Ser Arg
865                 870                 875                 880

Pro Gln Ser Lys Val Lys Arg Gln Ile Phe Ser Gly Tyr Gln Ser Asp
                885                 890                 895

Ile Asp Thr His Asn Arg Ile Lys Asp Glu Leu
                900                 905
```

(2) INFORMATION FOR SEQ ID NO: 17:

(i) SEQUENCE CHARACTERISTICS:
        (A) LENGTH: 3042 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..3042

(xi) SEQUENCE DESCRIPTION: SEQ ID NO: 17:

```
ATG CAG TTC GTG AAC AAG CAG TTC AAC TAT AAG GAC CCT GTA AAC GGT        48
Met Gln Phe Val Asn Lys Gln Phe Asn Tyr Lys Asp Pro Val Asn Gly
 1               5                  10                  15

GTT GAC ATT GCC TAC ATC AAA ATT CCA AAC GCC GGC CAG ATG CAG CCG        96
Val Asp Ile Ala Tyr Ile Lys Ile Pro Asn Ala Gly Gln Met Gln Pro
                20                  25                  30

GTG AAG GCT TTC AAG ATT CAT AAC AAA ATC TGG GTT ATT CCG GAA CGC       144
Val Lys Ala Phe Lys Ile His Asn Lys Ile Trp Val Ile Pro Glu Arg
            35                  40                  45

GAT ACA TTT ACG AAC CCG GAA GAA GGA GAC TTG AAC CCG CCG CCG GAA       192
Asp Thr Phe Thr Asn Pro Glu Glu Gly Asp Leu Asn Pro Pro Pro Glu
         50                  55                  60

GCA AAG CAG GTG CCA GTT TCA TAC TAC GAT TCA ACC TAT CTG AGC ACA       240
Ala Lys Gln Val Pro Val Ser Tyr Tyr Asp Ser Thr Tyr Leu Ser Thr
 65                  70                  75                  80

GAC AAC GAG AAG GAT AAC TAC CTG AAG GGA GTG ACC AAA TTA TTC GAG       288
Asp Asn Glu Lys Asp Asn Tyr Leu Lys Gly Val Thr Lys Leu Phe Glu
                85                  90                  95

CGT ATT TAT TCC ACT GAC CTG GGC CGT ATG CTG CTG ACC TCA ATC GTC       336
Arg Ile Tyr Ser Thr Asp Leu Gly Arg Met Leu Leu Thr Ser Ile Val
               100                 105                 110

CGC GGA ATC CCA TTT TGG GGT GGC AGT ACC ATT GAC ACG GAG TTG AAG       384
Arg Gly Ile Pro Phe Trp Gly Gly Ser Thr Ile Asp Thr Glu Leu Lys
           115                 120                 125

GTT ATT GAC ACT AAC TGC ATT AAC GTG ATC CAA CCA GAC GGT AGC TAC       432
Val Ile Asp Thr Asn Cys Ile Asn Val Ile Gln Pro Asp Gly Ser Tyr
130                 135                 140

AGA TCT GAA GAA CTT AAC CTC GTA ATC ATC GGG CCC TCC GCG GAC ATT       480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG       528
Ile Gln Phe Glu Cys Lys Ser Phe Gly His Glu Val Leu Asn Leu Thr
                165                 170                 175

CGT AAC GGT TAC GGC TCT ACT CAG TAC ATT CGT TTC AGC CCA GAC TTC       576
Arg Asn Gly Tyr Gly Ser Thr Gln Tyr Ile Arg Phe Ser Pro Asp Phe
            180                 185                 190

ACG TTC GGT TTC GAG GAG AGC CTG GAG GTT GAT ACC AAC CCG CTG TTG       624
Thr Phe Gly Phe Glu Glu Ser Leu Glu Val Asp Thr Asn Pro Leu Leu
        195                 200                 205
```

```
GGT GCA GGC AAG TTC GCA ACT GAT CCA GCG GTG ACC CTG GCA CAC GAG        672
Gly Ala Gly Lys Phe Ala Thr Asp Pro Ala Val Thr Leu Ala His Glu
    210                 215                 220

CTG ATC CAC GCC GGT CAT CGT CTG TAT GGC ATT GCG ATT AAC CCG AAC        720
Leu Ile His Ala Gly His Arg Leu Tyr Gly Ile Ala Ile Asn Pro Asn
225                 230                 235                 240

CGC GTG TTC AAG GTT AAC ACC AAC GCC TAC TAC GAG ATG AGT GGT TTA        768
Arg Val Phe Lys Val Asn Thr Asn Ala Tyr Tyr Glu Met Ser Gly Leu
                245                 250                 255

GAA GTA AGC TTC GAG GAA CTG CGC ACG TTC GGT GGC CAT GAT GCG AAG        816
Glu Val Ser Phe Glu Glu Leu Arg Thr Phe Gly Gly His Asp Ala Lys
            260                 265                 270

TTT ATC GAC AGC TTG CAG GAG AAC GAG TTC CGT CTG TAC TAC TAC AAC        864
Phe Ile Asp Ser Leu Gln Glu Asn Glu Phe Arg Leu Tyr Tyr Tyr Asn
        275                 280                 285

AAG TTT AAA GAT ATT GCA AGT ACA CTG AAC AAG GCT AAG TCC ATT GTG        912
Lys Phe Lys Asp Ile Ala Ser Thr Leu Asn Lys Ala Lys Ser Ile Val
    290                 295                 300

GGT ACC ACT GCT TCA TTA CAG TAT ATG AAA AAT GTT TTT AAA GAG AAA        960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA       1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT       1056
Lys Phe Asp Lys Leu Tyr Lys Met Leu Thr Glu Ile Tyr Thr Glu Asp
            340                 345                 350

AAT TTT GTT AAG TTT TTT AAA GTA CTT AAC AGA AAA ACA TAT TTG AAT       1104
Asn Phe Val Lys Phe Phe Lys Val Leu Asn Arg Lys Thr Tyr Leu Asn
        355                 360                 365

TTT GAT AAA GCC GTA TTT AAG ATA AAT ATA GTA CCT AAG GTA AAT TAC       1152
Phe Asp Lys Ala Val Phe Lys Ile Asn Ile Val Pro Lys Val Asn Tyr
    370                 375                 380

ACA ATA TAT GAT GGA TTT AAT TTA AGA AAT ACA AAT TTA GCA GCA AAC       1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA       1248
Phe Asn Gly Gln Asn Thr Glu Ile Asn Asn Met Asn Phe Thr Lys Leu
                405                 410                 415

AAA AAT TTT ACT GGA TTG TTT GAA TTT TAT AAG TTG CTA TGT GTA AGA       1296
Lys Asn Phe Thr Gly Leu Phe Glu Phe Tyr Lys Leu Leu Cys Val Arg
            420                 425                 430

GGG ATA ATA ACT TCT AAA ACT AAA TCA TTA GAT AAA GGA TAC AAT AAG       1344
Gly Ile Ile Thr Ser Lys Thr Lys Ser Leu Asp Lys Gly Tyr Asn Lys
        435                 440                 445

ATC GAA GGT CGT TGC GAT GGG GCA TTA AAT GAT TTA TGT ATC AAA GTT       1392
Ile Glu Gly Arg Cys Asp Gly Ala Leu Asn Asp Leu Cys Ile Lys Val
    450                 455                 460

AAT AAT TGG GAC TTG TTT TTT AGT CCT TCA GAA GAT AAT TTT ACT AAT       1440
Asn Asn Trp Asp Leu Phe Phe Ser Pro Ser Glu Asp Asn Phe Thr Asn
465                 470                 475                 480

GAT CTA AAT AAA GGA GAA GAA ATT ACA TCT GAT ACT AAT ATA GAA GCA       1488
Asp Leu Asn Lys Gly Glu Glu Ile Thr Ser Asp Thr Asn Ile Glu Ala
                485                 490                 495

GCA GAA GAA AAT ATT AGT TTA GAT TTA ATA CAA CAA TAT TAT TTA ACC       1536
Ala Glu Glu Asn Ile Ser Leu Asp Leu Ile Gln Gln Tyr Tyr Leu Thr
            500                 505                 510

TTT AAT TTT GAT AAT GAA CCT GAA AAT ATT TCA ATA GAA AAT CTT TCA       1584
Phe Asn Phe Asp Asn Glu Pro Glu Asn Ile Ser Ile Glu Asn Leu Ser
        515                 520                 525
```

```
AGT GAC ATT ATA GGC CAA TTA GAA CTT ATG CCT AAT ATA GAA AGA TTT      1632
Ser Asp Ile Ile Gly Gln Leu Glu Leu Met Pro Asn Ile Glu Arg Phe
    530                 535                 540

CCT AAT GGA AAA AAG TAT GAG TTA GAT AAA TAT ACT ATG TTC CAT TAT      1680
Pro Asn Gly Lys Lys Tyr Glu Leu Asp Lys Tyr Thr Met Phe His Tyr
545                 550                 555                 560

CTT CGT GCT CAA GAA TTT GAA CAT GGT AAA TCT AGG ATT GCT TTA ACA      1728
Leu Arg Ala Gln Glu Phe Glu His Gly Lys Ser Arg Ile Ala Leu Thr
                565                 570                 575

AAT TCT GTT AAC GAA GCA TTA TTA AAT CCT AGT CGT GTT TAT ACA TTT      1776
Asn Ser Val Asn Glu Ala Leu Leu Asn Pro Ser Arg Val Tyr Thr Phe
            580                 585                 590

TTT TCT TCA GAC TAT GTA AAG AAA GTT AAT AAA GCT ACG GAG GCA GCT      1824
Phe Ser Ser Asp Tyr Val Lys Lys Val Asn Lys Ala Thr Glu Ala Ala
        595                 600                 605

ATG TTT TTA GGC TGG GTA GAA CAA TTA GTA TAT GAT TTT ACC GAT GAA      1872
Met Phe Leu Gly Trp Val Glu Gln Leu Val Tyr Asp Phe Thr Asp Glu
    610                 615                 620

ACT AGC GAA GTA AGT ACT ACG GAT AAA ATT GCG GAT ATA ACT ATA ATT      1920
Thr Ser Glu Val Ser Thr Thr Asp Lys Ile Ala Asp Ile Thr Ile Ile
625                 630                 635                 640

ATT CCA TAT ATA GGA CCT GCT TTA AAT ATA GGT AAT ATG TTA TAT AAA      1968
Ile Pro Tyr Ile Gly Pro Ala Leu Asn Ile Gly Asn Met Leu Tyr Lys
                645                 650                 655

GAT GAT TTT GTA GGT GCT TTA ATA TTT TCA GGA GCT GTT ATT CTG TTA      2016
Asp Asp Phe Val Gly Ala Leu Ile Phe Ser Gly Ala Val Ile Leu Leu
            660                 665                 670

GAA TTT ATA CCA GAG ATT GCA ATA CCT GTA TTA GGT ACT TTT GCA CTT      2064
Glu Phe Ile Pro Glu Ile Ala Ile Pro Val Leu Gly Thr Phe Ala Leu
        675                 680                 685

GTA TCA TAT ATT GCG AAT AAG GTT CTA ACC GTT CAA ACA ATA GAT AAT      2112
Val Ser Tyr Ile Ala Asn Lys Val Leu Thr Val Gln Thr Ile Asp Asn
    690                 695                 700

GCT TTA AGT AAA AGA AAT GAA AAA TGG GAT GAG GTC TAT AAA TAT ATA      2160
Ala Leu Ser Lys Arg Asn Glu Lys Trp Asp Glu Val Tyr Lys Tyr Ile
705                 710                 715                 720

GTA ACA AAT TGG TTA GCA AAG GTT AAT ACA CAG ATT GAT CTA ATA AGA      2208
Val Thr Asn Trp Leu Ala Lys Val Asn Thr Gln Ile Asp Leu Ile Arg
                725                 730                 735

AAA AAA ATG AAA GAA GCT TTA GAA AAT CAA GCA GAA GCA ACA AAG GCT      2256
Lys Lys Met Lys Glu Ala Leu Glu Asn Gln Ala Glu Ala Thr Lys Ala
            740                 745                 750

ATA ATA AAC TAT CAG TAT AAT CAA TAT ACT GAG GAA GAG AAA AAT AAT      2304
Ile Ile Asn Tyr Gln Tyr Asn Gln Tyr Thr Glu Glu Glu Lys Asn Asn
        755                 760                 765

ATT AAT TTT AAT ATT GAT GAT TTA AGT TCG AAA CTT AAT GAG TCT ATA      2352
Ile Asn Phe Asn Ile Asp Asp Leu Ser Ser Lys Leu Asn Glu Ser Ile
    770                 775                 780

AAT AAA GCT ATG ATT AAT ATA AAT AAA TTT TTG AAT CAA TGC TCT GTT      2400
Asn Lys Ala Met Ile Asn Ile Asn Lys Phe Leu Asn Gln Cys Ser Val
785                 790                 795                 800

TCA TAT TTA ATG AAT TCT ATG ATC CCT TAT GGT GTT AAA CGG TTA GAA      2448
Ser Tyr Leu Met Asn Ser Met Ile Pro Tyr Gly Val Lys Arg Leu Glu
                805                 810                 815

GAT TTT GAT GCT AGT CTT AAA GAT GCA TTA TTA AAG TAT ATA TAT GAT      2496
Asp Phe Asp Ala Ser Leu Lys Asp Ala Leu Leu Lys Tyr Ile Tyr Asp
            820                 825                 830

AAT AGA GGA ACT TTA ATT GGT CAA GTA GAT AGA TTA AAA GAT AAA GTT      2544
Asn Arg Gly Thr Leu Ile Gly Gln Val Asp Arg Leu Lys Asp Lys Val
```

-continued

```
              835                 840                 845
AAT AAT ACA CTT AGT ACA GAT ATA CCT TTT CAG CTT TCC AAA TAC GTA      2592
Asn Asn Thr Leu Ser Thr Asp Ile Pro Phe Gln Leu Ser Lys Tyr Val
    850                 855                 860

GAT AAT CAA AGA TTA TTA TCT ACA TTT ACT GAA TAT ATT AAG TCA GGC      2640
Asp Asn Gln Arg Leu Leu Ser Thr Phe Thr Glu Tyr Ile Lys Ser Gly
865                 870                 875                 880

CTG AAT TCC CCG GGT GCA GCT CAT TAT GCG CAA CAC GAT GAA GCC GTA      2688
Leu Asn Ser Pro Gly Ala Ala His Tyr Ala Gln His Asp Glu Ala Val
                885                 890                 895

GAC AAC AAA TTC AAC AAA GAA CAA CAA AAC GCG TTC TAT GAG ATC TTA      2736
Asp Asn Lys Phe Asn Lys Glu Gln Gln Asn Ala Phe Tyr Glu Ile Leu
            900                 905                 910

CAT TTA CCT AAC TTA AAC GAA GAA CAA CGA AAC GCC TTC ATC CAA AGT      2784
His Leu Pro Asn Leu Asn Glu Glu Gln Arg Asn Ala Phe Ile Gln Ser
        915                 920                 925

TTA AAA GAT GAC CCA AGC CAA AGC GCT AAC CTT TTA GCA GAA GCT AAA      2832
Leu Lys Asp Asp Pro Ser Gln Ser Ala Asn Leu Leu Ala Glu Ala Lys
    930                 935                 940

AAG CTA AAT GAT GCT CAG GCG CCG AAA GTA GAC AAC AAA TTC AAC AAA      2880
Lys Leu Asn Asp Ala Gln Ala Pro Lys Val Asp Asn Lys Phe Asn Lys
945                 950                 955                 960

GAA CAA CAA AAC GCG TTC TAT GAG ATC TTA CAT TTA CCT AAC TTA AAC      2928
Glu Gln Gln Asn Ala Phe Tyr Glu Ile Leu His Leu Pro Asn Leu Asn
                965                 970                 975

GAA GAA CAA CGA AAC GCC TTC ATC CAA AGT TTA AAA GAT GAC CCA AGC      2976
Glu Glu Gln Arg Asn Ala Phe Ile Gln Ser Leu Lys Asp Asp Pro Ser
            980                 985                 990

CAA AGC GCT AAC CTT TTA GCA GAA GCT AAA AAG CTA AAT GAT GCT CAG      3024
Gln Ser Ala Asn Leu Leu Ala Glu Ala Lys Lys Leu Asn Asp Ala Gln
        995                 1000                1005

GCG CCG AAA GTA GAC TAG                                              3042
Ala Pro Lys Val Asp
    1010
```

(2) INFORMATION FOR SEQ ID NO: 18:

(i) SEQUENCE CHARACTERISTICS:
        (A) LENGTH: 1013 amino acids
        (B) TYPE: amino acid
        (D) TOPOLOGY: linear (ii) MOLECULE TYPE: protein (xi) SEQUENCE DESCRIPTION: SEQ ID NO: 18:

```
Met Gln Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110
```

```
Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ile Glu Gly Arg Cys Asp Gly Ala Leu Asn Asp Leu Cys Ile Lys Val
450                 455                 460

Asn Asn Trp Asp Leu Phe Phe Ser Pro Ser Glu Asp Asn Phe Thr Asn
465                 470                 475                 480

Asp Leu Asn Lys Gly Glu Ile Thr Ser Asp Thr Asn Ile Glu Ala
                485                 490                 495

Ala Glu Glu Asn Ile Ser Leu Asp Leu Ile Gln Gln Tyr Tyr Leu Thr
                500                 505                 510

Phe Asn Phe Asp Asn Glu Pro Glu Asn Ile Ser Ile Glu Asn Leu Ser
                515                 520                 525

Ser Asp Ile Ile Gly Gln Leu Glu Leu Met Pro Asn Ile Glu Arg Phe
```

-continued

```
              530             535             540
Pro Asn Gly Lys Lys Tyr Glu Leu Asp Lys Tyr Thr Met Phe His Tyr
545             550             555             560

Leu Arg Ala Gln Glu Phe Glu His Gly Lys Ser Arg Ile Ala Leu Thr
                565             570             575

Asn Ser Val Asn Glu Ala Leu Leu Asn Pro Ser Arg Val Tyr Thr Phe
            580             585             590

Phe Ser Ser Asp Tyr Val Lys Lys Val Asn Lys Ala Thr Glu Ala Ala
        595             600             605

Met Phe Leu Gly Trp Val Glu Gln Leu Val Tyr Asp Phe Thr Asp Glu
    610             615             620

Thr Ser Glu Val Ser Thr Thr Asp Lys Ile Ala Asp Ile Thr Ile Ile
625             630             635             640

Ile Pro Tyr Ile Gly Pro Ala Leu Asn Ile Gly Asn Met Leu Tyr Lys
                645             650             655

Asp Asp Phe Val Gly Ala Leu Ile Phe Ser Gly Ala Val Ile Leu Leu
            660             665             670

Glu Phe Ile Pro Glu Ile Ala Ile Pro Val Leu Gly Thr Phe Ala Leu
        675             680             685

Val Ser Tyr Ile Ala Asn Lys Val Leu Thr Val Gln Thr Ile Asp Asn
690             695             700

Ala Leu Ser Lys Arg Asn Glu Lys Trp Asp Glu Val Tyr Lys Tyr Ile
705             710             715             720

Val Thr Asn Trp Leu Ala Lys Val Asn Thr Gln Ile Asp Leu Ile Arg
                725             730             735

Lys Lys Met Lys Glu Ala Leu Glu Asn Gln Ala Glu Ala Thr Lys Ala
            740             745             750

Ile Ile Asn Tyr Gln Tyr Asn Gln Tyr Thr Glu Glu Lys Asn Asn
        755             760             765

Ile Asn Phe Asn Ile Asp Asp Leu Ser Ser Lys Leu Asn Glu Ser Ile
    770             775             780

Asn Lys Ala Met Ile Asn Ile Asn Lys Phe Leu Asn Gln Cys Ser Val
785             790             795             800

Ser Tyr Leu Met Asn Ser Met Ile Pro Tyr Gly Val Lys Arg Leu Glu
                805             810             815

Asp Phe Asp Ala Ser Leu Lys Asp Ala Leu Leu Lys Tyr Ile Tyr Asp
            820             825             830

Asn Arg Gly Thr Leu Ile Gly Gln Val Asp Arg Leu Lys Asp Lys Val
        835             840             845

Asn Asn Thr Leu Ser Thr Asp Ile Pro Phe Gln Leu Ser Lys Tyr Val
    850             855             860

Asp Asn Gln Arg Leu Leu Ser Thr Phe Thr Glu Tyr Ile Lys Ser Gly
865             870             875             880

Leu Asn Ser Pro Gly Ala Ala His Tyr Ala Gln His Asp Glu Ala Val
                885             890             895

Asp Asn Lys Phe Asn Lys Glu Gln Gln Asn Ala Phe Tyr Glu Ile Leu
            900             905             910

His Leu Pro Asn Leu Asn Glu Glu Gln Arg Asn Ala Phe Ile Gln Ser
        915             920             925

Leu Lys Asp Asp Pro Ser Gln Ser Ala Asn Leu Leu Ala Glu Ala Lys
    930             935             940

Lys Leu Asn Asp Ala Gln Ala Pro Lys Val Asp Asn Lys Phe Asn Lys
945             950             955             960
```

```
Glu Gln Gln Asn Ala Phe Tyr Glu Ile Leu His Leu Pro Asn Leu Asn
            965                 970                 975

Glu Glu Gln Arg Asn Ala Phe Ile Gln Ser Leu Lys Asp Asp Pro Ser
            980                 985                 990

Gln Ser Ala Asn Leu Leu Ala Glu Ala Lys Lys Leu Asn Asp Ala Gln
            995                1000                1005

Ala Pro Lys Val Asp
     1010

(2) INFORMATION FOR SEQ ID NO: 19:

(i) SEQUENCE CHARACTERISTICS:
        (A) LENGTH: 3509 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..3509

(xi) SEQUENCE DESCRIPTION: SEQ ID NO: 19:

ATG CCA GTT ACA ATA AAT AAT TTT AAT TAT AAT GAT CCT ATT GAT AAT        48
Met Pro Val Thr Ile Asn Asn Phe Asn Tyr Asn Asp Pro Ile Asp Asn
 1               5                  10                  15

AAT AAT ATT ATT ATG ATG GAG CCT CCA TTT GCG AGA GGT ACG GGG AGA        96
Asn Asn Ile Ile Met Met Glu Pro Pro Phe Ala Arg Gly Thr Gly Arg
                20                  25                  30

TAT TAT AAA GCT TTT AAA ATC ACA GAT CGT ATT TGG ATA ATA CCG GAA       144
Tyr Tyr Lys Ala Phe Lys Ile Thr Asp Arg Ile Trp Ile Ile Pro Glu
            35                  40                  45

AGA TAT ACT TTT GGA TAT AAA CCT GAG GAT TTT AAT AAA AGT TCC GGT       192
Arg Tyr Thr Phe Gly Tyr Lys Pro Glu Asp Phe Asn Lys Ser Ser Gly
         50                  55                  60

ATT TTT AAT AGA GAT GTT TGT GAA TAT TAT GAT CCA GAT TAC TTA AAT       240
Ile Phe Asn Arg Asp Val Cys Glu Tyr Tyr Asp Pro Asp Tyr Leu Asn
 65                  70                  75                  80

ACT AAT GAT AAA AAG AAT ATA TTT TTA CAA ACA ATG ATC AAG TTA TTT       288
Thr Asn Asp Lys Lys Asn Ile Phe Leu Gln Thr Met Ile Lys Leu Phe
                 85                  90                  95

AAT AGA ATC AAA TCA AAA CCA TTG GGT GAA AAG TTA TTA GAG ATG ATT       336
Asn Arg Ile Lys Ser Lys Pro Leu Gly Glu Lys Leu Leu Glu Met Ile
            100                 105                 110

ATA AAT GGT ATA CCT TAT CTT GGA GAT AGA CGT GTT CCA CTC GAA GAG       384
Ile Asn Gly Ile Pro Tyr Leu Gly Asp Arg Arg Val Pro Leu Glu Glu
        115                 120                 125

TTT AAC ACA AAC ATT GCT AGT GTA ACT GTT AAT AAA TTA ATC AGT AAT       432
Phe Asn Thr Asn Ile Ala Ser Val Thr Val Asn Lys Leu Ile Ser Asn
    130                 135                 140

CCA GGA GAA GTG GAG CGA AAA AAA GGT ATT TTC GCA AAT TTA ATA ATA       480
Pro Gly Glu Val Glu Arg Lys Lys Gly Ile Phe Ala Asn Leu Ile Ile
145                 150                 155                 160

TTT GGA CCT GGG CCA GTT TTA AAT GAA AAT GAG ACT ATA GAT ATA GGT       528
Phe Gly Pro Gly Pro Val Leu Asn Glu Asn Glu Thr Ile Asp Ile Gly
                165                 170                 175

ATA CAA AAT CAT TTT GCA TCA AGG GAA GGC TTC GGG GGT ATA ATG CAA       576
Ile Gln Asn His Phe Ala Ser Arg Glu Gly Phe Gly Gly Ile Met Gln
            180                 185                 190

ATG AAG TTT TGC CCA GAA TAT GTA AGC GTA TTT AAT AAT GTT CAA GAA       624
```

```
                Met Lys Phe Cys Pro Glu Tyr Val Ser Val Phe Asn Asn Val Gln Glu
                            195                 200                 205

AAC AAA GGC GCA AGT ATA TTT AAT AGA CGT GGA TAT TTT TCA GAT CCA              672
Asn Lys Gly Ala Ser Ile Phe Asn Arg Arg Gly Tyr Phe Ser Asp Pro
            210                 215                 220

GCC TTG ATA TTA ATG CAT GAA CTT ATA CAT GTT TTA CAT GGA TTA TAT              720
Ala Leu Ile Leu Met His Glu Leu Ile His Val Leu His Gly Leu Tyr
225                 230                 235                 240

GGC ATT AAA GTA GAT GAT TTA CCA ATT GTA CCA AAT GAA AAA AAA TTT              768
Gly Ile Lys Val Asp Asp Leu Pro Ile Val Pro Asn Glu Lys Lys Phe
            245                 250                 255

TTT ATG CAA TCT ACA GAT GCT ATA CAG GCA GAA GAA CTA TAT ACA TTT              816
Phe Met Gln Ser Thr Asp Ala Ile Gln Ala Glu Glu Leu Tyr Thr Phe
            260                 265                 270

GGA GGA CAA GAT CCC AGC ATC ATA ACT CCT TCT ACG GAT AAA AGT ATC              864
Gly Gly Gln Asp Pro Ser Ile Ile Thr Pro Ser Thr Asp Lys Ser Ile
            275                 280                 285

TAT GAT AAA GTT TTG CAA AAT TTT AGA GGG ATA GTT GAT AGA CTT AAC              912
Tyr Asp Lys Val Leu Gln Asn Phe Arg Gly Ile Val Asp Arg Leu Asn
        290                 295                 300

AAG GTT TTA GTT TGC ATA TCA GAT CCT AAC ATT AAT ATT AAT ATA TAT              960
Lys Val Leu Val Cys Ile Ser Asp Pro Asn Ile Asn Ile Asn Ile Tyr
305                 310                 315                 320

AAA AAT AAA TTT AAA GAT AAA TAT AAA TTC GTT GAA GAT TCT GAG GGA             1008
Lys Asn Lys Phe Lys Asp Lys Tyr Lys Phe Val Glu Asp Ser Glu Gly
                325                 330                 335

AAA TAT AGT ATA GAT GTA GAA AGT TTT GAT AAA TTA TAT AAA AGC TTA             1056
Lys Tyr Ser Ile Asp Val Glu Ser Phe Asp Lys Leu Tyr Lys Ser Leu
            340                 345                 350

ATG TTT GGT TTT ACA GAA ACT AAT ATA GCA GAA AAT TAT AAA ATA AAA             1104
Met Phe Gly Phe Thr Glu Thr Asn Ile Ala Glu Asn Tyr Lys Ile Lys
            355                 360                 365

ACT AGA GCT TCT TAT TTT AGT GAT TCC TTA CCA CCA GTA AAA ATA AAA             1152
Thr Arg Ala Ser Tyr Phe Ser Asp Ser Leu Pro Pro Val Lys Ile Lys
        370                 375                 380

AAT TTA TTA GAT AAT GAA ATC TAT ACT ATA GAG GAA GGG TTT AAT ATA             1200
Asn Leu Leu Asp Asn Glu Ile Tyr Thr Ile Glu Glu Gly Phe Asn Ile
385                 390                 395                 400

TCT GAT AAA GAT ATG GAA AAA GAA TAT AGA GGT CAG AAT AAA GCT ATA             1248
Ser Asp Lys Asp Met Glu Lys Glu Tyr Arg Gly Gln Asn Lys Ala Ile
                405                 410                 415

AAT AAA CAA GCT TAT GAA GAA ATT AGC AAG GAG CAT TTG GCT GTA TAT             1296
Asn Lys Gln Ala Tyr Glu Glu Ile Ser Lys Glu His Leu Ala Val Tyr
            420                 425                 430

AAG ATA CAA ATG TGT AAA AGT GTT AAA GCT CCA GGA ATA TGT ATT GAT             1344
Lys Ile Gln Met Cys Lys Ser Val Lys Ala Pro Gly Ile Cys Ile Asp
            435                 440                 445

GTT GAT AAT GAA GAT TTG TTC TTT ATA GCT GAT AAA AAT AGT TTT TCA             1392
Val Asp Asn Glu Asp Leu Phe Phe Ile Ala Asp Lys Asn Ser Phe Ser
450                 455                 460

GAT GAT TTA TCT AAA AAC GAA AGA ATA GAA TAT AAT ACA CAG AGT AAT             1440
Asp Asp Leu Ser Lys Asn Glu Arg Ile Glu Tyr Asn Thr Gln Ser Asn
465                 470                 475                 480

TAT ATA GAA AAT GAC TTC CCT ATA AAT GAA TTA ATT TTA GAT ACT GAT             1488
Tyr Ile Glu Asn Asp Phe Pro Ile Asn Glu Leu Ile Leu Asp Thr Asp
                485                 490                 495

TTA ATA AGT AAA ATA GAA TTA CCA AGT GAA AAT ACA GAA TCA CTT ACT             1536
Leu Ile Ser Lys Ile Glu Leu Pro Ser Glu Asn Thr Glu Ser Leu Thr
            500                 505                 510
```

```
GAT TTT AAT GTA GAT GTT CCA GTA TAT GAA AAA CAA CCC GCT ATA AAA        1584
Asp Phe Asn Val Asp Val Pro Val Tyr Glu Lys Gln Pro Ala Ile Lys
        515                 520                 525

AAA ATT TTT ACA GAT GAA AAT ACC ATC TTT CAA TAT TTA TAC TCT CAG        1632
Lys Ile Phe Thr Asp Glu Asn Thr Ile Phe Gln Tyr Leu Tyr Ser Gln
530                 535                 540

ACA TTT CCT CTA GAT ATA AGA GAT ATA AGT TTA ACA TCT TCA TTT GAT        1680
Thr Phe Pro Leu Asp Ile Arg Asp Ile Ser Leu Thr Ser Ser Phe Asp
545                 550                 555                 560

GAT GCA TTA TTA TTT TCT AAC AAA GTT TAT TCA TTT TTT TCT ATG GAT        1728
Asp Ala Leu Leu Phe Ser Asn Lys Val Tyr Ser Phe Phe Ser Met Asp
                565                 570                 575

TAT ATT AAA ACT GCT AAT AAA GTG GTA GAA GCA GGA TTA TTT GCA GGT        1776
Tyr Ile Lys Thr Ala Asn Lys Val Val Glu Ala Gly Leu Phe Ala Gly
        580                 585                 590

TGG GTG AAA CAG ATA GTA AAT GAT TTT GTA ATC GAA GCT AAT AAA AGC        1824
Trp Val Lys Gln Ile Val Asn Asp Phe Val Ile Glu Ala Asn Lys Ser
        595                 600                 605

AAT ACT ATG GAT AAA ATT GCA GAT ATA TCT CTA ATT GTT CCT TAT ATA        1872
Asn Thr Met Asp Lys Ile Ala Asp Ile Ser Leu Ile Val Pro Tyr Ile
610                 615                 620

GGA TTA GCT TTA AAT GTA GGA AAT GAA ACA GCT AAA GGA AAT TTT GAA        1920
Gly Leu Ala Leu Asn Val Gly Asn Glu Thr Ala Lys Gly Asn Phe Glu
625                 630                 635                 640

AAT GCT TTT GAG ATT GCA GGA GCC AGT ATT CTA CTA GAA TTT ATA CCA        1968
Asn Ala Phe Glu Ile Ala Gly Ala Ser Ile Leu Leu Glu Phe Ile Pro
                645                 650                 655

GAA CTT TTA ATA CCT GTA GTT GGA GCC TTT TTA TTA GAA TCA TAT ATT        2016
Glu Leu Leu Ile Pro Val Val Gly Ala Phe Leu Leu Glu Ser Tyr Ile
                660                 665                 670

GAC AAT AAA AAT AAA ATT ATT AAA ACA ATA GAT AAT GCT TTA ACT AAA        2064
Asp Asn Lys Asn Lys Ile Ile Lys Thr Ile Asp Asn Ala Leu Thr Lys
            675                 680                 685

AGA AAT GAA AAA TGG AGT GAT ATG TAC GGA TTA ATA GTA GCG CAA TGG        2112
Arg Asn Glu Lys Trp Ser Asp Met Tyr Gly Leu Ile Val Ala Gln Trp
        690                 695                 700

CTC TCA ACA GTT AAT ACT CAA TTT TAT ACA ATA AAA GAG GGA ATG TAT        2160
Leu Ser Thr Val Asn Thr Gln Phe Tyr Thr Ile Lys Glu Gly Met Tyr
705                 710                 715                 720

AAG GCT TTA AAT TAT CAA GCA CAA GCA TTG GAA GAA ATA ATA AAA TAC        2208
Lys Ala Leu Asn Tyr Gln Ala Gln Ala Leu Glu Glu Ile Ile Lys Tyr
                725                 730                 735

AGA TAT AAT ATA TAT TCT GAA AAA GAA AAG TCA AAT ATT AAC ATC GAT        2256
Arg Tyr Asn Ile Tyr Ser Glu Lys Glu Lys Ser Asn Ile Asn Ile Asp
            740                 745                 750

TTT AAT GAT ATA AAT TCT AAA CTT AAT GAG GGT ATT AAC CAA GCT ATA        2304
Phe Asn Asp Ile Asn Ser Lys Leu Asn Glu Gly Ile Asn Gln Ala Ile
        755                 760                 765

GAT AAT ATA AAT AAT TTT ATA AAT GGA TGT TCT GTA TCA TAT TTA ATG        2352
Asp Asn Ile Asn Asn Phe Ile Asn Gly Cys Ser Val Ser Tyr Leu Met
770                 775                 780

AAA AAA ATG ATT CCA TTA GCT GTA GAA AAA TTA CTA GAC TTT GAT AAT        2400
Lys Lys Met Ile Pro Leu Ala Val Glu Lys Leu Leu Asp Phe Asp Asn
785                 790                 795                 800

ACT CTC AAA AAA AAT TTG TTA AAT TAT ATA GAT GAA AAT AAA TTA TAT        2448
Thr Leu Lys Lys Asn Leu Leu Asn Tyr Ile Asp Glu Asn Lys Leu Tyr
                805                 810                 815

TTG ATT GGA AGT GCA GAA TAT GAA AAA TCA AAA GTA AAT AAA TAC TTG        2496
Leu Ile Gly Ser Ala Glu Tyr Glu Lys Ser Lys Val Asn Lys Tyr Leu
        820                 825                 830
```

```
AAA ACC ATT ATG CCG TTT GAT CTT TCA ATA TAT ACC AAT GAT ACA ATA    2544
Lys Thr Ile Met Pro Phe Asp Leu Ser Ile Tyr Thr Asn Asp Thr Ile
        835                 840                 845

CTA ATA GAA ATG TTT AAT AAA TAT AAT AGC GAA ATT TTA AAT AAT ATT    2592
Leu Ile Glu Met Phe Asn Lys Tyr Asn Ser Glu Ile Leu Asn Asn Ile
        850                 855                 860

ATC TTA AAT TTA AGA TAT AAG GAT AAT AAT TTA ATA GAT TTA TCA GGA    2640
Ile Leu Asn Leu Arg Tyr Lys Asp Asn Asn Leu Ile Asp Leu Ser Gly
865                 870                 875                 880

TAT GGG GCA AAG GTA GAG GTA TAT GAT GGA GTC GAG CTT AAT GAT AAA    2688
Tyr Gly Ala Lys Val Glu Val Tyr Asp Gly Val Glu Leu Asn Asp Lys
                885                 890                 895

AAT CAA TTT AAA TTA ACT AGT TCA GCA AAT AGT AAG ATT AGA GTG ACT    2736
Asn Gln Phe Lys Leu Thr Ser Ser Ala Asn Ser Lys Ile Arg Val Thr
        900                 905                 910

CAA AAT CAG AAT ATC ATA TTT AAT AGT GTG TTC CTT GAT TTT AGC GTT    2784
Gln Asn Gln Asn Ile Ile Phe Asn Ser Val Phe Leu Asp Phe Ser Val
        915                 920                 925

AGC TTT TGG ATA AGA ATA CCT AAA TAT AAG AAT GAT GGT ATA CAA AAT    2832
Ser Phe Trp Ile Arg Ile Pro Lys Tyr Lys Asn Asp Gly Ile Gln Asn
        930                 935                 940

TAT ATT CAT AAT GAA TAT ACA ATA ATT AAT TGT ATG AAA AAT AAT TCG    2880
Tyr Ile His Asn Glu Tyr Thr Ile Ile Asn Cys Met Lys Asn Asn Ser
945                 950                 955                 960

GGC TGG AAA ATA TCT ATT AGG GGT AAT AGG ATA ATA TGG ACT TTA ATT    2928
Gly Trp Lys Ile Ser Ile Arg Gly Asn Arg Ile Ile Trp Thr Leu Ile
                965                 970                 975

GAT ATA AAT GGA AAA ACC AAA TCG GTA TTT TTT GAA TAT AAC ATA AGA    2976
Asp Ile Asn Gly Lys Thr Lys Ser Val Phe Phe Glu Tyr Asn Ile Arg
        980                 985                 990

GAA GAT ATA TCA GAG TAT ATA AAT AGA TGG TTT TTT GTA ACT ATT ACT    3024
Glu Asp Ile Ser Glu Tyr Ile Asn Arg Trp Phe Phe Val Thr Ile Thr
        995                 1000                1005

AAT AAT TTG AAT AAC GCT AAA ATT TAT ATT AAT GGT AAG CTA GAA TCA    3072
Asn Asn Leu Asn Asn Ala Lys Ile Tyr Ile Asn Gly Lys Leu Glu Ser
        1010                1015                1020

AAT ACA GAT ATT AAA GAT ATA AGA GAA GTT ATT GCT AAT GGT GAA ATA    3120
Asn Thr Asp Ile Lys Asp Ile Arg Glu Val Ile Ala Asn Gly Glu Ile
1025                1030                1035                1040

ATA TTT AAA TTA GAT GGT GAT ATA GAT AGA ACA CAA TTT ATT TGG ATG    3168
Ile Phe Lys Leu Asp Gly Asp Ile Asp Arg Thr Gln Phe Ile Trp Met
                1045                1050                1055

AAA TAT TTC AGT ATT TTT AAT ACG GAA TTA AGT CAA TCA AAT ATT GAA    3216
Lys Tyr Phe Ser Ile Phe Asn Thr Glu Leu Ser Gln Ser Asn Ile Glu
        1060                1065                1070

GAA AGA TAT AAA ATT CAA TCA TAT AGC GAA TAT TTA AAA GAT TTT TGG    3264
Glu Arg Tyr Lys Ile Gln Ser Tyr Ser Glu Tyr Leu Lys Asp Phe Trp
        1075                1080                1085

GGA AAT CCT TTA ATG TAC AAT AAA GAA TAT TAT ATG TTT AAT GCG GGG    3312
Gly Asn Pro Leu Met Tyr Asn Lys Glu Tyr Tyr Met Phe Asn Ala Gly
        1090                1095                1100

AAT AAA AAT TCA TAT ATT AAA CTA AAG AAA GAT TCA CCT GTA GGT GAA    3360
Asn Lys Asn Ser Tyr Ile Lys Leu Lys Lys Asp Ser Pro Val Gly Glu
1105                1110                1115                1120

ATT TTA ACA CGT AGC AAA TAT AAT CAA AAT TCT AAA TAT ATA AAT TAT    3408
Ile Leu Thr Arg Ser Lys Tyr Asn Gln Asn Ser Lys Tyr Ile Asn Tyr
                1125                1130                1135

AGA GAT TTA TAT ATT GGA GAA AAA TTT ATT ATA AGA AGA AAG TCA AAT    3456
Arg Asp Leu Tyr Ile Gly Glu Lys Phe Ile Ile Arg Arg Lys Ser Asn
```

```
                    1140              1145              1150
TCT CAA TCT ATA AAT GAT GAT ATA GTT AGA AAA GAA GAT TAT ATA TAT      3504
Ser Gln Ser Ile Asn Asp Asp Ile Val Arg Lys Glu Asp Tyr Ile Tyr
            1155              1160              1165

CTA GA                                                                3509
Leu
```

(2) INFORMATION FOR SEQ ID NO: 20:

(i) SEQUENCE CHARACTERISTICS:
        (A) LENGTH: 1169 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
                100                 105                 110

Ile Asn Gly Ile Pro Tyr Leu Gly Asp Arg Arg Val Pro Leu Glu Glu
            115                 120                 125

Phe Asn Thr Asn Ile Ala Ser Val Thr Val Asn Lys Leu Ile Ser Asn
        130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
```

-continued

```
305                 310                 315                 320
Lys Asn Lys Phe Lys Asp Lys Tyr Lys Phe Val Glu Asp Ser Glu Gly
                325                 330                 335
Lys Tyr Ser Ile Asp Val Glu Ser Phe Asp Lys Leu Tyr Lys Ser Leu
                340                 345                 350
Met Phe Gly Phe Thr Glu Thr Asn Ile Ala Glu Asn Tyr Lys Ile Lys
                355                 360                 365
Thr Arg Ala Ser Tyr Phe Ser Asp Ser Leu Pro Pro Val Lys Ile Lys
                370                 375                 380
Asn Leu Leu Asp Asn Glu Ile Tyr Thr Ile Glu Glu Gly Phe Asn Ile
385                 390                 395                 400
Ser Asp Lys Asp Met Glu Lys Glu Tyr Arg Gly Gln Asn Lys Ala Ile
                405                 410                 415
Asn Lys Gln Ala Tyr Glu Glu Ile Ser Lys Glu His Leu Ala Val Tyr
                420                 425                 430
Lys Ile Gln Met Cys Lys Ser Val Lys Ala Pro Gly Ile Cys Ile Asp
                435                 440                 445
Val Asp Asn Glu Asp Leu Phe Phe Ile Ala Asp Lys Asn Ser Phe Ser
450                 455                 460
Asp Asp Leu Ser Lys Asn Glu Arg Ile Glu Tyr Asn Thr Gln Ser Asn
465                 470                 475                 480
Tyr Ile Glu Asn Asp Phe Pro Ile Asn Glu Leu Ile Leu Asp Thr Asp
                485                 490                 495
Leu Ile Ser Lys Ile Glu Leu Pro Ser Glu Asn Thr Glu Ser Leu Thr
                500                 505                 510
Asp Phe Asn Val Asp Val Pro Val Tyr Glu Lys Gln Pro Ala Ile Lys
                515                 520                 525
Lys Ile Phe Thr Asp Glu Asn Thr Ile Phe Gln Tyr Leu Tyr Ser Gln
                530                 535                 540
Thr Phe Pro Leu Asp Ile Arg Asp Ile Ser Leu Thr Ser Ser Phe Asp
545                 550                 555                 560
Asp Ala Leu Leu Phe Ser Asn Lys Val Tyr Ser Phe Ser Met Asp
                565                 570                 575
Tyr Ile Lys Thr Ala Asn Lys Val Val Glu Ala Gly Leu Phe Ala Gly
                580                 585                 590
Trp Val Lys Gln Ile Val Asn Asp Phe Val Ile Glu Ala Asn Lys Ser
                595                 600                 605
Asn Thr Met Asp Lys Ile Ala Asp Ile Ser Leu Ile Val Pro Tyr Ile
                610                 615                 620
Gly Leu Ala Leu Asn Val Gly Asn Glu Thr Ala Lys Gly Asn Phe Glu
625                 630                 635                 640
Asn Ala Phe Glu Ile Ala Gly Ala Ser Ile Leu Leu Glu Phe Ile Pro
                645                 650                 655
Glu Leu Leu Ile Pro Val Val Gly Ala Phe Leu Leu Glu Ser Tyr Ile
                660                 665                 670
Asp Asn Lys Asn Lys Ile Ile Lys Thr Ile Asp Asn Ala Leu Thr Lys
                675                 680                 685
Arg Asn Glu Lys Trp Ser Asp Met Tyr Gly Leu Ile Val Ala Gln Trp
                690                 695                 700
Leu Ser Thr Val Asn Thr Gln Phe Tyr Thr Ile Lys Glu Gly Met Tyr
705                 710                 715                 720
Lys Ala Leu Asn Tyr Gln Ala Gln Ala Leu Glu Glu Ile Ile Lys Tyr
                725                 730                 735
```

-continued

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
            805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
            850                 855                 860

Ile Leu Asn Leu Arg Tyr Lys Asp Asn Leu Ile Asp Leu Ser Gly
865                 870                 875                 880

Tyr Gly Ala Lys Val Glu Val Tyr Asp Gly Val Glu Leu Asn Asp Lys
            885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
            965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
            995                 1000                1005

Asn Asn Leu Asn Asn Ala Lys Ile Tyr Ile Asn Gly Lys Leu Glu Ser
            1010                1015                1020

Asn Thr Asp Ile Lys Asp Ile Arg Glu Val Ile Ala Asn Gly Glu Ile
1025                1030                1035                1040

Ile Phe Lys Leu Asp Gly Asp Ile Asp Arg Thr Gln Phe Ile Trp Met
            1045                1050                1055

Lys Tyr Phe Ser Ile Phe Asn Thr Glu Leu Ser Gln Ser Asn Ile Glu
            1060                1065                1070

Glu Arg Tyr Lys Ile Gln Ser Tyr Ser Glu Tyr Leu Lys Asp Phe Trp
            1075                1080                1085

Gly Asn Pro Leu Met Tyr Asn Lys Glu Tyr Tyr Met Phe Asn Ala Gly
            1090                1095                1100

Asn Lys Asn Ser Tyr Ile Lys Leu Lys Lys Asp Ser Pro Val Gly Glu
1105                1110                1115                1120

Ile Leu Thr Arg Ser Lys Tyr Asn Gln Asn Ser Lys Tyr Ile Asn Tyr
            1125                1130                1135

Arg Asp Leu Tyr Ile Gly Glu Lys Phe Ile Ile Arg Arg Lys Ser Asn
            1140                1145                1150

```
Ser Gln Ser Ile Asn Asp Asp Ile Val Arg Lys Glu Asp Tyr Ile Tyr
        1155                1160                1165

Leu (2) INFORMATION FOR SEQ ID NO: 21:

(i) SEQUENCE CHARACTERISTICS:
        (A) LENGTH: 2574 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2574

(xi) SEQUENCE DESCRIPTION: SEQ ID NO: 21:

ATG CCA GTT ACA ATA AAT AAT TTT AAT TAT AAT GAT CCT ATT GAT AAT        48
Met Pro Val Thr Ile Asn Asn Phe Asn Tyr Asn Asp Pro Ile Asp Asn
 1               5                  10                  15

AAT AAT ATT ATT ATG ATG GAG CCT CCA TTT GCG AGA GGT ACG GGG AGA        96
Asn Asn Ile Ile Met Met Glu Pro Pro Phe Ala Arg Gly Thr Gly Arg
            20                  25                  30

TAT TAT AAA GCT TTT AAA ATC ACA GAT CGT ATT TGG ATA ATA CCG GAA       144
Tyr Tyr Lys Ala Phe Lys Ile Thr Asp Arg Ile Trp Ile Ile Pro Glu
        35                  40                  45

AGA TAT ACT TTT GGA TAT AAA CCT GAG GAT TTT AAT AAA AGT TCC GGT       192
Arg Tyr Thr Phe Gly Tyr Lys Pro Glu Asp Phe Asn Lys Ser Ser Gly
    50                  55                  60

ATT TTT AAT AGA GAT GTT TGT GAA TAT TAT GAT CCA GAT TAC TTA AAT       240
Ile Phe Asn Arg Asp Val Cys Glu Tyr Tyr Asp Pro Asp Tyr Leu Asn
65                  70                  75                  80

ACT AAT GAT AAA AAG AAT ATA TTT TTA CAA ACA ATG ATC AAG TTA TTT       288
Thr Asn Asp Lys Lys Asn Ile Phe Leu Gln Thr Met Ile Lys Leu Phe
                85                  90                  95

AAT AGA ATC AAA TCA AAA CCA TTG GGT GAA AAG TTA TTA GAG ATG ATT       336
Asn Arg Ile Lys Ser Lys Pro Leu Gly Glu Lys Leu Leu Glu Met Ile
            100                 105                 110

ATA AAT GGT ATA CCT TAT CTT GGA GAT AGA CGT GTT CCA CTC GAA GAG       384
Ile Asn Gly Ile Pro Tyr Leu Gly Asp Arg Arg Val Pro Leu Glu Glu
        115                 120                 125

TTT AAC ACA AAC ATT GCT AGT GTA ACT GTT AAT AAA TTA ATC AGT AAT       432
Phe Asn Thr Asn Ile Ala Ser Val Thr Val Asn Lys Leu Ile Ser Asn
    130                 135                 140

CCA GGA GAA GTG GAG CGA AAA AAA GGT ATT TTC GCA AAT TTA ATA ATA       480
Pro Gly Glu Val Glu Arg Lys Lys Gly Ile Phe Ala Asn Leu Ile Ile
145                 150                 155                 160

TTT GGA CCT GGG CCA GTT TTA AAT GAA AAT GAG ACT ATA GAT ATA GGT       528
Phe Gly Pro Gly Pro Val Leu Asn Glu Asn Glu Thr Ile Asp Ile Gly
                165                 170                 175

ATA CAA AAT CAT TTT GCA TCA AGG GAA GGC TTC GGG GGT ATA ATG CAA       576
Ile Gln Asn His Phe Ala Ser Arg Glu Gly Phe Gly Gly Ile Met Gln
            180                 185                 190

ATG AAG TTT TGC CCA GAA TAT GTA AGC GTA TTT AAT AAT GTT CAA GAA       624
Met Lys Phe Cys Pro Glu Tyr Val Ser Val Phe Asn Asn Val Gln Glu
        195                 200                 205

AAC AAA GGC GCA AGT ATA TTT AAT AGA CGT GGA TAT TTT TCA GAT CCA       672
Asn Lys Gly Ala Ser Ile Phe Asn Arg Arg Gly Tyr Phe Ser Asp Pro
    210                 215                 220

GCC TTG ATA TTA ATG CAT GAA CTT ATA CAT GTT TTA CAT GGA TTA TAT       720
```

-continued

```
Ala Leu Ile Leu Met His Glu Leu Ile His Val Leu His Gly Leu Tyr
225                 230                 235                 240

GGC ATT AAA GTA GAT GAT TTA CCA ATT GTA CCA AAT GAA AAA AAA TTT      768
Gly Ile Lys Val Asp Asp Leu Pro Ile Val Pro Asn Glu Lys Lys Phe
                    245                 250                 255

TTT ATG CAA TCT ACA GAT GCT ATA CAG GCA GAA GAA CTA TAT ACA TTT      816
Phe Met Gln Ser Thr Asp Ala Ile Gln Ala Glu Glu Leu Tyr Thr Phe
                260                 265                 270

GGA GGA CAA GAT CCC AGC ATC ATA ACT CCT TCT ACG GAT AAA AGT ATC      864
Gly Gly Gln Asp Pro Ser Ile Ile Thr Pro Ser Thr Asp Lys Ser Ile
                275                 280                 285

TAT GAT AAA GTT TTG CAA AAT TTT AGA GGG ATA GTT GAT AGA CTT AAC      912
Tyr Asp Lys Val Leu Gln Asn Phe Arg Gly Ile Val Asp Arg Leu Asn
290                 295                 300

AAG GTT TTA GTT TGC ATA TCA GAT CCT AAC ATT AAT ATT AAT ATA TAT      960
Lys Val Leu Val Cys Ile Ser Asp Pro Asn Ile Asn Ile Asn Ile Tyr
305                 310                 315                 320

AAA AAT AAA TTT AAA GAT AAA TAT AAA TTC GTT GAA GAT TCT GAG GGA     1008
Lys Asn Lys Phe Lys Asp Lys Tyr Lys Phe Val Glu Asp Ser Glu Gly
                325                 330                 335

AAA TAT AGT ATA GAT GTA GAA AGT TTT GAT AAA TTA TAT AAA AGC TTA     1056
Lys Tyr Ser Ile Asp Val Glu Ser Phe Asp Lys Leu Tyr Lys Ser Leu
                340                 345                 350

ATG TTT GGT TTT ACA GAA ACT AAT ATA GCA GAA AAT TAT AAA ATA AAA     1104
Met Phe Gly Phe Thr Glu Thr Asn Ile Ala Glu Asn Tyr Lys Ile Lys
                355                 360                 365

ACT AGA GCT TCT TAT TTT AGT GAT TCC TTA CCA CCA GTA AAA ATA AAA     1152
Thr Arg Ala Ser Tyr Phe Ser Asp Ser Leu Pro Pro Val Lys Ile Lys
370                 375                 380

AAT TTA TTA GAT AAT GAA ATC TAT ACT ATA GAG GAA GGG TTT AAT ATA     1200
Asn Leu Leu Asp Asn Glu Ile Tyr Thr Ile Glu Glu Gly Phe Asn Ile
385                 390                 395                 400

TCT GAT AAA GAT ATG GAA AAA GAA TAT AGA GGT CAG AAT AAA GCT ATA     1248
Ser Asp Lys Asp Met Glu Lys Glu Tyr Arg Gly Gln Asn Lys Ala Ile
                405                 410                 415

AAT AAA CAA GCT TAT GAA GAA ATT AGC AAG GAG CAT TTG GCT GTA TAT     1296
Asn Lys Gln Ala Tyr Glu Glu Ile Ser Lys Glu His Leu Ala Val Tyr
                420                 425                 430

AAG ATA CAA ATG TGT AAA AGT GTT AAA GCT CCA GGA ATA TGT ATT GAT     1344
Lys Ile Gln Met Cys Lys Ser Val Lys Ala Pro Gly Ile Cys Ile Asp
                435                 440                 445

GTT GAT AAT GAA GAT TTG TTC TTT ATA GCT GAT AAA AAT AGT TTT TCA     1392
Val Asp Asn Glu Asp Leu Phe Phe Ile Ala Asp Lys Asn Ser Phe Ser
450                 455                 460

GAT GAT TTA TCT AAA AAC GAA AGA ATA GAA TAT AAT ACA CAG AGT AAT     1440
Asp Asp Leu Ser Lys Asn Glu Arg Ile Glu Tyr Asn Thr Gln Ser Asn
465                 470                 475                 480

TAT ATA GAA AAT GAC TTC CCT ATA AAT GAA TTA ATT TTA GAT ACT GAT     1488
Tyr Ile Glu Asn Asp Phe Pro Ile Asn Glu Leu Ile Leu Asp Thr Asp
                485                 490                 495

TTA ATA AGT AAA ATA GAA TTA CCA AGT GAA AAT ACA GAA TCA CTT ACT     1536
Leu Ile Ser Lys Ile Glu Leu Pro Ser Glu Asn Thr Glu Ser Leu Thr
                500                 505                 510

GAT TTT AAT GTA GAT GTT CCA GTA TAT GAA AAA CAA CCC GCT ATA AAA     1584
Asp Phe Asn Val Asp Val Pro Val Tyr Glu Lys Gln Pro Ala Ile Lys
                515                 520                 525

AAA ATT TTT ACA GAT GAA AAT ACC ATC TTT CAA TAT TTA TAC TCT CAG     1632
Lys Ile Phe Thr Asp Glu Asn Thr Ile Phe Gln Tyr Leu Tyr Ser Gln
530                 535                 540
```

```
ACA TTT CCT CTA GAT ATA AGA GAT ATA AGT TTA ACA TCT TCA TTT GAT      1680
Thr Phe Pro Leu Asp Ile Arg Asp Ile Ser Leu Thr Ser Ser Phe Asp
545                 550                 555                 560

GAT GCA TTA TTA TTT TCT AAC AAA GTT TAT TCA TTT TTT TCT ATG GAT      1728
Asp Ala Leu Leu Phe Ser Asn Lys Val Tyr Ser Phe Phe Ser Met Asp
                    565                 570                 575

TAT ATT AAA ACT GCT AAT AAA GTG GTA GAA GCA GGA TTA TTT GCA GGT      1776
Tyr Ile Lys Thr Ala Asn Lys Val Val Glu Ala Gly Leu Phe Ala Gly
                580                 585                 590

TGG GTG AAA CAG ATA GTA AAT GAT TTT GTA ATC GAA GCT AAT AAA AGC      1824
Trp Val Lys Gln Ile Val Asn Asp Phe Val Ile Glu Ala Asn Lys Ser
            595                 600                 605

AAT ACT ATG GAT AAA ATT GCA GAT ATA TCT CTA ATT GTT CCT TAT ATA      1872
Asn Thr Met Asp Lys Ile Ala Asp Ile Ser Leu Ile Val Pro Tyr Ile
        610                 615                 620

GGA TTA GCT TTA AAT GTA GGA AAT GAA ACA GCT AAA GGA AAT TTT GAA      1920
Gly Leu Ala Leu Asn Val Gly Asn Glu Thr Ala Lys Gly Asn Phe Glu
625                 630                 635                 640

AAT GCT TTT GAG ATT GCA GGA GCC AGT ATT CTA CTA GAA TTT ATA CCA      1968
Asn Ala Phe Glu Ile Ala Gly Ala Ser Ile Leu Leu Glu Phe Ile Pro
                    645                 650                 655

GAA CTT TTA ATA CCT GTA GTT GGA GCC TTT TTA TTA GAA TCA TAT ATT      2016
Glu Leu Leu Ile Pro Val Val Gly Ala Phe Leu Leu Glu Ser Tyr Ile
                660                 665                 670

GAC AAT AAA AAT AAA ATT ATT AAA ACA ATA GAT AAT GCT TTA ACT AAA      2064
Asp Asn Lys Asn Lys Ile Ile Lys Thr Ile Asp Asn Ala Leu Thr Lys
            675                 680                 685

AGA AAT GAA AAA TGG AGT GAT ATG TAC GGA TTA ATA GTA GCG CAA TGG      2112
Arg Asn Glu Lys Trp Ser Asp Met Tyr Gly Leu Ile Val Ala Gln Trp
        690                 695                 700

CTC TCA ACA GTT AAT ACT CAA TTT TAT ACA ATA AAA GAG GGA ATG TAT      2160
Leu Ser Thr Val Asn Thr Gln Phe Tyr Thr Ile Lys Glu Gly Met Tyr
705                 710                 715                 720

AAG GCT TTA AAT TAT CAA GCA CAA GCA TTG GAA GAA ATA ATA AAA TAC      2208
Lys Ala Leu Asn Tyr Gln Ala Gln Ala Leu Glu Glu Ile Ile Lys Tyr
                    725                 730                 735

AGA TAT AAT ATA TAT TCT GAA AAA GAA AAG TCA AAT ATT AAC ATC GAT      2256
Arg Tyr Asn Ile Tyr Ser Glu Lys Glu Lys Ser Asn Ile Asn Ile Asp
                740                 745                 750

TTT AAT GAT ATA AAT TCT AAA CTT AAT GAG GGT ATT AAC CAA GCT ATA      2304
Phe Asn Asp Ile Asn Ser Lys Leu Asn Glu Gly Ile Asn Gln Ala Ile
            755                 760                 765

GAT AAT ATA AAT AAT TTT ATA AAT GGA TGT TCT GTA TCA TAT TTA ATG      2352
Asp Asn Ile Asn Asn Phe Ile Asn Gly Cys Ser Val Ser Tyr Leu Met
        770                 775                 780

AAA AAA ATG ATT CCA TTA GCT GTA GAA AAA TTA CTA GAC TTT GAT AAT      2400
Lys Lys Met Ile Pro Leu Ala Val Glu Lys Leu Leu Asp Phe Asp Asn
785                 790                 795                 800

ACT CTC AAA AAA AAT TTG TTA AAT TAT ATA GAT GAA AAT AAA TTA TAT      2448
Thr Leu Lys Lys Asn Leu Leu Asn Tyr Ile Asp Glu Asn Lys Leu Tyr
                    805                 810                 815

TTG ATT GGA AGT GCA GAA TAT GAA AAA TCA AAA GTA AAT AAA TAC TTG      2496
Leu Ile Gly Ser Ala Glu Tyr Glu Lys Ser Lys Val Asn Lys Tyr Leu
                820                 825                 830

AAA ACC ATT ATG CCG TTT GAT CTT TCA ATA TAT ACC AAT GAT ACA ATA      2544
Lys Thr Ile Met Pro Phe Asp Leu Ser Ile Tyr Thr Asn Asp Thr Ile
            835                 840                 845

CTA ATA GAA ATG TTT AAT AAA TAT AAT AGC                              2574
Leu Ile Glu Met Phe Asn Lys Tyr Asn Ser
        850                 855
```

(2) INFORMATION FOR SEQ ID NO: 22:

(i) SEQUENCE CHARACTERISTICS:
        (A) LENGTH: 858 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350
```

-continued

```
Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
```

```
                    770              775              780
Lys Lys Met Ile Pro Leu Ala Val Glu Lys Leu Leu Asp Phe Asp Asn
785              790              795              800

Thr Leu Lys Lys Asn Leu Leu Asn Tyr Ile Asp Glu Asn Lys Leu Tyr
                 805              810              815

Leu Ile Gly Ser Ala Glu Tyr Glu Lys Ser Lys Val Asn Lys Tyr Leu
                820              825              830

Lys Thr Ile Met Pro Phe Asp Leu Ser Ile Tyr Thr Asn Asp Thr Ile
                835              840              845

Leu Ile Glu Met Phe Asn Lys Tyr Asn Ser
                850              855

(2) INFORMATION FOR SEQ ID NO: 23:

(i) SEQUENCE CHARACTERISTICS:
        (A) LENGTH: 1644 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..1644

(xi) SEQUENCE DESCRIPTION: SEQ ID NO: 23:

ATG CCA GTT ACA ATA AAT AAT TTT AAT TAT AAT GAT CCT ATT GAT AAT      48
Met Pro Val Thr Ile Asn Asn Phe Asn Tyr Asn Asp Pro Ile Asp Asn
 1               5                  10                  15

AAT AAT ATT ATT ATG ATG GAG CCT CCA TTT GCG AGA GGT ACG GGG AGA      96
Asn Asn Ile Ile Met Met Glu Pro Pro Phe Ala Arg Gly Thr Gly Arg
                20                  25                  30

TAT TAT AAA GCT TTT AAA ATC ACA GAT CGT ATT TGG ATA ATA CCG GAA     144
Tyr Tyr Lys Ala Phe Lys Ile Thr Asp Arg Ile Trp Ile Ile Pro Glu
            35                  40                  45

AGA TAT ACT TTT GGA TAT AAA CCT GAG GAT TTT AAT AAA AGT TCC GGT     192
Arg Tyr Thr Phe Gly Tyr Lys Pro Glu Asp Phe Asn Lys Ser Ser Gly
         50                  55                  60

ATT TTT AAT AGA GAT GTT TGT GAA TAT TAT GAT CCA GAT TAC TTA AAT     240
Ile Phe Asn Arg Asp Val Cys Glu Tyr Tyr Asp Pro Asp Tyr Leu Asn
 65                  70                  75                  80

ACT AAT GAT AAA AAG AAT ATA TTT TTA CAA ACA ATG ATC AAG TTA TTT     288
Thr Asn Asp Lys Lys Asn Ile Phe Leu Gln Thr Met Ile Lys Leu Phe
                 85                  90                  95

AAT AGA ATC AAA TCA AAA CCA TTG GGT GAA AAG TTA TTA GAG ATG ATT     336
Asn Arg Ile Lys Ser Lys Pro Leu Gly Glu Lys Leu Leu Glu Met Ile
            100                 105                 110

ATA AAT GGT ATA CCT TAT CTT GGA GAT AGA CGT GTT CCA CTC GAA GAG     384
Ile Asn Gly Ile Pro Tyr Leu Gly Asp Arg Arg Val Pro Leu Glu Glu
        115                 120                 125

TTT AAC ACA AAC ATT GCT AGT GTA ACT GTT AAT AAA TTA ATC AGT AAT     432
Phe Asn Thr Asn Ile Ala Ser Val Thr Val Asn Lys Leu Ile Ser Asn
    130                 135                 140

CCA GGA GAA GTG GAG CGA AAA AAA GGT ATT TTC GCA AAT TTA ATA ATA     480
Pro Gly Glu Val Glu Arg Lys Lys Gly Ile Phe Ala Asn Leu Ile Ile
145                 150                 155                 160

TTT GGA CCT GGG CCA GTT TTA AAT GAA AAT GAG ACT ATA GAT ATA GGT     528
Phe Gly Pro Gly Pro Val Leu Asn Glu Asn Glu Thr Ile Asp Ile Gly
                165                 170                 175

ATA CAA AAT CAT TTT GCA TCA AGG GAA GGC TTC GGG GGT ATA ATG CAA     576
```

```
Ile Gln Asn His Phe Ala Ser Arg Glu Gly Phe Gly Ile Met Gln
            180                 185                 190

ATG AAG TTT TGC CCA GAA TAT GTA AGC GTA TTT AAT AAT GTT CAA GAA        624
Met Lys Phe Cys Pro Glu Tyr Val Ser Val Phe Asn Asn Val Gln Glu
        195                 200                 205

AAC AAA GGC GCA AGT ATA TTT AAT AGA CGT GGA TAT TTT TCA GAT CCA        672
Asn Lys Gly Ala Ser Ile Phe Asn Arg Arg Gly Tyr Phe Ser Asp Pro
    210                 215                 220

GCC TTG ATA TTA ATG CAT GAA CTT ATA CAT GTT TTA CAT GGA TTA TAT        720
Ala Leu Ile Leu Met His Glu Leu Ile His Val Leu His Gly Leu Tyr
225                 230                 235                 240

GGC ATT AAA GTA GAT GAT TTA CCA ATT GTA CCA AAT GAA AAA AAA TTT        768
Gly Ile Lys Val Asp Asp Leu Pro Ile Val Pro Asn Glu Lys Lys Phe
                245                 250                 255

TTT ATG CAA TCT ACA GAT GCT ATA CAG GCA GAA GAA CTA TAT ACA TTT        816
Phe Met Gln Ser Thr Asp Ala Ile Gln Ala Glu Glu Leu Tyr Thr Phe
            260                 265                 270

GGA GGA CAA GAT CCC AGC ATC ATA ACT CCT TCT ACG GAT AAA AGT ATC        864
Gly Gly Gln Asp Pro Ser Ile Ile Thr Pro Ser Thr Asp Lys Ser Ile
        275                 280                 285

TAT GAT AAA GTT TTG CAA AAT TTT AGA GGG ATA GTT GAT AGA CTT AAC        912
Tyr Asp Lys Val Leu Gln Asn Phe Arg Gly Ile Val Asp Arg Leu Asn
    290                 295                 300

AAG GTT TTA GTT TGC ATA TCA GAT CCT AAC ATT AAT ATT AAT ATA TAT        960
Lys Val Leu Val Cys Ile Ser Asp Pro Asn Ile Asn Ile Asn Ile Tyr
305                 310                 315                 320

AAA AAT AAA TTT AAA GAT AAA TAT AAA TTC GTT GAA GAT TCT GAG GGA       1008
Lys Asn Lys Phe Lys Asp Lys Tyr Lys Phe Val Glu Asp Ser Glu Gly
                325                 330                 335

AAA TAT AGT ATA GAT GTA GAA AGT TTT GAT AAA TTA TAT AAA AGC TTA       1056
Lys Tyr Ser Ile Asp Val Glu Ser Phe Asp Lys Leu Tyr Lys Ser Leu
            340                 345                 350

ATG TTT GGT TTT ACA GAA ACT AAT ATA GCA GAA AAT TAT AAA ATA AAA       1104
Met Phe Gly Phe Thr Glu Thr Asn Ile Ala Glu Asn Tyr Lys Ile Lys
        355                 360                 365

ACT AGA GCT TCT TAT TTT AGT GAT TCC TTA CCA CCA GTA AAA ATA AAA       1152
Thr Arg Ala Ser Tyr Phe Ser Asp Ser Leu Pro Pro Val Lys Ile Lys
    370                 375                 380

AAT TTA TTA GAT AAT GAA ATC TAT ACT ATA GAG GAA GGG TTT AAT ATA       1200
Asn Leu Leu Asp Asn Glu Ile Tyr Thr Ile Glu Glu Gly Phe Asn Ile
385                 390                 395                 400

TCT GAT AAA GAT ATG GAA AAA GAA TAT AGA GGT CAG AAT AAA GCT ATA       1248
Ser Asp Lys Asp Met Glu Lys Glu Tyr Arg Gly Gln Asn Lys Ala Ile
                405                 410                 415

AAT AAA CAA GCT TAT GAA GAA ATT AGC AAG GAG CAT TTG GCT GTA TAT       1296
Asn Lys Gln Ala Tyr Glu Glu Ile Ser Lys Glu His Leu Ala Val Tyr
            420                 425                 430

AAG ATA CAA ATG TGT AAA AGT GTT AAA GCT CCA GGA ATA TGT ATT GAT       1344
Lys Ile Gln Met Cys Lys Ser Val Lys Ala Pro Gly Ile Cys Ile Asp
        435                 440                 445

GTT GAT AAT GAA GAT TTG TTC TTT ATA GCT GAT AAA AAT AGT TTT TCA       1392
Val Asp Asn Glu Asp Leu Phe Phe Ile Ala Asp Lys Asn Ser Phe Ser
    450                 455                 460

GAT GAT TTA TCT AAA AAC GAA AGA ATA GAA TAT AAT ACA CAG AGT AAT       1440
Asp Asp Leu Ser Lys Asn Glu Arg Ile Glu Tyr Asn Thr Gln Ser Asn
465                 470                 475                 480

TAT ATA GAA AAT GAC TTC CCT ATA AAT GAA TTA ATT TTA GAT ACT GAT       1488
Tyr Ile Glu Asn Asp Phe Pro Ile Asn Glu Leu Ile Leu Asp Thr Asp
                485                 490                 495
```

```
TTA ATA AGT AAA ATA GAA TTA CCA AGT GAA AAT ACA GAA TCA CTT ACT        1536
Leu Ile Ser Lys Ile Glu Leu Pro Ser Glu Asn Thr Glu Ser Leu Thr
        500                 505                 510

GAT TTT AAT GTA GAT GTT CCA GTA TAT GAA AAA CAA CCC GCT ATA AAA        1584
Asp Phe Asn Val Asp Val Pro Val Tyr Glu Lys Gln Pro Ala Ile Lys
        515                 520                 525

AAA ATT TTT ACA GAT GAA AAT ACC ATC TTT CAA TAT TTA TAC TCT CAG        1632
Lys Ile Phe Thr Asp Glu Asn Thr Ile Phe Gln Tyr Leu Tyr Ser Gln
        530                 535                 540

ACA TTT CCT CTA                                                        1644
Thr Phe Pro Leu
545

(2) INFORMATION FOR SEQ ID NO: 24:

(i) SEQUENCE CHARACTERISTICS:
        (A) LENGTH: 548 amino acids
        (B) TYPE: amino acid
        (D) TOPOLOGY: linear (ii) MOLECULE TYPE: protein (xi) SEQUENCE DESCRIPTION: SEQ ID NO: 24:

Met Pro Val Thr Ile Asn Asn Phe Asn Tyr Asn Asp Pro Ile Asp Asn
 1               5                  10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270
```

-continued

```
Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu
545
```

(2) INFORMATION FOR SEQ ID NO: 25:

(i) SEQUENCE CHARACTERISTICS:
        (A) LENGTH: 2616 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2616

(xi) SEQUENCE DESCRIPTION: SEQ ID NO: 25:

```
ATG CAG TTC GTG AAC AAG CAG TTC AAC TAT AAG GAC CCT GTA AAC GGT      48
Met Gln Phe Val Asn Lys Gln Phe Asn Tyr Lys Asp Pro Val Asn Gly
  1               5                  10                  15

GTT GAC ATT GCC TAC ATC AAA ATT CCA AAC GCC GGC CAG ATG CAG CCG      96
Val Asp Ile Ala Tyr Ile Lys Ile Pro Asn Ala Gly Gln Met Gln Pro
             20                  25                  30
```

```
GTG AAG GCT TTC AAG ATT CAT AAC AAA ATC TGG GTT ATT CCG GAA CGC         144
Val Lys Ala Phe Lys Ile His Asn Lys Ile Trp Val Ile Pro Glu Arg
        35                  40                  45

GAT ACA TTT ACG AAC CCG GAA GAA GGA GAC TTG AAC CCG CCG CCG GAA         192
Asp Thr Phe Thr Asn Pro Glu Glu Gly Asp Leu Asn Pro Pro Pro Glu
 50                  55                  60

GCA AAG CAG GTG CCA GTT TCA TAC TAC GAT TCA ACC TAT CTG AGC ACA         240
Ala Lys Gln Val Pro Val Ser Tyr Tyr Asp Ser Thr Tyr Leu Ser Thr
 65                  70                  75                  80

GAC AAC GAG AAG GAT AAC TAC CTG AAG GGA GTG ACC AAA TTA TTC GAG         288
Asp Asn Glu Lys Asp Asn Tyr Leu Lys Gly Val Thr Lys Leu Phe Glu
                 85                  90                  95

CGT ATT TAT TCC ACT GAC CTG GGC CGT ATG CTG CTG ACC TCA ATC GTC         336
Arg Ile Tyr Ser Thr Asp Leu Gly Arg Met Leu Leu Thr Ser Ile Val
            100                 105                 110

CGC GGA ATC CCA TTT TGG GGT GGC AGT ACC ATT GAC ACG GAG TTG AAG         384
Arg Gly Ile Pro Phe Trp Gly Gly Ser Thr Ile Asp Thr Glu Leu Lys
            115                 120                 125

GTT ATT GAC ACT AAC TGC ATT AAC GTG ATC CAA CCA GAC GGT AGC TAC         432
Val Ile Asp Thr Asn Cys Ile Asn Val Ile Gln Pro Asp Gly Ser Tyr
130                 135                 140

AGA TCT GAA GAA CTT AAC CTC GTA ATC ATC GGG CCC TCC GCG GAC ATT         480
Arg Ser Glu Glu Leu Asn Leu Val Ile Ile Gly Pro Ser Ala Asp Ile
145                 150                 155                 160

ATC CAG TTT GAG TGC AAG AGC TTT GGC CAC GAA GTG TTG AAC CTG ACG         528
Ile Gln Phe Glu Cys Lys Ser Phe Gly His Glu Val Leu Asn Leu Thr
                165                 170                 175

CGT AAC GGT TAC GGC TCT ACT CAG TAC ATT CGT TTC AGC CCA GAC TTC         576
Arg Asn Gly Tyr Gly Ser Thr Gln Tyr Ile Arg Phe Ser Pro Asp Phe
                180                 185                 190

ACG TTC GGT TTC GAG GAG AGC CTG GAG GTT GAT ACC AAC CCG CTG TTG         624
Thr Phe Gly Phe Glu Glu Ser Leu Glu Val Asp Thr Asn Pro Leu Leu
            195                 200                 205

GGT GCA GGC AAG TTC GCA ACT GAT CCA GCG GTG ACC CTG GCA CAC GAG         672
Gly Ala Gly Lys Phe Ala Thr Asp Pro Ala Val Thr Leu Ala His Glu
210                 215                 220

CTG ATC CAC GCC GGT CAT CGT CTG TAT GGC ATT GCG ATT AAC CCG AAC         720
Leu Ile His Ala Gly His Arg Leu Tyr Gly Ile Ala Ile Asn Pro Asn
225                 230                 235                 240

CGC GTG TTC AAG GTT AAC ACC AAC GCC TAC TAC GAG ATG AGT GGT TTA         768
Arg Val Phe Lys Val Asn Thr Asn Ala Tyr Tyr Glu Met Ser Gly Leu
                245                 250                 255

GAA GTA AGC TTC GAG GAA CTG CGC ACG TTC GGT GGC CAT GAT GCG AAG         816
Glu Val Ser Phe Glu Glu Leu Arg Thr Phe Gly Gly His Asp Ala Lys
                260                 265                 270

TTT ATC GAC AGC TTG CAG GAG AAC GAG TTC CGT CTG TAC TAC TAC AAC         864
Phe Ile Asp Ser Leu Gln Glu Asn Glu Phe Arg Leu Tyr Tyr Tyr Asn
            275                 280                 285

AAG TTT AAA GAT ATT GCA AGT ACA CTG AAC AAG GCT AAG TCC ATT GTG         912
Lys Phe Lys Asp Ile Ala Ser Thr Leu Asn Lys Ala Lys Ser Ile Val
290                 295                 300

GGT ACC ACT GCT TCA TTA CAG TAT ATG AAA AAT GTT TTT AAA GAG AAA         960
Gly Thr Thr Ala Ser Leu Gln Tyr Met Lys Asn Val Phe Lys Glu Lys
305                 310                 315                 320

TAT CTC CTA TCT GAA GAT ACA TCT GGA AAA TTT TCG GTA GAT AAA TTA        1008
Tyr Leu Leu Ser Glu Asp Thr Ser Gly Lys Phe Ser Val Asp Lys Leu
                325                 330                 335

AAA TTT GAT AAG TTA TAC AAA ATG TTA ACA GAG ATT TAC ACA GAG GAT        1056
Lys Phe Asp Lys Leu Tyr Lys Met Leu Thr Glu Ile Tyr Thr Glu Asp
                340                 345                 350
```

```
AAT TTT GTT AAG TTT TTT AAA GTA CTT AAC AGA AAA ACA TAT TTG AAT      1104
Asn Phe Val Lys Phe Phe Lys Val Leu Asn Arg Lys Thr Tyr Leu Asn
            355                 360                 365

TTT GAT AAA GCC GTA TTT AAG ATA AAT ATA GTA CCT AAG GTA AAT TAC      1152
Phe Asp Lys Ala Val Phe Lys Ile Asn Ile Val Pro Lys Val Asn Tyr
        370                 375                 380

ACA ATA TAT GAT GGA TTT AAT TTA AGA AAT ACA AAT TTA GCA GCA AAC      1200
Thr Ile Tyr Asp Gly Phe Asn Leu Arg Asn Thr Asn Leu Ala Ala Asn
385                 390                 395                 400

TTT AAT GGT CAA AAT ACA GAA ATT AAT AAT ATG AAT TTT ACT AAA CTA      1248
Phe Asn Gly Gln Asn Thr Glu Ile Asn Asn Met Asn Phe Thr Lys Leu
                405                 410                 415

AAA AAT TTT ACT GGA TTG TTT GAA TTT TAT AAG TTG CTA TGT GTA AGA      1296
Lys Asn Phe Thr Gly Leu Phe Glu Phe Tyr Lys Leu Leu Cys Val Arg
            420                 425                 430

GGG ATA ATA ACT TCT AAA ACT AAA TCA TTA GAT AAA GGA TAC AAT AAG      1344
Gly Ile Ile Thr Ser Lys Thr Lys Ser Leu Asp Lys Gly Tyr Asn Lys
        435                 440                 445

GCA TTA AAT GAT TTA TGT ATC AAA GTT AAT AAT TGG GAC TTG TTT TTT      1392
Ala Leu Asn Asp Leu Cys Ile Lys Val Asn Asn Trp Asp Leu Phe Phe
450                 455                 460

AGT CCT TCA GAA GAT AAT TTT ACT AAT GAT CTA AAT AAA GGA GAA GAA      1440
Ser Pro Ser Glu Asp Asn Phe Thr Asn Asp Leu Asn Lys Gly Glu Glu
465                 470                 475                 480

ATT ACA TCT GAT ACT AAT ATA GAA GCA GCA GAA GAA AAT ATT AGT TTA      1488
Ile Thr Ser Asp Thr Asn Ile Glu Ala Ala Glu Glu Asn Ile Ser Leu
                485                 490                 495

GAT TTA ATA CAA CAA TAT TAT TTA ACC TTT AAT TTT GAT AAT GAA CCT      1536
Asp Leu Ile Gln Gln Tyr Tyr Leu Thr Phe Asn Phe Asp Asn Glu Pro
            500                 505                 510

GAA AAT ATT TCA ATA GAA AAT CTT TCA AGT GAC ATT ATA GGC CAA TTA      1584
Glu Asn Ile Ser Ile Glu Asn Leu Ser Ser Asp Ile Ile Gly Gln Leu
        515                 520                 525

GAA CTT ATG CCT AAT ATA GAA AGA TTT CCT AAT GGA AAA AAG TAT GAG      1632
Glu Leu Met Pro Asn Ile Glu Arg Phe Pro Asn Gly Lys Lys Tyr Glu
    530                 535                 540

TTA GAT AAA TAT ACT ATG TTC CAT TAT CTT CGT GCT CAA GAA TTT GAA      1680
Leu Asp Lys Tyr Thr Met Phe His Tyr Leu Arg Ala Gln Glu Phe Glu
545                 550                 555                 560

CAT GGT AAA TCT AGG ATT GCT TTA ACA AAT TCT GTT AAC GAA GCA TTA      1728
His Gly Lys Ser Arg Ile Ala Leu Thr Asn Ser Val Asn Glu Ala Leu
                565                 570                 575

TTA AAT CCT AGT CGT GTT TAT ACA TTT TTT TCT TCA GAC TAT GTA AAG      1776
Leu Asn Pro Ser Arg Val Tyr Thr Phe Phe Ser Ser Asp Tyr Val Lys
            580                 585                 590

AAA GTT AAT AAA GCT ACG GAG GCA GCT ATG TTT TTA GGC TGG GTA GAA      1824
Lys Val Asn Lys Ala Thr Glu Ala Ala Met Phe Leu Gly Trp Val Glu
        595                 600                 605

CAA TTA GTA TAT GAT TTT ACC GAT GAA ACT AGC GAA GTA AGT ACT ACG      1872
Gln Leu Val Tyr Asp Phe Thr Asp Glu Thr Ser Glu Val Ser Thr Thr
    610                 615                 620

GAT AAA ATT GCG GAT ATA ACT ATA ATT ATT CCA TAT ATA GGA CCT GCT      1920
Asp Lys Ile Ala Asp Ile Thr Ile Ile Ile Pro Tyr Ile Gly Pro Ala
625                 630                 635                 640

TTA AAT ATA GGT AAT ATG TTA TAT AAA GAT GAT TTT GTA GGT GCT TTA      1968
Leu Asn Ile Gly Asn Met Leu Tyr Lys Asp Asp Phe Val Gly Ala Leu
                645                 650                 655

ATA TTT TCA GGA GCT GTT ATT CTG TTA GAA TTT ATA CCA GAG ATT GCA      2016
Ile Phe Ser Gly Ala Val Ile Leu Leu Glu Phe Ile Pro Glu Ile Ala
```

```
                  660                 665                 670
ATA CCT GTA TTA GGT ACT TTT GCA CTT GTA TCA TAT ATT GCG AAT AAG    2064
Ile Pro Val Leu Gly Thr Phe Ala Leu Val Ser Tyr Ile Ala Asn Lys
            675                 680                 685

GTT CTA ACC GTT CAA ACA ATA GAT AAT GCT TTA AGT AAA AGA AAT GAA    2112
Val Leu Thr Val Gln Thr Ile Asp Asn Ala Leu Ser Lys Arg Asn Glu
            690                 695                 700

AAA TGG GAT GAG GTC TAT AAA TAT ATA GTA ACA AAT TGG TTA GCA AAG    2160
Lys Trp Asp Glu Val Tyr Lys Tyr Ile Val Thr Asn Trp Leu Ala Lys
705                 710                 715                 720

GTT AAT ACA CAG ATT GAT CTA ATA AGA AAA AAA ATG AAA GAA GCT TTA    2208
Val Asn Thr Gln Ile Asp Leu Ile Arg Lys Lys Met Lys Glu Ala Leu
            725                 730                 735

GAA AAT CAA GCA GAA GCA ACA AAG GCT ATA ATA AAC TAT CAG TAT AAT    2256
Glu Asn Gln Ala Glu Ala Thr Lys Ala Ile Ile Asn Tyr Gln Tyr Asn
            740                 745                 750

CAA TAT ACT GAG GAA GAG AAA AAT AAT ATT AAT TTT AAT ATT GAT GAT    2304
Gln Tyr Thr Glu Glu Glu Lys Asn Asn Ile Asn Phe Asn Ile Asp Asp
            755                 760                 765

TTA AGT TCG AAA CTT AAT GAG TCT ATA AAT AAA GCT ATG ATT AAT ATA    2352
Leu Ser Ser Lys Leu Asn Glu Ser Ile Asn Lys Ala Met Ile Asn Ile
            770                 775                 780

AAT AAA TTT TTG AAT CAA TGC TCT GTT TCA TAT TTA ATG AAT TCT ATG    2400
Asn Lys Phe Leu Asn Gln Cys Ser Val Ser Tyr Leu Met Asn Ser Met
785                 790                 795                 800

ATC CCT TAT GGT GTT AAA CGG TTA GAA GAT TTT GAT GCT AGT CTT AAA    2448
Ile Pro Tyr Gly Val Lys Arg Leu Glu Asp Phe Asp Ala Ser Leu Lys
            805                 810                 815

GAT GCA TTA TTA AAG TAT ATA TAT GAT AAT AGA GGA ACT TTA ATT GGT    2496
Asp Ala Leu Leu Lys Tyr Ile Tyr Asp Asn Arg Gly Thr Leu Ile Gly
            820                 825                 830

CAA GTA GAT AGA TTA AAA GAT AAA GTT AAT AAT ACA CTT AGT ACA GAT    2544
Gln Val Asp Arg Leu Lys Asp Lys Val Asn Asn Thr Leu Ser Thr Asp
            835                 840                 845

ATA CCT TTT CAG CTT TCC AAA TAC GTA GAT AAT CAA AGA TTA TTA TCT    2592
Ile Pro Phe Gln Leu Ser Lys Tyr Val Asp Asn Gln Arg Leu Leu Ser
            850                 855                 860

ACA TTT ACT GAA TAT ATT AAG TAA                                    2616
Thr Phe Thr Glu Tyr Ile Lys
865                 870

(2) INFORMATION FOR SEQ ID NO: 26:

(i) SEQUENCE CHARACTERISTICS:
        (A) LENGTH: 871 amino acids
        (B) TYPE: amino acid
        (D) TOPOLOGY: linear (ii) MOLECULE TYPE: protein (xi) SEQUENCE DESCRIPTION: SEQ ID NO: 26:

Met Gln Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Glu
        50                  55                  60

Ala Lys Gln Val Pro Val Ser Tyr Tyr Asp Ser Thr Tyr Leu Ser Thr
```

-continued

```
                65                  70                  75                  80
Asp Asn Glu Lys Asp Asn Tyr Leu Lys Gly Val Thr Lys Leu Phe Glu
                    85                  90                  95
Arg Ile Tyr Ser Thr Asp Leu Gly Arg Met Leu Leu Thr Ser Ile Val
                100                 105                 110
Arg Gly Ile Pro Phe Trp Gly Gly Ser Thr Ile Asp Thr Glu Leu Lys
                115                 120                 125
Val Ile Asp Thr Asn Cys Ile Asn Val Ile Gln Pro Asp Gly Ser Tyr
130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
                180                 185                 190
Thr Phe Gly Phe Glu Glu Ser Leu Glu Val Asp Thr Asn Pro Leu Leu
                195                 200                 205
Gly Ala Gly Lys Phe Ala Thr Asp Pro Ala Val Thr Leu Ala His Glu
                210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Ile Ala Ser Thr Leu Asn Lys Ala Lys Ser Ile Val
                290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Lys Phe Phe Lys Val Leu Asn Arg Lys Thr Tyr Leu Asn
                355                 360                 365
Phe Asp Lys Ala Val Phe Lys Ile Asn Ile Val Pro Lys Val Asn Tyr
                370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
                420                 425                 430
Gly Ile Ile Thr Ser Lys Thr Lys Ser Leu Asp Lys Gly Tyr Asn Lys
                435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
```

-continued

```
Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys
865                 870
```

(2) INFORMATION FOR SEQ ID NO: 27:

(i) SEQUENCE CHARACTERISTICS:
        (A) LENGTH: 2574 base pairs
        (B) TYPE: nucleic acid -continued (C) STRANDEDNESS: double
(D) TOPOLOGY: linear (ii) MOLECULE TYPE: DNA (genomic)

(xi) SEQUENCE DESCRIPTION: SEQ ID NO: 27:

| | | | | | |
|---|---|---|---|---|---|
| ATGCCGGTTA | CCATCAACAA | CTTCAACTAC | AACGACCCGA | TCGACAACAA | CAACATCATC | 60 |
| ATGATGGAAC | CGCCGTTCGC | ACGTGGTACC | GGTCGTTACT | ACAAGGCTTT | CAAGATCACC | 120 |
| GACCGTATCT | GGATCATCCC | GGAACGTTAC | ACCTTCGGTT | ACAAACCTGA | GGACTTCAAC | 180 |
| AAGAGTAGCG | GGATTTTCAA | TCGTGACGTC | TGCGAGTACT | ATGATCCAGA | TTATCTGAAT | 240 |
| ACCAACGATA | AGAAGAACAT | ATTCCTTCAG | ACTATGATCA | AGTTATTTAA | TAGAATCAAA | 300 |
| TCAAAACCAT | TGGGTGAAAA | GTTATTAGAG | ATGATTATAA | ATGGTATACC | TTATCTTGGA | 360 |
| GATAGACGTG | TTCCACTCGA | AGAGTTTAAC | ACAAACATTG | CTAGTGTAAC | TGTTAATAAA | 420 |
| TTAATCAGTA | ATCCAGGAGA | AGTGGAGCGA | AAAAAAGGTA | TTTTCGCAAA | TTTAATAATA | 480 |
| TTTGGACCTG | GGCCAGTTTT | AAATGAAAAT | GAGACTATAG | ATATAGGTAT | ACAAAATCAT | 540 |
| TTTGCATCAA | GGGAAGGCTT | CGGGGGTATA | ATGCAAATGA | AGTTTTGCCC | AGAATATGTA | 600 |
| AGCGTATTTA | ATAATGTTCA | AGAAAACAAA | GGCGCAAGTA | TATTTAATAG | ACGTGGATAT | 660 |
| TTTTCAGATC | CAGCCTTGAT | ATTAATGCAT | GAACTTATAC | ATGTTTTACA | TGGATTATAT | 720 |
| GGCATTAAAG | TAGATGATTT | ACCAATTGTA | CCAAATGAAA | AAAAATTTTT | TATGCAATCT | 780 |
| ACAGATGCTA | TACAGGCAGA | AGAACTATAT | ACATTTGGAG | GACAAGATCC | CAGCATCATA | 840 |
| ACTCCTTCTA | CGGATAAAAG | TATCTATGAT | AAAGTTTTGC | AAAATTTTAG | AGGGATAGTT | 900 |
| GATAGACTTA | ACAAGGTTTT | AGTTTGCATA | TCAGATCCTA | ACATTAATAT | TAATATATAT | 960 |
| AAAAATAAAT | TTAAAGATAA | ATATAAATTC | GTTGAAGATT | CTGAGGGAAA | ATATAGTATA | 1020 |
| GATGTAGAAA | GTTTTGATAA | ATTATATAAA | AGCTTAATGT | TTGGTTTTAC | AGAAACTAAT | 1080 |
| ATAGCAGAAA | ATTATAAAAT | AAAAACTAGA | GCTTCTTATT | TTAGTGATTC | CTTACCACCA | 1140 |
| GTAAAAATAA | AAAATTTATT | AGATAATGAA | ATCTATACTA | TAGAGGAAGG | GTTTAATATA | 1200 |
| TCTGATAAAG | ATATGGAAAA | AGAATATAGA | GGTCAGAATA | AAGCTATAAA | TAAACAAGCT | 1260 |
| TATGAAGAAA | TTAGCAAGGA | GCATTTGGCT | GTATATAAGA | TACAAATGTG | TAAAAGTGTT | 1320 |
| AAAGCTCCAG | GAATATGTAT | TGATGTTGAT | AATGAAGATT | TGTTCTTTAT | AGCTGATAAA | 1380 |
| AATAGTTTTT | CAGATGATTT | ATCTAAAAAC | GAAAGAATAG | AATATAATAC | ACAGAGTAAT | 1440 |
| TATATAGAAA | ATGACTTCCC | TATAAATGAA | TTAATTTTAG | ATACTGATTT | AATAAGTAAA | 1500 |
| ATAGAATTAC | CAAGTGAAAA | TACAGAATCA | CTTACTGATT | TTAATGTAGA | TGTTCCAGTA | 1560 |
| TATGAAAAAC | AACCCGCTAT | AAAAAAAATT | TTTACAGATG | AAAATACCAT | CTTTCAATAT | 1620 |
| TTATACTCTC | AGACATTTCC | TCTAGATATA | AGAGATATAA | GTTTAACATC | TTCATTTGAT | 1680 |
| GATGCATTAT | TATTTTCTAA | CAAAGTTTAT | TCATTTTTTT | CTATGGATTA | TATTAAAACT | 1740 |
| GCTAATAAAG | TGGTAGAAGC | AGGATTATTT | GCAGGTTGGG | TGAAACAGAT | AGTAAATGAT | 1800 |
| TTTGTAATCG | AAGCTAATAA | AAGCAATACT | ATGGATAAAA | TTGCAGATAT | ATCTCTAATT | 1860 |
| GTTCCTTATA | TAGGATTAGC | TTTAAATGTA | GGAAATGAAA | CAGCTAAAGG | AAATTTTGAA | 1920 |
| AATGCTTTTG | AGATTGCAGG | AGCCAGTATT | CTACTAGAAT | TTATACCAGA | ACTTTTAATA | 1980 |
| CCTGTAGTTG | GAGCCTTTTT | ATTAGAATCA | TATATTGACA | ATAAAAATAA | AATTATTAAA | 2040 |
| ACAATAGATA | ATGCTTTAAC | TAAAAGAAAT | GAAAATGGA | GTGATATGTA | CGGATTAATA | 2100 |
| GTAGCGCAAT | GGCTCTCAAC | AGTTAATACT | CAATTTTATA | CAATAAAAGA | GGGAATGTAT | 2160 |

-continued

```
AAGGCTTTAA ATTATCAAGC ACAAGCATTG GAAGAAATAA TAAATACAG ATATAATATA      2220

TATTCTGAAA AAGAAAAGTC AAATATTAAC ATCGATTTTA ATGATATAAA TTCTAAACTT      2280

AATGAGGGTA TTAACCAAGC TATAGATAAT ATAAATAATT TTATAAATGG ATGTTCTGTA      2340

TCATATTTAA TGAAAAAAAT GATTCCATTA GCTGTAGAAA AATTACTAGA CTTTGATAAT      2400

ACTCTCAAAA AAAATTTGTT AAATTATATA GATGAAAATA AATTATATTT GATTGGAAGT      2460

GCAGAATATG AAAAATCAAA AGTAAATAAA TACTTGAAAA CCATTATGCC GTTTGATCTT      2520

TCAATATATA CCAATGATAC AATACTAATA GAAATGTTTA ATAAATATAA TAGC           2574
```

(2) INFORMATION FOR SEQ ID NO: 28:

(i) SEQUENCE CHARACTERISTICS:
        (A) LENGTH: 2574 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:1..2574

(xi) SEQUENCE DESCRIPTION: SEQ ID NO: 28:

```
ATG CCA GTT ACA ATA AAT AAT TTT AAT TAT AAT GAT CCT ATT GAT AAT        48
Met Pro Val Thr Ile Asn Asn Phe Asn Tyr Asn Asp Pro Ile Asp Asn
 1               5                  10                  15

AAT AAT ATT ATT ATG ATG GAG CCT CCA TTT GCG AGA GGT ACG GGG AGA        96
Asn Asn Ile Ile Met Met Glu Pro Pro Phe Ala Arg Gly Thr Gly Arg
             20                  25                  30

TAT TAT AAA GCT TTT AAA ATC ACA GAT CGT ATT TGG ATA ATA CCG GAA       144
Tyr Tyr Lys Ala Phe Lys Ile Thr Asp Arg Ile Trp Ile Ile Pro Glu
         35                  40                  45

AGA TAT ACT TTT GGA TAT AAA CCT GAG GAT TTT AAT AAA AGT TCC GGT       192
Arg Tyr Thr Phe Gly Tyr Lys Pro Glu Asp Phe Asn Lys Ser Ser Gly
     50                  55                  60

ATT TTT AAT AGA GAT GTT TGT GAA TAT TAT GAT CCA GAT TAC TTA AAT       240
Ile Phe Asn Arg Asp Val Cys Glu Tyr Tyr Asp Pro Asp Tyr Leu Asn
 65                  70                  75                  80

ACT AAT GAT AAA AAG AAT ATA TTT TTA CAA ACA ATG ATC AAG TTA TTT       288
Thr Asn Asp Lys Lys Asn Ile Phe Leu Gln Thr Met Ile Lys Leu Phe
                 85                  90                  95

AAT AGA ATC AAA TCA AAA CCA TTG GGT GAA AAG TTA TTA GAG ATG ATT       336
Asn Arg Ile Lys Ser Lys Pro Leu Gly Glu Lys Leu Leu Glu Met Ile
             100                 105                 110

ATA AAT GGT ATA CCT TAT CTT GGA GAT AGA CGT GTT CCA CTC GAA GAG       384
Ile Asn Gly Ile Pro Tyr Leu Gly Asp Arg Arg Val Pro Leu Glu Glu
         115                 120                 125

TTT AAC ACA AAC ATT GCT AGT GTA ACT GTT AAT AAA TTA ATC AGT AAT       432
Phe Asn Thr Asn Ile Ala Ser Val Thr Val Asn Lys Leu Ile Ser Asn
     130                 135                 140

CCA GGA GAA GTG GAG CGA AAA AAA GGT ATT TTC GCA AAT TTA ATA ATA       480
Pro Gly Glu Val Glu Arg Lys Lys Gly Ile Phe Ala Asn Leu Ile Ile
145                 150                 155                 160

TTT GGA CCT GGG CCA GTT TTA AAT GAA AAT GAG ACT ATA GAT ATA GGT       528
Phe Gly Pro Gly Pro Val Leu Asn Glu Asn Glu Thr Ile Asp Ile Gly
                 165                 170                 175

ATA CAA AAT CAT TTT GCA TCA AGG GAA GGC TTC GGG GGT ATA ATG CAA       576
Ile Gln Asn His Phe Ala Ser Arg Glu Gly Phe Gly Gly Ile Met Gln
             180                 185                 190
```

-continued

```
ATG AAG TTT TGC CCA GAA TAT GTA AGC GTA TTT AAT AAT GTT CAA GAA      624
Met Lys Phe Cys Pro Glu Tyr Val Ser Val Phe Asn Asn Val Gln Glu
    195                 200                 205

AAC AAA GGC GCA AGT ATA TTT AAT AGA CGT GGA TAT TTT TCA GAT CCA      672
Asn Lys Gly Ala Ser Ile Phe Asn Arg Arg Gly Tyr Phe Ser Asp Pro
210                 215                 220

GCC TTG ATA TTA ATG CAT GAA CTC ATC CAC GTC CTC CAC GGT CTC TAC      720
Ala Leu Ile Leu Met His Glu Leu Ile His Val Leu His Gly Leu Tyr
225                 230                 235                 240

GGT ATC AAA GTA GAC GAC CTC CCG ATC GTC CCG AAC GAA AAA AAA TTC      768
Gly Ile Lys Val Asp Asp Leu Pro Ile Val Pro Asn Glu Lys Lys Phe
        245                 250                 255

TTC ATG CAG AGC ACC GAC GCA ATC CAG GCA GAA GAA CTC TAC ACC TTC      816
Phe Met Gln Ser Thr Asp Ala Ile Gln Ala Glu Glu Leu Tyr Thr Phe
            260                 265                 270

GGT GGT CAG GAC CCG AGC ATC ATC ACC CCG AGC ACC GAC AAA AGC ATC      864
Gly Gly Gln Asp Pro Ser Ile Ile Thr Pro Ser Thr Asp Lys Ser Ile
        275                 280                 285

TAC GAC AAA GTC CTC CAG AAC TTC CGT GGT ATC GTC GAC CGT CTC AAC      912
Tyr Asp Lys Val Leu Gln Asn Phe Arg Gly Ile Val Asp Arg Leu Asn
290                 295                 300

AAA GTC CTC GTC TGC ATC AGC GAC CCG AAC ATC AAC ATC AAC ATC TAC      960
Lys Val Leu Val Cys Ile Ser Asp Pro Asn Ile Asn Ile Asn Ile Tyr
305                 310                 315                 320

AAA AAC AAA TTC AAA GAC AAA TAC AAA TTC GTC GAA GAC AGC GAA GGT     1008
Lys Asn Lys Phe Lys Asp Lys Tyr Lys Phe Val Glu Asp Ser Glu Gly
            325                 330                 335

AAA TAC AGC ATC GAC GTC GAG AGC TTC GAC AAA CTC TAC AAA AGC CTC     1056
Lys Tyr Ser Ile Asp Val Glu Ser Phe Asp Lys Leu Tyr Lys Ser Leu
        340                 345                 350

ATG TTC GGT TTC ACC GAA ACC AAC ATC GCA GAA AAC TAC AAA ATC AAA     1104
Met Phe Gly Phe Thr Glu Thr Asn Ile Ala Glu Asn Tyr Lys Ile Lys
        355                 360                 365

ACC CGT GCA AGC TAC TTC AGC GAC AGC CTC CCG CCG GTC AAA ATC AAA     1152
Thr Arg Ala Ser Tyr Phe Ser Asp Ser Leu Pro Pro Val Lys Ile Lys
370                 375                 380

AAC CTC CTC GAC AAC GAA ATC TAC ACC ATC GAA GAA GGT TTC AAC ATC     1200
Asn Leu Leu Asp Asn Glu Ile Tyr Thr Ile Glu Glu Gly Phe Asn Ile
385                 390                 395                 400

AGC GAC AAA GAC ATG GAA AAA GAA TAC CGT GGT CAG AAC AAA GCA ATC     1248
Ser Asp Lys Asp Met Glu Lys Glu Tyr Arg Gly Gln Asn Lys Ala Ile
            405                 410                 415

AAC AAA CAA GCT TAC GAA GAA ATC AGC AAA GAA CAC CTC GCA GTC TAC     1296
Asn Lys Gln Ala Tyr Glu Glu Ile Ser Lys Glu His Leu Ala Val Tyr
        420                 425                 430

AAA ATC CAG ATG TGC AAA AGC GTC AAA GCA CCG GGT ATC TGC ATC GAC     1344
Lys Ile Gln Met Cys Lys Ser Val Lys Ala Pro Gly Ile Cys Ile Asp
        435                 440                 445

GTT GAC AAC GAA GAC CTC TTC TTC ATC GCA GAC AAA AAC AGC TTC AGC     1392
Val Asp Asn Glu Asp Leu Phe Phe Ile Ala Asp Lys Asn Ser Phe Ser
450                 455                 460

GAC GAC CTC AGC AAA AAC GAA CGT ATC GAA TAC AAC ACC CAG AGC AAC     1440
Asp Asp Leu Ser Lys Asn Glu Arg Ile Glu Tyr Asn Thr Gln Ser Asn
465                 470                 475                 480

TAC ATC GAA AAC GAC TTC CCG ATC AAC GAA CTC ATC CTC GAC ACC GAC     1488
Tyr Ile Glu Asn Asp Phe Pro Ile Asn Glu Leu Ile Leu Asp Thr Asp
            485                 490                 495

CTC ATC AGC AAA ATC GAA CTC CCG AGC GAA AAC ACC GAA AGC CTC ACC     1536
Leu Ile Ser Lys Ile Glu Leu Pro Ser Glu Asn Thr Glu Ser Leu Thr
        500                 505                 510
```

```
GAC TTC AAC GTT GAC GTC CCG GTC TAC GAA AAA CAG CCG GCA ATC AAA      1584
Asp Phe Asn Val Asp Val Pro Val Tyr Glu Lys Gln Pro Ala Ile Lys
        515                 520                 525

AAA ATC TTC ACC GAC GAA AAC ACC ATC TTC CAG TAC CTC TAC AGC CAG      1632
Lys Ile Phe Thr Asp Glu Asn Thr Ile Phe Gln Tyr Leu Tyr Ser Gln
        530                 535                 540

ACC TTC CCG CTA GAT ATA AGA GAT ATA AGT TTA ACA TCT TCA TTT GAT      1680
Thr Phe Pro Leu Asp Ile Arg Asp Ile Ser Leu Thr Ser Ser Phe Asp
545                 550                 555                 560

GAT GCA TTA TTA TTT TCT AAC AAA GTT TAT TCA TTT TTT TCT ATG GAT      1728
Asp Ala Leu Leu Phe Ser Asn Lys Val Tyr Ser Phe Phe Ser Met Asp
                565                 570                 575

TAT ATT AAA ACT GCT AAT AAA GTG GTA GAA GCA GGA TTA TTT GCA GGT      1776
Tyr Ile Lys Thr Ala Asn Lys Val Val Glu Ala Gly Leu Phe Ala Gly
        580                 585                 590

TGG GTG AAA CAG ATA GTA AAT GAT TTT GTA ATC GAA GCT AAT AAA AGC      1824
Trp Val Lys Gln Ile Val Asn Asp Phe Val Ile Glu Ala Asn Lys Ser
        595                 600                 605

AAT ACT ATG GAT AAA ATT GCA GAT ATA TCT CTA ATT GTT CCT TAT ATA      1872
Asn Thr Met Asp Lys Ile Ala Asp Ile Ser Leu Ile Val Pro Tyr Ile
        610                 615                 620

GGA TTA GCT TTA AAT GTA GGA AAT GAA ACA GCT AAA GGA AAT TTT GAA      1920
Gly Leu Ala Leu Asn Val Gly Asn Glu Thr Ala Lys Gly Asn Phe Glu
625                 630                 635                 640

AAT GCT TTT GAG ATT GCA GGA GCC AGT ATT CTA CTA GAA TTT ATA CCA      1968
Asn Ala Phe Glu Ile Ala Gly Ala Ser Ile Leu Leu Glu Phe Ile Pro
                645                 650                 655

GAA CTT TTA ATA CCT GTA GTT GGA GCC TTT TTA TTA GAA TCA TAT ATT      2016
Glu Leu Leu Ile Pro Val Val Gly Ala Phe Leu Leu Glu Ser Tyr Ile
                660                 665                 670

GAC AAT AAA AAT AAA ATT ATT AAA ACA ATA GAT AAT GCT TTA ACT AAA      2064
Asp Asn Lys Asn Lys Ile Ile Lys Thr Ile Asp Asn Ala Leu Thr Lys
        675                 680                 685

AGA AAT GAA AAA TGG AGT GAT ATG TAC GGA TTA ATA GTA GCG CAA TGG      2112
Arg Asn Glu Lys Trp Ser Asp Met Tyr Gly Leu Ile Val Ala Gln Trp
        690                 695                 700

CTC TCA ACA GTT AAT ACT CAA TTT TAT ACA ATA AAA GAG GGA ATG TAT      2160
Leu Ser Thr Val Asn Thr Gln Phe Tyr Thr Ile Lys Glu Gly Met Tyr
705                 710                 715                 720

AAG GCT TTA AAT TAT CAA GCA CAA GCA TTG GAA GAA ATA ATA AAA TAC      2208
Lys Ala Leu Asn Tyr Gln Ala Gln Ala Leu Glu Glu Ile Ile Lys Tyr
                725                 730                 735

AGA TAT AAT ATA TAT TCT GAA AAA GAA AAG TCA AAT ATT AAC ATC GAT      2256
Arg Tyr Asn Ile Tyr Ser Glu Lys Glu Lys Ser Asn Ile Asn Ile Asp
                740                 745                 750

TTT AAT GAT ATA AAT TCT AAA CTT AAT GAG GGT ATT AAC CAA GCT ATA      2304
Phe Asn Asp Ile Asn Ser Lys Leu Asn Glu Gly Ile Asn Gln Ala Ile
        755                 760                 765

GAT AAT ATA AAT AAT TTT ATA AAT GGA TGT TCT GTA TCA TAT TTA ATG      2352
Asp Asn Ile Asn Asn Phe Ile Asn Gly Cys Ser Val Ser Tyr Leu Met
        770                 775                 780

AAA AAA ATG ATT CCA TTA GCT GTA GAA AAA TTA CTA GAC TTT GAT AAT      2400
Lys Lys Met Ile Pro Leu Ala Val Glu Lys Leu Leu Asp Phe Asp Asn
785                 790                 795                 800

ACT CTC AAA AAA AAT TTG TTA AAT TAT ATA GAT GAA AAT AAA TTA TAT      2448
Thr Leu Lys Lys Asn Leu Leu Asn Tyr Ile Asp Glu Asn Lys Leu Tyr
                805                 810                 815

TTG ATT GGA AGT GCA GAA TAT GAA AAA TCA AAA GTA AAT AAA TAC TTG      2496
Leu Ile Gly Ser Ala Glu Tyr Glu Lys Ser Lys Val Asn Lys Tyr Leu
```

```
                    820              825              830
AAA ACC ATT ATG CCG TTT GAT CTT TCA ATA TAT ACC AAT GAT ACA ATA      2544
Lys Thr Ile Met Pro Phe Asp Leu Ser Ile Tyr Thr Asn Asp Thr Ile
            835              840              845

CTA ATA GAA ATG TTT AAT AAA TAT AAT AGC                              2574
Leu Ile Glu Met Phe Asn Lys Tyr Asn Ser
850             855
```

(2) INFORMATION FOR SEQ ID NO: 29:

(i) SEQUENCE CHARACTERISTICS:
        (A) LENGTH: 858 amino acids
        (B) TYPE: amino acid
        (D) TOPOLOGY: linear (ii) MOLECULE TYPE: protein (xi) SEQUENCE DESCRIPTION: SEQ ID NO: 29:

```
Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300
```

```
Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
370                 375                 380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
        595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
```

-continued

```
                       725                 730                 735
Arg Tyr Asn Ile Tyr Ser Glu Lys Glu Lys Ser Asn Ile Asn Ile Asp
                740             745             750

Phe Asn Asp Ile Asn Ser Lys Leu Asn Glu Gly Ile Asn Gln Ala Ile
            755             760             765

Asp Asn Ile Asn Asn Phe Ile Asn Gly Cys Ser Val Ser Tyr Leu Met
    770                 775             780

Lys Lys Met Ile Pro Leu Ala Val Glu Lys Leu Leu Asp Phe Asp Asn
785             790             795                 800

Thr Leu Lys Lys Asn Leu Leu Asn Tyr Ile Asp Glu Asn Lys Leu Tyr
            805             810             815

Leu Ile Gly Ser Ala Glu Tyr Glu Lys Ser Lys Val Asn Lys Tyr Leu
            820             825             830

Lys Thr Ile Met Pro Phe Asp Leu Ser Ile Tyr Thr Asn Asp Thr Ile
        835             840             845

Leu Ile Glu Met Phe Asn Lys Tyr Asn Ser
850                 855
```

RECOMBINANT TOXIN FRAGMENTS

CROSS REFERENCE TO RELATED APPLICATIONS

The present application is a continuation of PCT/GB97/02273, filed Aug. 22, 1997, which is a continuation-in-part of U.S. application Ser. No. 08/782,893, filed Dec. 27, 1996 now abandoned.

FIELD OF THE INVENTION

This invention relates to recombinant toxin fragments, to DNA encoding these fragments and to their uses such as in a vaccine and for in vitro and in vivo purposes.

BACKGROUND OF THE INVENTION

The clostridial neurotoxins are potent inhibitors of calcium-dependent neurotransmitter secretion in neuronal cells. They are currently considered to mediate this activity through a specific endoproteolytic cleavage of at least one of three vesicle or pre-synaptic membrane associated proteins VAMP, syntaxin or SNAP-25 which are central to the vesicle docking and membrane fusion events of neurotransmitter secretion. The neuronal cell targeting of tetanus and botulinum neurotoxins is considered to be a receptor mediated event following which the toxins become internalised and subsequently traffic to the appropriate intracellular compartment where they effect their endopeptidase activity.

The clostridial neurotoxins share a common architecture of a catalytic L-chain (LC, ca 50 kDa) disulphide linked to a receptor binding and translocating H-chain (HC, ca 100 kDa). The HC polypeptide is considered to comprise all or part of two distinct functional domains. The carboxy-terminal half of the HC (ca 50 kDa), termed the $H_C$ domain, is involved in the high affinity, neurospecific binding of the neurotoxin to cell surface receptors on the target neuron, whilst the amino-terminal half, termed the $H_N$ domain (ca 50 kDa), is considered to mediate the translocation of at least some portion of the neurotoxin across cellular membranes such that the functional activity of the LC is expressed within the target cell. The $H_N$ domain also has the property, under conditions of iow pH, of forming ion-permeable channels in lipid membranes, this may in some manner relate to its translocation function.

For botulinum neurotoxin type A (BoNT/A) these domains are considered to reside within amino acid residues 872–1296 for the $H_C$, amino acid residues 449–871 for the $H_N$ and residues 1–448 for the LC. Digestion with trypsin effectively degrades the $H_C$ domain of the BoNT/A to generate a non-toxic fragment designated $LH_N$, which is no longer able to bind to and enter neurons (FIG. 1). The $LH_N$ fragment so produced also has the property of enhanced solubility compared to both the parent holotoxin and the isolated LC.

It is therefore possible to provide functional definitions of the domains within the neurotoxin molecule, as follows:

(A) Clostridial Neurotoxin Light Chain:
- a metalloprotease exhibiting high substrate specificity for vesicle and/or plasma-membrane associated proteins involved in the exocytotic process. In particular, it cleaves one or more of SNAP-25, VAMP (synaptobrevin/cellubrevin) and syntaxin.

(B) Clostridial Neurotoxin Heavy Chain $H_N$ Domain:
- a portion of the heavy chain which enables translocation of that portion of the neurotoxin molecule such that a functional expression of light chain activity occurs within a target cell.
- the domain responsible for translocation of the endopeptidase activity, following binding of neurotoxin to its specific cell surface receptor via the binding domain, into the target cell.
- the domain responsible for formation of ion-permeable pores in lipid membranes under conditions of low pH.
- the domain responsible for increasing the solubility of the entire polypeptide compared to the solubility of light chain alone.

(C) Clostridial Neurotoxin Heavy Chain $H_C$ Domain.
- a portion of the heavy chain which is responsible for binding of the native holotoxin to cell surface receptor (s) involved in the intoxicating action of clostridial toxin prior to internalisation of the toxin into the cell.

The identity of the cellular recognition markers for these toxins is currently not understood and no specific receptor species have yet been identified although Kozaki et al. have reported that synaptotagmin may be the receptor for botulinum neurotoxin type B. It is probable that each of the neurotoxins has a different receptor.

It is desirable to have positive controls for toxin assays, to develop clostridial toxin vaccines and to develop therapeutic agents incorporating desirable properties of clostridial toxin.

However, due to its extreme toxicity, the handling of native toxin is hazardous.

The present invention seeks to overcome or at least ameliorate problems associated with production and handling of clostridial toxin.

SUMMARY OF THE INVENTION

Accordingly, the invention provides a polypeptide comprising first and second domains, wherein said first domain is adapted to cleave one or more vesicle or plasma-membrane associated proteins essential to neuronal exocytosis and wherein said second domain is adapted (i) to translocate the polypeptide into the cell or (ii) to increase the solubility of the polypeptide compared to the solubility of the first domain on its own or (iii) both to translocate the polypeptide into the cell and to increase the solubility of the polypeptide compared to the solubility of the first domain on its own, said polypeptide being free of clostridial neurotoxin and free of any clostridial neurotoxin precursor that can be converted into toxin by proteolytic action. Accordingly, the invention may thus provide a single polypeptide chain containing a domain equivalent to a clostridial toxin light chain and a domain providing the functional aspects of the $H_N$ of a clostridial toxin heavy chain, whilst lacking the functional aspects of a clostridial toxin $H_C$ domain.

DETAILED DESCRIPTION OF THE PREFERRED EMBODIMENTS

For the purposes of the invention, the functional property or properties of the $H_N$ of a clostridial toxin heavy chain that are required to be exhibited by the second domain of the polypeptide of the invention are either (i) translocation of the polypeptide into a cell, or (ii) increasing solubility of the polypeptide compared to solubility of the first domain on its own or (iii) both (i) and (ii). References hereafter to a $H_N$ domain or to the functions of a $H_N$ domain are references to this property or properties. The second domain is not required to exhibit other properties of the $H_N$ domain of a clostridial toxin heavy chain.

A polypeptide of the invention can thus be soluble but lack the translocation function of a native toxin-this is of use in providing an immunogen for vaccinating or assisting to vaccinate an individual against challenge by toxin. In a specific embodiment of the invention described in an example below a polypeptide designated $LH_{423}/A$ elicited neutralising antibodies against type A neurotoxin. A polypeptide of the invention can likewise thus be relatively insoluble but retain the translocation function of a native toxin—this is of use if solubility is imparted to a composition made up of that polypeptide and one or more other components by one or more of said other components.

The first domain of the polypeptide of the invention cleaves one or more vesicle or plasma-membrane associated proteins essential to the specific cellular process of exocytosis, and cleavage of these proteins results in inhibition of exocytosis, typically in a non-cytotoxic manner. The cell or cells affected are not restricted to a particular type or subgroup but can include both neuronal and non-neuronal cells. The activity of clostridial neurotoxins in inhibiting exocytosis has, indeed, been observed almost universally in eukaryotic cells expressing a relevant cell surface receptor, including such diverse cells as from Aplysia (sea slug), Drosophila (fruit fly) and mammalian nerve cells, and the activity of the first domain is to be understood as including a corresponding range of cells.

The polypeptide of the invention may be obtained by expression of a recombinant nucleic acid, preferably a DNA, and is a single polypeptide, that is to say not cleaved into separate light and heavy chain domains. The polypeptide is thus available in convenient and large quantities using recombinant techniques.

In a polypeptide according to the invention, said first domain preferably comprises a clostridial toxin light chain or a fragment or variant of a clostridial toxin light chain. The fragment is optionally an N-terminal, or C-terminal fragment of the light chain, or is an internal fragment, so long as it substantially retains the ability to cleave the vesicle or plasma-membrane associated protein essential to exocytosis. The minimal domains necessary for the activity of the light chain of clostridial toxins are described in J. Biol. Chem., Vol.267, No. 21, July 1992, pages 14721–14729. The variant has a different peptide sequence from the light chain or from the fragment, though it too is capable of cleaving the vesicle or plasma-membrane associated protein. It is conveniently obtained by insertion, deletion and/or substitution of a light chain or fragment thereof. In embodiments of the invention described below a variant sequence comprises (i) an N-terminal extension to a clostridial toxin light chain or fragment (ii) a clostridial toxin light chain or fragment modified by alteration of at least one amino acid (iii) a C-terminal extension to a clostridial toxin light chain or fragment, or (iv) combinations of 2 or more of (i)–(iii).

In further embodiments of the invention, the variant contains an amino acid sequence modified so that (a) there is no protease sensitive region between the LC and $H_N$ components of the polypeptide, or (b) the protease sensitive region is specific for a particular protease. This latter embodiment is of use if it is desired to activate the endopeptidase activity of the light chain in a particular environment or cell. Though, in general, the polypeptides of the invention are activated prior to administration.

The first domain preferably exhibits endopeptidase activity specific for a substrate selected from one or more of SNAP-25, synaptobrevin/VAMP and syntaxin. The clostridial toxin is preferably botulinum toxin or tetanus toxin.

In an embodiment of the invention described in an example below, the toxin light chain and the portion of the toxin heavy chain are of botulinum toxin type A. In a further embodiment of the invention described in an example below, the toxin light chain and the portion of the toxin heavy chain are of botulinum toxin type B. The polypeptide optionally comprises a light chain or fragment or variant of one toxin type and a heavy chain or fragment or variant of another toxin type.

In a polypeptide according to the invention said second domain preferably comprises a clostridial toxin heavy chain $H_N$ portion or a fragment or variant of a clostridial toxin heavy chain $H_N$ portion. The fragment is optionally an N-terminal or C-terminal or internal fragment, so long as it retains the function of the $H_N$ domain. Teachings of regions within the $H_N$ responsible for its function are provided for example in Biochemistry 1995, 34, pages 15175–15181 and Eur. J. Biochem, 1989, 185, pages 197–203. The variant has a different sequence from the $H_N$ domain or fragment, though it too retains the function of the $H_N$ domain. It is conveniently obtained by insertion, deletion and/or substitution of a $H_N$ domain or fragment thereof. In embodiments of the invention, described below, it comprises (i) an N-terminal extension to a $H_N$ domain or fragment, (ii) a C-terminal extension to a $H_N$ domain or fragment, (iii) a modification to a $H_N$ domain or fragment by alteration of at least one amino acid, or (iv) combinations of 2 or more of (i)–(iii). The clostridial toxin is preferably botulinum toxin or tetanus toxin.

The invention also provides a polypeptide comprising a clostridial neurotoxin light chain and a N-terminal fragment of a clostridial neurotoxin heavy chain, the fragment preferably comprising at least 423 of the N-terminal amino acids of the heavy chain of botulinum toxin type A, 417 of the N-terminal amino acids of the heavy chain of botulinum toxin type B or the equivalent number of N-terminal amino acids of the heavy chain of other types of clostridial toxin such that the fragment possesses an equivalent alignment of homologous amino acid residues.

These polypeptides of the invention are thus not composed of two or more polypeptides, linked for example by di-sulphide bridges into composite molecules. Instead, these polypeptides are single chains and are not active or their activity is significantly reduced in an in vitro assay of neurotoxin endopeptidase activity.

Further, the polypeptides may be susceptible to be converted into a form exhibiting endopeptidase activity by the action of a proteolytic agent, such as trypsin. In this way it is possible to control the endopeptidase activity of the toxin light chain.

In a specific embodiment of the invention described in an example below, there is provided a polypeptide lacking a portion designated $H_C$ of a clostridial toxin heavy chain. This portion, seen in the naturally produced toxin, is responsible for binding of toxin to cell surface receptors prior to internalisation of the toxin. This specific embodiment is therefore adapted so that it can not be converted into active toxin, for example by the action of a proteolytic enzyme. The invention thus also provides a polypeptide comprising a clostridial toxin light chain and a fragment of a clostridial toxin heavy chain, said fragment being not capable of binding to those cell surface receptors involved in the intoxicating action of clostridial toxin, and it is preferred that such a polypeptide lacks an intact portion designated $H_C$ of a clostridial toxin heavy chain.

In further embodiments of the invention there are provided compositions containing a potypeptide comprising a clostridial toxin light chain and a portion designated $H_N$ of a clostridial toxin heavy chain, and wherein the composition is free of clostridial toxin and free of any clostridial toxin precursor that may be converted into clostridial toxin by the action of a proteolytic enzyme. Examples of these compositions include those containing toxin light chain and $H_N$ sequences of botulinum toxin types A, B, $C_1$, D, E, F and G.

The polypeptides of the invention are conveniently adapted to bind to, or include, a ligand for targeting to desired cells. The polypeptide optionally comprises a sequence that binds to, for example, an immunoglobulin. A suitable sequence is a tandem repeat synthetic IgG binding domain derived from domain B of Staphylococcal protein A. Choice of immunoglobulin specificity then determines the target for a polypeptide-immunoglobulin complex. Alternatively, the polypeptide comprises a non-clostridial sequence that binds to a cell surface receptor, suitable sequences including insulin-like growth factor-1 (IGF-1) which binds to its specific receptor on particular cell types and the 14 amino acid residue sequence from the carboxy-terminus of cholera toxin A subunit which is able to bind the cholera toxin B subunit and thence to GM1 gangliosides. A polypeptide according to the invention thus, optionally, further comprises a third domain adapted for binding of the polypeptide to a cell.

In a second aspect the invention provides a fusion protein comprising a fusion of (a) a polypeptide of the invention as described above with (b) a second polypeptide adapted for binding to a chromatography matrix so as to enable purification of the fusion protein using said chromatography matrix. It is convenient for the second polypeptide to be adapted to bind to an affinity matrix, such as a glutathione Sepharose, enabling rapid separation and purification of the fusion protein from an impure source, such as a cell extract or supernatant.

One possible second purification polypeptide is glutathione-S-transferase (GST), and others will be apparent to a person of skill in the art, being chosen so as to enable purification on a chromatography column according to conventional techniques.

As noted above, by proteolytic treatment, for example using trypsin, of a polypeptide of the invention it is possible to induce endopeptidase activity in the treated polypeptide. A third aspect of the invention provides a composition comprising a derivative of a clostridial toxin, said derivative retaining at least 10% of the endopeptidase activity of the clostridial toxin, said derivative further being non-toxic in vivo due to its inability to bind to cell surface receptors, and wherein the composition is free of any component, such as toxin or a further toxin derivative, that is toxic in vivo. The activity of the derivative preferably approaches that of natural toxin, and is thus preferably at least 30% and most preferably at least 60% of natural toxin. The overall endopeptidase activity of the composition will, of course, also be determined by the amount of the derivative that is present.

While it is known to treat naturally produced clostridial toxin to remove the Hc domain, this treatment does not totally remove toxicity of the preparation, instead some residual toxin activity remains. Natural toxin treated in this way is therefore still not entirely safe. The composition of the invention, derived by treatment of a pure source of polypeptide advantageously is free of toxicity, and can conveniently be used as a positive control in a toxin assay, as a vaccine against clostridial toxin or for other purposes where it is essential that there is no residual toxicity in the composition.

The invention enables production of the polypeptides and fusion proteins of the invention by recombinant means.

A fourth aspect of the invention provides a nucleic acid encoding a polypeptide or a fusion protein according to any of the aspects of the invention described above.

In one embodiment of this aspect of the invention, a DNA sequence provided to code for the polypeptide or fusion protein is not derived from native clostridial sequences, but is an artificially derived sequence not preexisting in nature.

A specific DNA (SEQ ID NO: 1) described in more detail below encodes a polypeptide or a fusion protein comprising nucleotides encoding residues 1–871 of a botulinum toxin type A. Said polypeptide comprises the light chain domain and the first 423 amino acid residues of the amino terminal portion of a botulinum toxin type A heavy chain. This recombinant product is designated $LH_{423}/A$ (SEQ ID NO: 2).

In a second embodiment of this aspect of the invention a DNA sequence which codes for the polypeptide or fusion protein is derived from native clostridial sequences but codes for a polypeptide or fusion protein not found in nature.

A specific DNA (SEQ ID NO: 19) described in more detail below encodes a polypeptide or a fusion protein and comprises nucleotides encoding residues 1–1171 of a botulinum toxin type B. Said polypeptide comprises the light chain domain and the first 728 amino acid residues of the amino terminal protein of a botulinum type B heavy chain. This recombinant product is designated LH728/B (SEQ ID NO: 20).

The invention thus also provides a method of manufacture of a polypeptide comprising expressing in a host cell a DNA according to the third aspect of the invention. The host cell is suitably not able to cleave a polypeptide or fusion protein of the invention so as to separate light and heavy toxin chains; for example, a non-clostridial host.

The invention further provides a method of manufacture of a polypeptide comprising expressing in a host cell a DNA encoding a fusion protein as described above, purifying the fusion protein by elution through a chromatography column adapted to retain the fusion protein, eluting through said chromatography column a ligand adapted to displace the fusion protein and recovering the fusion protein. Production of substantially pure fusion protein is thus made possible. Likewise, the fusion protein is readily cleaved to yield a polypeptide of the invention, again in substantially pure form, as the second polypeptide may conveniently be removed using the same type of chromatography column.

The $LH_N/A$ derived from dichain native toxin requires extended digestion with trypsin to remove the C-terminal ½ of the heavy chain, the $H_C$ domain. The loss of this domain effectively renders the toxin inactive in vivo by preventing its interaction with host target cells. There is, however, a residual toxic activity which may indicate a contaminating, trypsin insensitive, form of the whole type A neurotoxin.

In contrast, the recombinant preparations of the invention are the product of a discreet, defined gene coding sequence and can not be contaminated by full length toxin protein. Furthermore, the product as recovered from *E. coli*, and from other recombinant expression hosts, is an inactive single chain peptide or if expression hosts produce a processed, active polypeptide it is not a toxin. Endopeptidase activity of $LH_{423}/A$, as assessed by the current in vitro peptide cleavage assay, is wholly dependent on activation of the recombinant molecule between residues 430 and 454 by trypsin. Other proteolytic enzymes that cleave between these two residues are generally also suitable for activation of the recombinant molecule. Trypsin cleaves the peptide bond C-terminal to Arginine or C-terminal to Lysine and is suitable as these residues are found in the 430–454 region and are exposed (see FIG. 12).

The recombinant polypeptides of the invention are potential therapeutic agents for targeting to cells expressing the relevant substrate but which are not implicated in effecting botulism. An example might be where secretion of neurotransmitter is inappropriate or undesirable or alternatively where a neuronal cell is hyperactive in terms of regulated secretion of substances other than neurotransmitter. In such an example the function of the Hc domain of the native toxin could be replaced by an alternative targeting sequence providing, for example, a cell receptor ligand and/or translocation domain.

One application of the recombinant polypeptides of the invention will be as a reagent component for synthesis of therapeutic molecules, such as disclosed in WO-A-94/21300. The recombinant product will also find application as a non-toxic standard for the assessment and development of in vitro assays for detection of functional botulinum or tetanus neurotoxins either in foodstuffs or in environmental samples, for example as disclosed in EP-A-0763131.

A further option is addition, to the C-terminal end of a polypeptide of the invention, of a peptide sequence which allows specific chemical conjugation to targeting ligands of both protein and non-protein origin.

In yet a further embodiment an alternative targeting ligand is added to the N-terminus of polypeptides of the invention. Recombinant $LH_N$ derivatives have been designated that have specific protease cleavage sites engineered at the C-terminus of the LC at the putative trypsin sensitive region and also at the extreme C-terminus of the complete protein product. These sites will enhance the activational specificity of the recombinant product such that the dichain species can only be activated by proteolytic cleavage of a more predictable nature than use of trypsin.

The $LH_N$ enzymatically produced from native BoNT/A is an efficient immunogen and thus the recombinant form with its total divorce from any full length neurotoxin represents a vaccine component. The recombinant product may serve as a basal reagent for creating defined protein modifications in support of any of the above areas.

Recombinant constructs are assigned distinguishing names on the basis of their amino acid sequence length and their Light Chain (L-chain, L) and Heavy Chain (H-chain, H) content as these relate to translated DNA sequences in the public domain or specifically to SEQ ID NO: 2 and SEQ ID NO: 20. The 'LH' designation is followed by '/X' where 'X' denotes the corresponding clostridial toxin serotype or class, e.g. 'A' for botulinum neurotoxin type A or 'TeTx' for tetanus toxin. Sequence variants from that of the native toxin polypeptide are given in parenthesis in standard format, namely the residue position number prefixed by the residue of the native sequence and suffixed by the residue of the variant.

Subscript number prefixes indicate an amino-terminal (N-terminal) extension, or where negative a deletion, to the translated sequence. Similarly, subscript number suffixes indicate a carboxy terminal (C-terminal) extension or where negative numbers are used, a deletion. Specific sequence inserts such as protease cleavage sites are indicated using abbreviations, e.g. Factor Xa is abbreviated to FXa. L-chain C-terminal suffixes and H-chain N-terminal prefixes are separated by a '/' to indicate the predicted junction between the L and H-chains. Abbreviations for engineered ligand sequences are prefixed or suffixed to the clostridial L-chain or H-chain corresponding to their position in the translation product.

Following this nomenclature, $LH_{423}/A$=SEQ ID NO: 2, containing the entire L-chain and 423 amino acids of the H-chain of botulinum neurotoxin type A;

$_2LH_{423}/A$=a variant of this molecule, containing a two amino acid extension to the N-terminus of the L-chain;

$_2L_{/2}H_{423}/A$=a further variant in which the molecule contains a two amino acid extension on the N-terminus of both the L-chain and the H-chain;

$_2L_{FXa/2}H_{423}/A$=a further variant containing a two amino acid extension to the N-terminus of the L-chain, and a Factor Xa cleavage sequence at the C-terminus of the L-chain which, after cleavage of the molecule with Factor Xa leaves a two amino acid N-terminal extension to the H-chain component; and $_2L_{FXa/2}H_{423}/A$-IGF-1=a variant of this molecule which has a further C-terminal extension to the H-chain, in this example the insulin-like growth factor 1 (IGF-1) sequence.

There now follows description of specific embodiments of the invention, illustrated by drawings in which:

FIG. 3 is a graph comparing activity of native toxin, trypsin generated "native" LHN/A and an embodiment of the invention designated $_2LH_{423}/A$ $(Q_2E,N_26K,A_{27}Y)$ in an in vitro peptide cleavage assay;

FIG. 4 is a comparison of the first 33 amino acids in published sequences of native toxin and embodiments of the invention;

FIG. 5 shows the transition region of an embodiment of the invention designated $L/_4H_{423}/A$ illustrating insertion of four amino acids at the N-terminus of the $H_N$ sequence; amino acids coded for by the Eco 47 III restriction endonuclease cleavage site are marked and the $H_N$ sequence then begins ALN . . . ;

FIG. 6 shows the transition region of an embodiment of the invention designated $L_{FXa/3}H_{423}/A$ illustrating insertion of a Factor Xa cleavage site at the C-terminus of the L-chain, and three additional amino acids coded for at the N-terminus of the H-sequence; the N-terminal amino acid of the cleavage-activated $H_N$ will be cysteine;

FIG. 7 shows the C-terminal portion of the amino acid sequence of an embodiment of the invention designated $L_{FXa/3}H_{423}/A$-IGF-1, a fusion protein; the IGF-1 sequence begins at position G882;

FIG. 8 shows the C-terminal portion of the amino acid sequence of an embodiment of the invention designated $L_{FXa/3}H_{423}/A$-CtxA14, a fusion protein; the C-terminal CtxA sequence begins at position $Q_{882}$;

FIG. 9 shows the C-terminal portion of the amino acid sequence of an embodiment of the invention designated $L_{FXa/3}H_{423}/A$-ZZ, a fusion protein; the C-terminal ZZ sequence begins at position $A_{890}$ immediately after a genenase recognition site (underlined);

show schematic representations of manipulations of

Figure 10:
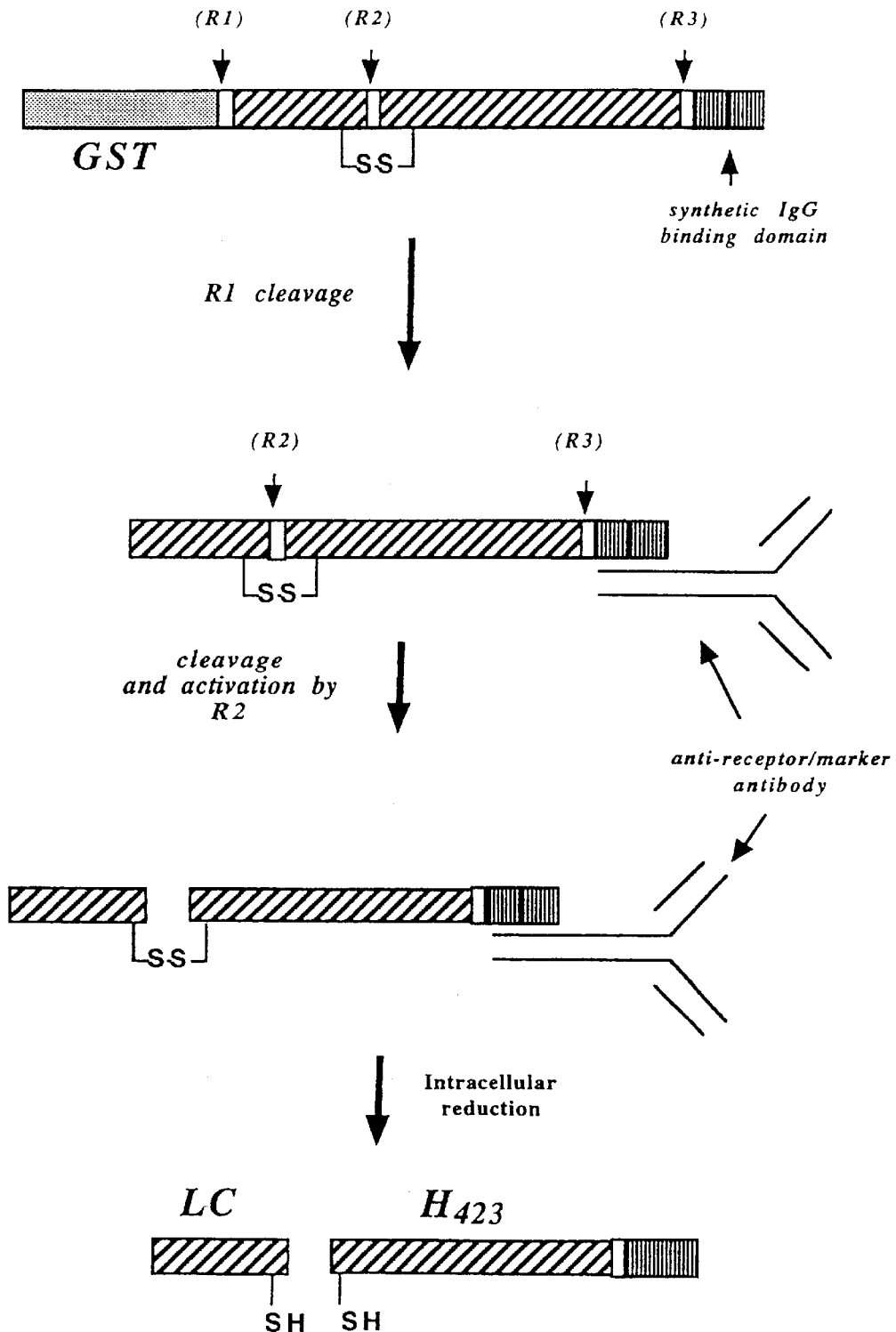
Figure 11:
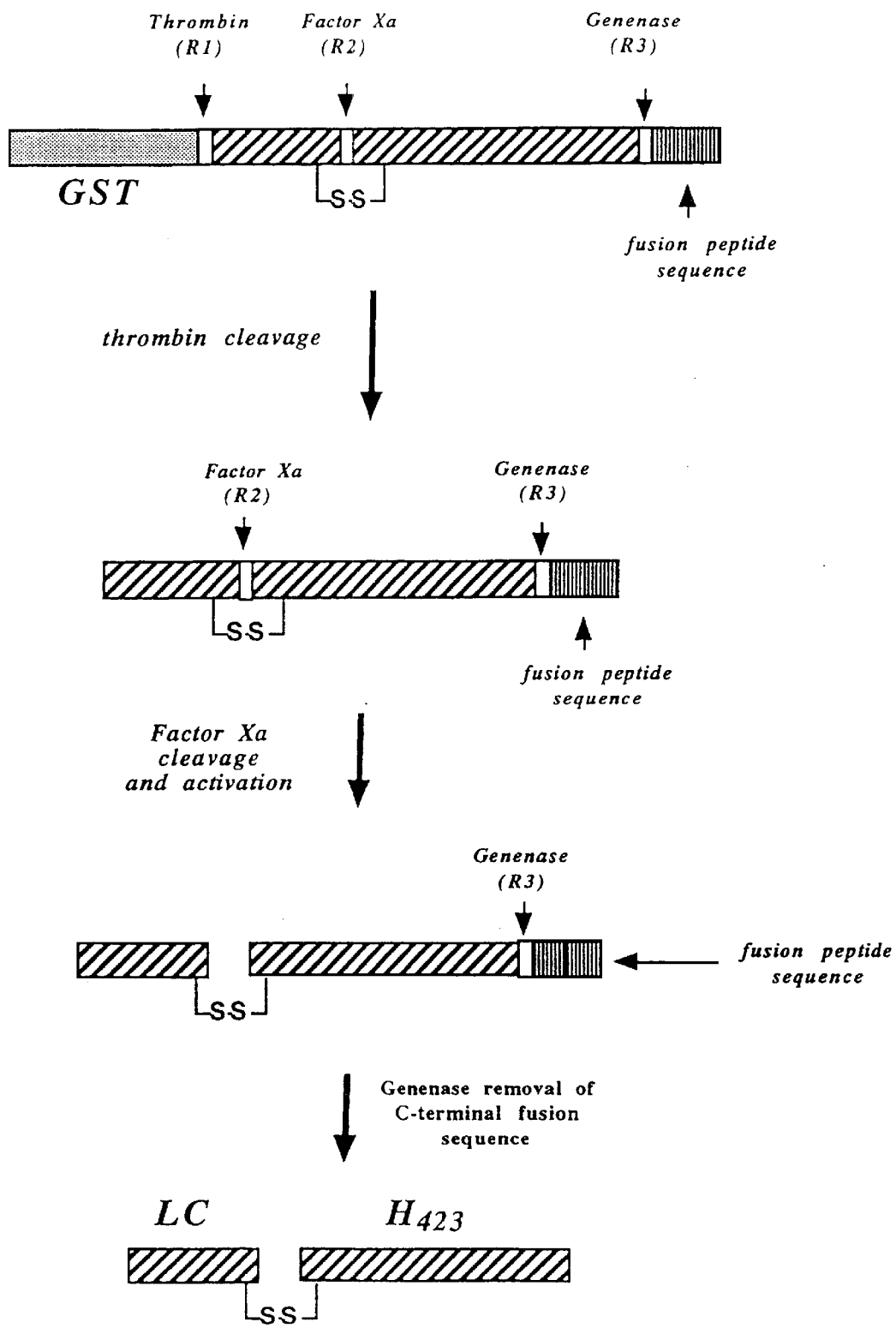
Figure 12:
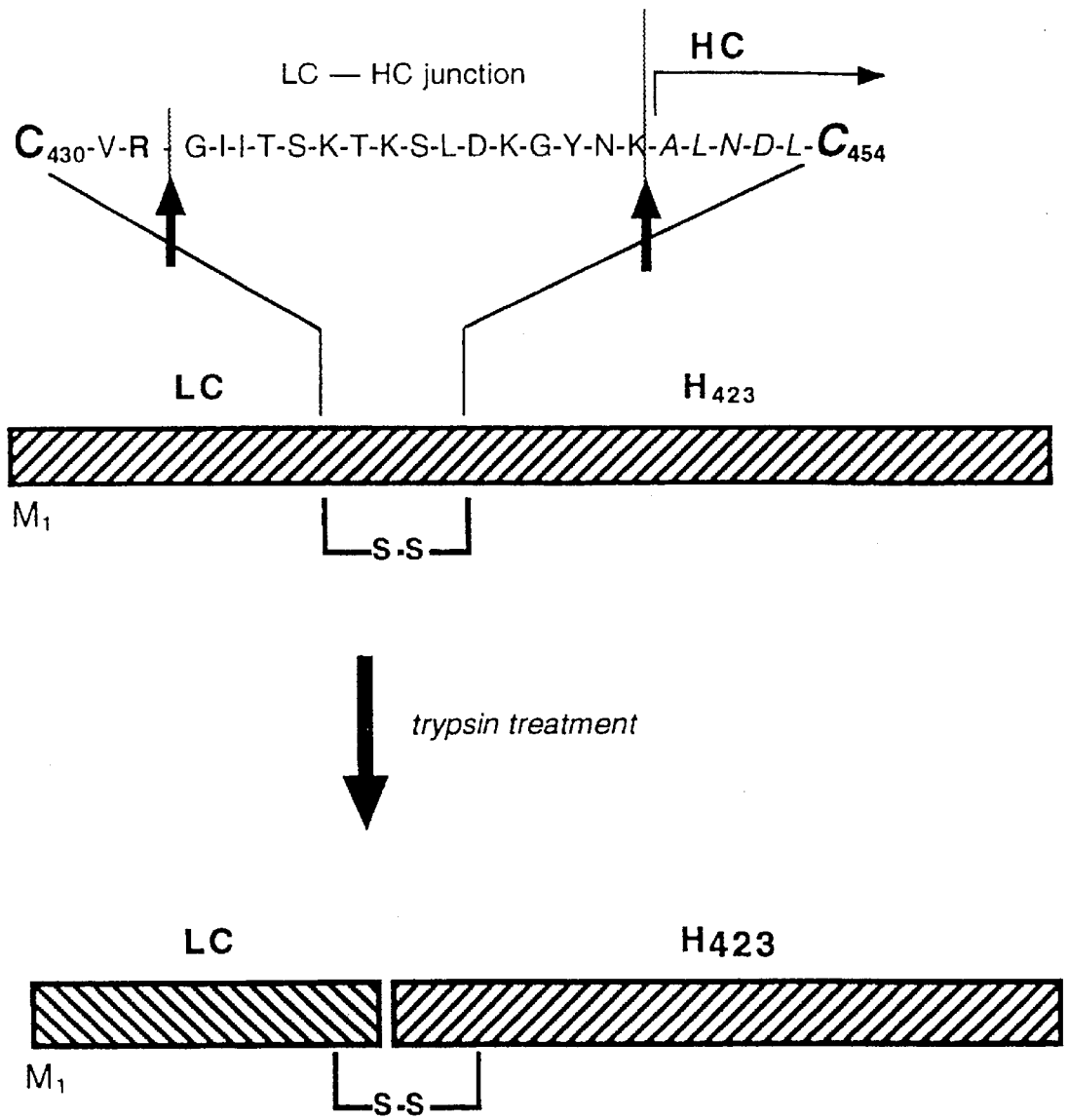

FIGS. 10 & 11 polypeptides of the invention; FIG. 10 shows $LH_{423}/A$ with N-terminal addition of an affinity purification peptide (in this case GST) and C-terminal addition of an lg binding domain; protease cleavage sites R1, R2 and R3 enable selective enzymatic separation of domains; FIG. 11 shows specific examples of protease cleavage sites R1, R2 and R3 and a C-terminal fusion peptide sequence;

FIG. 12 shows the trypsin sensitive activation region of a polypeptide of the invention;

FIG. 13 shows Western blot analysis of recombinant $LH_{107}/B$ expressed from *E.coli*; panel A was probed with anti-BoNT/B antiserum; Lane 1, molecular weight standards; lanes 2 & 3, native BoNT/B; lane 4, immunopurified $LH_{107}/B$; panel B was probed with anti-T7 peptide tag antiserum; lane 1, molecular weight standards; lanes 2 & 3, positive control *E.coli* T7 expression; lane 4 immunopurified $LH_{107}/B$.

The sequence listing that accompanies this application contains the following sequences:

| SEQ ID NO: | Sequence |
|---|---|
| 1 | DNA coding for $LH_{423}/A$ |
| 2 | $LH_{423}/A$ |
| 3 | DNA coding for $_{23}LH_{423}/A$ $(Q_2E,N_{26}K,A_{27}Y)$, of which an N-terminal portion is shown in FIG. 4. |
| 4 | $_{23}LH_{423}/A$ $(Q_2E,N_{26}K,A_{27}Y)$ |
| 5 | DNA coding for $_2LH_{423}/A$ $(Q_2E,N_{26}K,A_{27}Y)$, of which an N-terminal portion is shown in FIG.4 |
| 6 | $_2LH_{423}/A$ $(Q_2E,N_{26}K,A_{27}Y)$ |
| 7 | DNA coding for native BoNT/A according to Binz et al |
| 8 | native BoNT/A according to Binz et al |
| 9 | DNA coding for $L_{/4}H_{423}/A$ |
| 10 | $L_{/4}H_{423}/A$ |
| 11 | DNA coding for $L_{FXa/3}H_{423}/A$ |
| 12 | $L_{FXa/3}H_{423}/A$ |
| 13 | DNA coding for $L_{FXa/3}H_{423}/A$-IGF-1 |
| 14 | $L_{FXa/3}H_{423}/A$-IGF-1 |
| 15 | DNA coding for $L_{FXa/3}H_{423}/A$-CtxA14 |
| 16 | $L_{FXa/3}H_{423}/A$-CtxA14 |
| 17 | DNA coding for $L_{FXa/3}H_{423}/A$-ZZ |
| 18 | $L_{FXa/3}H_{423}/A$-ZZ |
| 19 | DNA coding for $LH_{728}/B$ |
| 20 | $LH_{728}/B$ |
| 21 | DNA coding for $LH_{417}/B$ |
| 22 | $LH_{417}/B$ |
| 23 | DNA coding for $LH_{107}/B$ |
| 24 | $LH_{107}/B$ |
| 25 | DNA coding for $LH_{423}/A$ $(Q_2E,N_{26}K,A_{27}Y)$ |
| 26 | $LH_{423}/A$ $(Q_2E,N_{26}K,A_{27}Y)$ |
| 27 | DNA coding for $LH_{417}/B$ wherein the first 274 bases are modified to have an *E. coli* codon bias |
| 28 | DNA coding for $LH_{417}/B$ wherein bases 691–1641 of the native BoNT/B sequence have been replaced by a degenerate DNA coding for amino acid residues 231–547 of the native BoNT/B polypeptide |

EXAMPLES

Example 1

Figure 1:
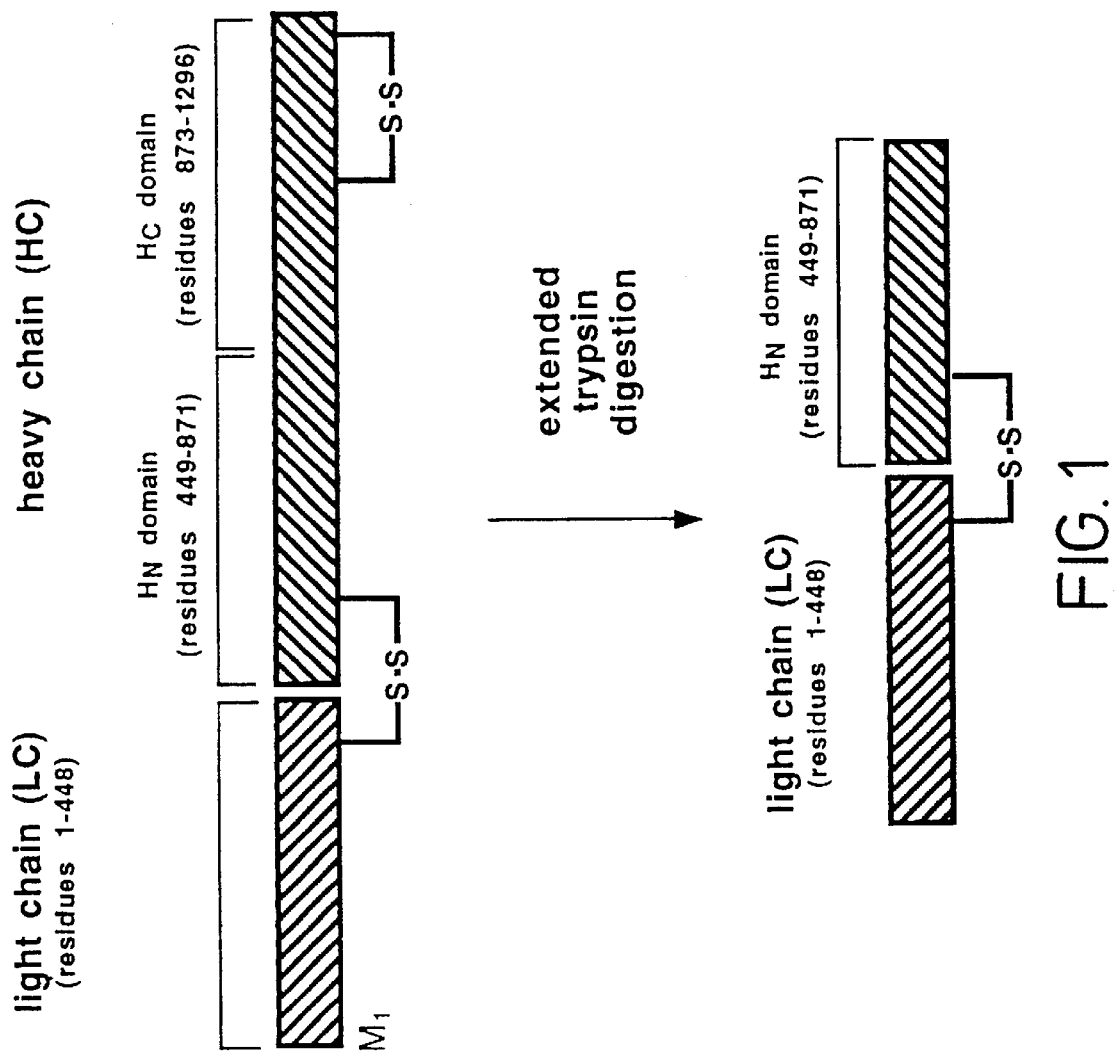
FIG. 1 shows a schematic representation of the domain structure of botulinum neurotoxin type A (BoNT/A)
Figure 2:
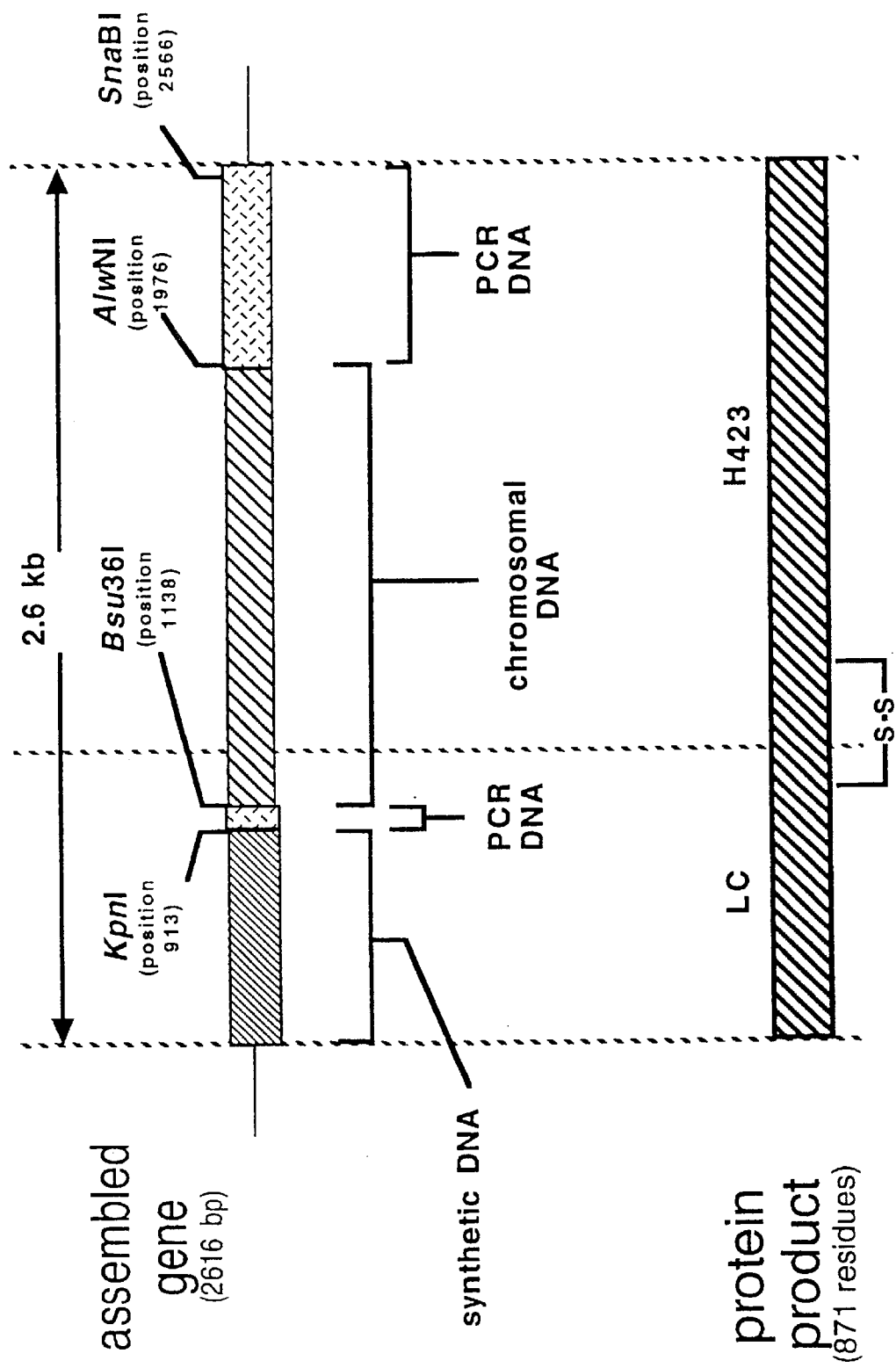
FIG. 2 shows a schematic representation of assembly of the gene for an embodiment of the invention designated $LH_{423}/A$.

A 2616 base pair, double stranded gene sequence (SEQ ID NO: 1) has been assembled from a combination of synthetic, chromosomal and polymerase-chain-reaction generated DNA (FIG. 2). The gene codes for a polypeptide of 871 amino acid residues corresponding to the entire light-chain (LC, 448 amino acids) and 423 residues of the amino terminus of the heavy-chain (Hc) of botulinum neurotoxin type A. This recombinant product is designated the $LH_{423}/A$ fragment (SEQ ID NO: 2).

Construction of the Recombinant Product

The first 918 base pairs of the recombinant gene were synthesised by concatenation of short oligonucleotides to generate a coding sequence with an *E. coli* codon bias. Both DNA strands in this region were completely synthesised as short overlapping oligonucleotides which were phosphorylated, annealed and ligated to generate the full synthetic region ending with a unique KpnI restriction site. The remainder of the $LH_{423}/A$ coding sequence was PCR amplified from total chromosomal DNA from *Clostridium botulinum* and annealed to the synthetic portion of the gene.

The internal PCR amplified product sequences were then deleted and replaced with the native, fully sequenced, regions from clones of *C. botulinum* chromosomal origin to generate the final gene construct. The final composition is synthetic DNA (bases 1–913), polymerase amplified DNA (bases 914–1138 and 1976–2616) and the remainder is of *C. botulinum* chromosomal origin (bases 1139–1975). The assembled gene was then fully sequenced and cloned into a variety of *E.coli* plasmid vectors for expression analysis.

Expression of the Recombinant Gene and Recovery of Protein Product

The DNA is expressed in *E. coli* as a single nucleic acid transcript producing a soluble single chain polypeptide of 99,951 Daltons predicted molecular weight. The gene is currently expressed in *E. coli* as a fusion to the commercially available coding sequence of glutathione S-transferase (GST) of *Schistosoma japonicum* but any of an extensive range of recombinant gene expression vectors such as pEZZ18, pTrc99, pFLAG or the pMAL series may be equally effective as might expression in other prokaryotic or eukaryotic hosts such as the Gram positive bacilli, the yeast *P. pastoris* or in insect or mammalian cells under appropriate conditions.

Currently, *E. coli* harbouring the expression construct is grown in Luria-Bertani broth (L-broth pH 7.0, containing 10 g/l bacto-tryptone, 5 g/l bacto-yeast extract and 10 g/l sodium chloride) at 37° C. until the cell density (biomass) has an optical absorbance of 0.4–0.6 at 600 nm and the cells are in mid-logarithmic growth phase. Expression of the gene is then induced by addition of isopropylthio-β-D-galactosidase (IPTG) to a final concentration of 0.5 mM. Recombinant gene expression is allowed to proceed for 90 min at a reduced temperature of 25° C. The cells are then harvested by centrifugation, are resuspended in a buffer solution containing 10 mM $Na_2HPO_4$, 0.5 M NaCl, 10 mM EGTA, 0.25% Tween, pH 7.0 and then frozen at −20° C. For extraction of the recombinant protein the cells are disrupted by sonication. The cell extract is then cleared of debris by centrifugation and the cleared supernatant fluid containing soluble recombinant fusion protein (GST-$LH_{423}/A$) is stored at −20° C. pending purification. A proportion of recombinant material is not released by the sonication procedure and this probably reflects insolubility or inclusion body formation. Currently we do not extract this material for analysis but if desired this could be readily achieved using methods known to those skilled in the art.

The recombinant GST-$LH_{423}/A$ is purified by adsorption onto a commercially prepared affinity matrix of glutathione Sepharose and subsequent elution with reduced glutathione. The GST affinity purification marker is then removed by proteolytic cleavage and reabsorption to glutathione Sepharose; recombinant $LH_{423}/A$ is recovered in the non-adsorbed material.

Construct Variants

A variant of the molecule, $LH_{423}/A$ $(Q_2E,N_{26}K,A_{27}Y)$ (SEQ ID NO: 26) has been produced in which three amino acid residues have been modified within the light chain of $LH_{423}/A$ producing a polypeptide containing a light chain sequence different to that of the published amino acid sequence of the light chain of BoNT/A.

Two further variants of the gene sequence that have been expressed and the corresponding products purified are $_{23}LH_{423}/A$ $(Q_2E,N_{26}K,A_{27}Y)$ (SEQ ID NO: 4) which has a 23 amino acid N-terminal extension as compared to the predicted native L-chain of BoNT/A and $_2$LH$_{423}$/A (Q$_2$E, N$_{26}$K,A$_{27}$Y) (SEQ ID NO: 6) which has a 2 amino acid N-terminal extension (FIG. 4).

In yet another variant a gene has been produced which contains a Eco 47 III restriction site between nucleotides 1344 and 1 345 of the gene sequence given in (SEQ ID NO: 1). This modification provides a restriction site at the position in the gene representing the interface of the heavy and light chains in native neurotoxin, and provides the capability to make insertions at this point using standard restriction enzyme methodologies known to those skilled in the art. It will also be obvious to those skilled in the art that any one of a number of restriction sites could be so employed, and that the Eco 47 III insertion simply exemplifies this approach. Similarly, it would be obvious for one skilled in the art that insertion of a restriction site in the manner described could be performed on any gene of the invention. The gene described, when expressed, codes for a polypeptide, L$_{/4}$H$_{423}$1A (SEQ ID NO: 10), which contains an additional four amino acids between amino acids 448 and 449 of LH$_{423}$/A at a position equivalent to the amino terminus of the heavy chain of native BoNT/A.

A variant of the gene has been expressed, L$_{FXa/3}$H$_{423}$/A (SEQ ID NO: 12), in which a specific proteolytic cleavage site was incorporated at the carboxy-terminal end of the light chain domain, specifically after residue 448 of L$_{/4}$H$_{423}$/A. The cleavage site incorporated was for Factor Xa protease and was coded for by modification of SEQ ID NO: 1. It will be apparent to one skilled in the art that a cleavage site for another specified protease could be similarly incorporated, and that any gene sequence coding for the required cleavage site could be employed. Modification of the gene sequence in this manner to code for a defined protease site could be performed on any gene of the invention.

Variants of L$_{FXa/3}$H$_{423}$/A have been constructed in which a third domain is present at the carboxy-terminal end of the polypeptide which incorporates a specific binding activity into the polypeptide.

Specific examples described are:
(1) L$_{FXa/3}$H$_{423}$/A-IGF-1 (SEQ ID NO: 14), in which the carboxy-terminal domain has a sequence equivalent to that of insulin-like growth factor-1 (IGF-1) and is able to bind to the insulin-like growth factor receptor with high affinity;
(2) L$_{FXa/3}$H$_{423}$/A-CtxA14 (SEQ ID NO: 16), in which the carboxy-terminal domain has a sequence equivalent to that of the 14 amino acids from the carboxy-terminus of the A-subunit of cholera toxin (CtxA) and is thereby able to interact with the cholera toxin B-subunit pentamer; and
(3) L$_{FXa/3}$H$_{423}$/A-ZZ (SEQ ID NO: 18), in which the carboxy-terminal domain is a tandem repeating synthetic IgG binding domain. This variant also exemplifies another modification applicable to the current invention, namely the inclusion in the gene of a sequence coding for a protease cleavage site located between the end of the clostridial heavy chain sequence and the sequence coding for the binding ligand. Specifically in this example a sequence is inserted at nucleotides 2650 to 2666 coding for a genenase cleavage site. Expression of this gene produces a polypeptide which has the desired protease sensitivity at the interface between the domain providing H$_N$ function and the binding domain. Such a modification enables selective removal of the C-terminal binding domain by treatment of the polypeptide with the relevant protease.

It will be apparent that any one of a number of such binding domains could be incorporated into the polypeptide sequences of this invention and that the above examples are merely to exemplify the concept. Similarly, such binding domains can be incorporated into any of the polypeptide sequences that are the basis of this invention. Further, it should be noted that such binding domains could be incorporated at any appropriate location within the polypeptide molecules of the invention.

Further embodiments of the invention are thus illustrated by a DNA of the invention further comprising a desired restriction endonuclease site at a desired location and by a polypeptide of the invention further comprising a desired protease cleavage site at a desired location.

The restriction endonuclease site may be introduced so as to facilitate further manipulation of the DNA in manufacture of an expression vector for expressing a polypeptide of the invention; it may be introduced as a consequence of a previous step in manufacture of the DNA; it may be introduced by way of modification by insertion, substitution or deletion of a known sequence. The consequence of modification of the DNA may be that the amino acid sequence is unchanged, or may be that the amino acid sequence is changed, for example resulting in introduction of a desired protease cleavage site, either way the polypeptide retains its first and second domains having the properties required by the invention.

FIG. 10 is a diagrammatic representation of an expression product exemplifying features described in this example. Specifically, it illustrates a single polypeptide incorporating a domain equivalent to the light chain of botulinum neurotoxin type A and a domain equivalent to the H$_N$ domain of the heavy chain of botulinum neurotoxin type A with a N-terminal extension providing an affinity purification domain, namely GST, and a C-terminal extension providing a ligand binding domain, namely an igG binding domain. The domains of the polypeptide are spatially separated by specific protease cleavage sites enabling selective enzymatic separation of domains as exemplified in the Figure. This concept is more specifically depicted in FIG. 11 where the various protease sensitivities are defined for the purpose of example.

Assay of Product Activity

Figure 3:
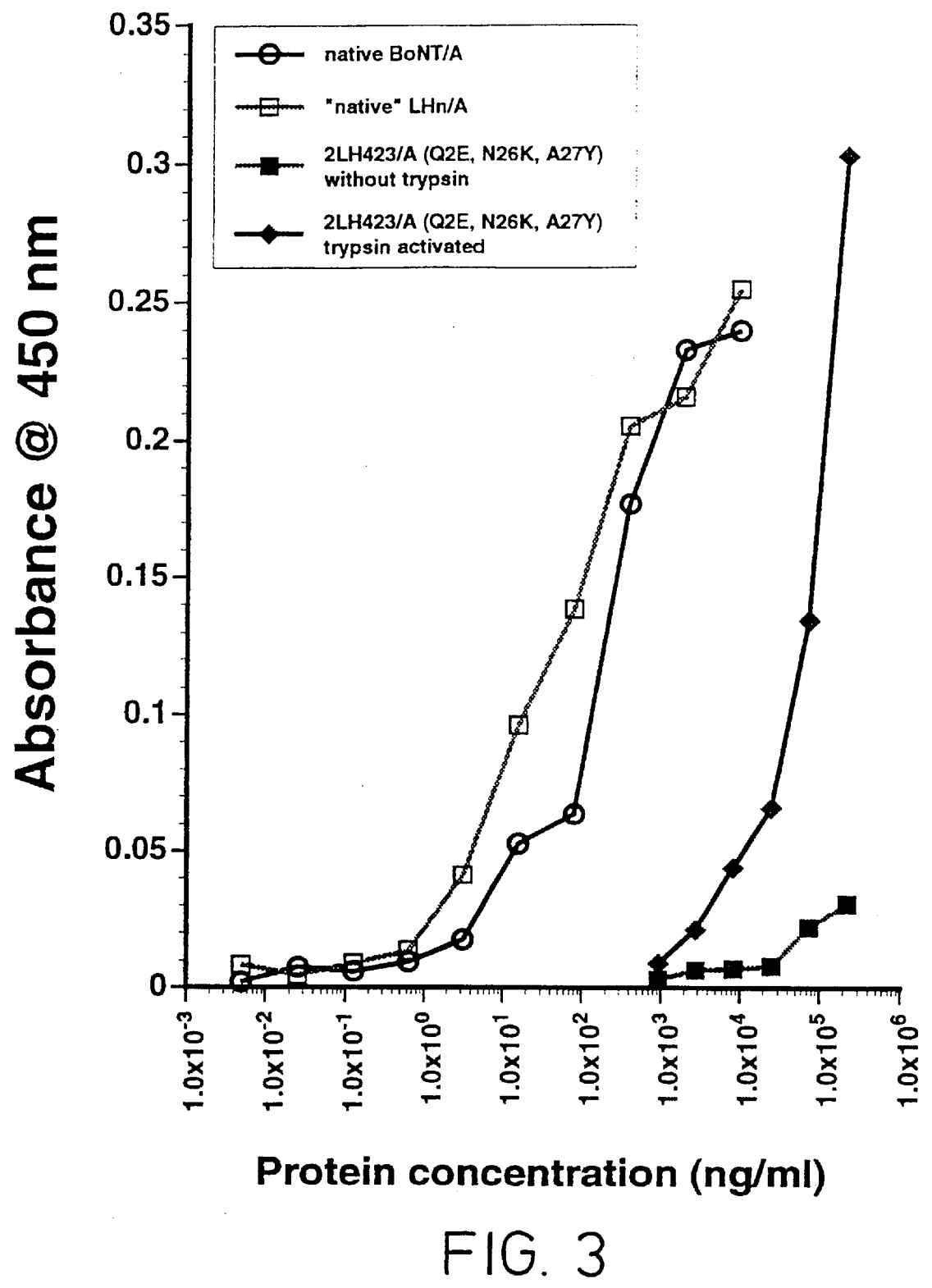

The LC of botulinum neurotoxin type A exerts a zinc-dependent endopeptidase activity on the synaptic vesicle associated protein SNAP-25 which it cleaves in a specific manner at a single peptide bond. The $_2$LH$_{423}$/A (Q$_2$E,N$_{26}$K, A$_{27}$Y) (SEQ ID NO: 6) cleaves a synthetic SNAP-25 substrate in vitro under the same conditions as the native toxin (FIG. 3). Thus, the modification of the polypeptide sequence of $_2$LH$_{423}$/A (Q$_2$E,N$_{26}$K,A$_{27}$Y) relative to the native sequence and within the minimal functional LC domains does not prevent the functional activity of the LC domains.

This activity is dependent on proteolytic modification of the recombinant GST-$_2$LH$_{423}$/A (Q$_2$E,N$_{26}$K,A$_{27}$Y) to convert the single chain polypeptide product to a disulphide linked dichain species. This is currently done using the proteolytic enzyme trypsin. The recombinant product (100–600 μg/ml) is incubated at 37° C. for 10–50 minutes with trypsin (10 μg/ml) in a solution containing 140 mM NaCl, 2.7 mM KCl, 10 mM Na$_2$HPO$_4$, 1.8 mM KH$_2$PO$_4$, pH 7.3. The reaction is terminated by addition of a 100-fold molar excess of trypsin inhibitor. The activation by trypsin generates a disulphide linked dichain species as determined by polyacrylamide gel electrophoresis and immunoblotting analysis using polyclonal anti-botulinum neurotoxin type A antiserum.

$_2$LH$_{423}$/A is more stable in the presence of trypsin and more active in the in vitro peptide cleavage assay than is $_{23}LH_{423}/A$. Both variants, however, are fully functional in the in vitro peptide cleavage assay. This demonstrates that the recombinant molecule will tolerate N-terminal amino acid extensions and this may be expanded to other chemical or organic moieties as would be obvious to those skilled in the art.

Example 2

As a further exemplification of this invention a number of gene sequences have been assembled coding for polypeptides corresponding to the entire light-chain and varying numbers of residues from the amino terminal end of the heavy chain of botulinum neurotoxin type B. In this exemplification of the disclosure the gene sequences assembled were obtained from a combination of chromosomal and polymerase-chain-reaction generated DNA, and therefore have the nucleotide sequence of the equivalent regions of the natural genes, thus exemplifying the principle that the substance of this disclosure can be based upon natural as well as a synthetic gene sequences.

The gene sequences relating to this example were all assembled and expressed using methodologies as detailed in Sambrook J, Fritsch E F & Maniatis T (1989) Molecular Cloning: A Laboratory Manual (2nd Edition), Ford N, Nolan C, Ferguson M & Ockler M (eds), Cold Spring Harbor Laboratory Press, New York, and known to those skilled in the art.

A gene has been assembled coding for a polypeptide of 1171 amino acids corresponding to the entire light-chain (443 amino acids) and 728 residues from the amino terminus of the heavy chain of neurotoxin type B. Expression of this gene produces a polypeptide, $LH_{728}/B$ (SEQ ID NO: 20), which lacks the specific neuronal binding activity of full length BoNT/B.

A gene has also been assembled coding for a variant polypeptide, $LH_{417}/B$ (SEQ ID NO: 22), which possesses an amino acid sequence at its carboxy terminus equivalent by amino acid homology to that at the carboxy-terminus of the heavy chain fragment in native $LH_N/A$.

A gene has also been assembled coding for a variant polypeptide, $LH_{107}/B$ (SEQ ID NO: 24), which expresses at its carboxy-terminus a short sequence from the amino terminus of the heavy chain of BoNT/B sufficient to maintain solubility of the expressed polypeptide.

Construct Variants

A variant of the coding sequence for the first 274 bases of the gene shown in SEQ ID NO: 21 has been produced which whilst being a non-native nucleotide sequence still codes for the native polypeptide.

Two double stranded, a 268 base pair and a 951 base pair, gene sequences have been created using an overlapping primer PCR strategy. The nucleotide bias of these sequences was designed to have an E.coli codon usage bias.

For the first sequence, six oligonucleotides representing the first (5') 268 nucleotides of the native sequence for botulinum toxin type B were synthesised. For the second sequence 23 oligonucleotides representing internal sequence nucleotides 691–1641 of the native sequence for botulinum toxin type B were synthesised. The oligonucleotides ranged from 57–73 nucleotides in length. Overlapping regions, 17–20 nucleotides, were designed to give melting temperatures in the range 52–56° C. In addition, terminal restriction endonuclease sites of the synthetic products were constructed to facilitate insertion of these products into the exact corresponding region of the native sequence. The 268 bp 5' synthetic sequence has been incorporated into the gene shown in SEQ ID NO: 21 in place of the original first 268 bases (and is shown in SEQ ID NO: 27). Similarly the sequence could be inserted into other genes of the examples.

Another variant sequence equivalent to nucleotides 691 to 1641 of SEQ ID NO: 21 and employing non-native codon usage whilst coding for a native polypeptide sequence, has been constructed using the internal synthetic sequence. This sequence (SEQ ID NO: 28) can be incorporated, alone or in combination with other variant sequences, in place of the equivalent coding sequence in any of the genes of the example.

Example 3

An exemplification of the utility of this invention is as a non-toxic and effective immunogen. The non-toxic nature of the recombinant, single chain material was demonstrated by intraperitoneal administration in mice of $GST-_2LH_{423}/A$. The polypeptide was prepared and purified as described above. The amount of immunoreactive material in the final preparation was determined by enzyme linked immunosorbent assay (ELISA) using a monoclonal antibody (BA11) reactive against a conformation dependent epitope on the native $LH_N/A$. The recombinant material was serially diluted in phosphate buffered saline (PBS; NaCl 8 g/l, KCl 0.2 g/l, $Na_2HPO_4$ 1.15 g/l, $KH_2PO_4$ 0.2 g/l, pH 7.4) and 0.5 ml volumes injected into 3 groups of 4 mice such that each group of mice received 10, 5 and 1 micrograms of material respectively. Mice were observed for 4 days and no deaths were seen.

For immunisation, 20 µg of $GST-_2LH_{423}/A$ in a 1.0 ml volume of water-in-oil emulsion (1:1 vol:vol) using Freund's complete (primary injections only) or Freund's incomplete adjuvant was administered into guinea pigs via two sub-cutaneous dorsal injections. Three injections at 10 day intervals were given (day 1, day 10 and day 20) and antiserum collected on day 30. The antisera were shown by ELISA to be immunoreactive against native botulinum neurotoxin type A and to its derivative $LH_N/A$. Antisera which were botulinum neurotoxin reactive at a dilution of 1:2000 were used for evaluation of neutralising efficacy in mice. For neutralisation assays 0.1 ml of antiserum was diluted into 2.5 ml of gelatine phosphate buffer (GPB; $Na_2HPO_4$ anhydrous 10 g/l, gelatin (Difco) 2 g/l, pH 6.5–6.6) containing a dilution range from 0.5 µg ($5 \times 10^{-6}$ g) to 5 picograms ($5 \times 10^{-12}$ g). Aliquots of 0.5 ml were injected into mice intraperitoneally and deaths recorded over a 4 day period. The results are shown in Table 1 and Table 2. It can clearly be seen that 0.5 ml of 1:40 diluted anti-$GST-_2LH_{423}/A$ antiserum can protect mice against intraperitoneal challenge with botulinum neurotoxin in the range 5 pg-50 ng (1–10, 000 mouse LD50; 1 mouse LD50=5 pg).

TABLE 1

Neutralisation of botulinum neurotoxin in mice by guinea pig anti-$GST-_2LH_{423}/A$ antiserum.

| Survivors On Day | Botulinum Toxin/mouse | | | | | | Control (no toxin) |
|---|---|---|---|---|---|---|---|
|  | 0.5 µg | 0.005 µg | 0.0005 µg | 0.5 ng | 0.005 ng | 5 pg |  |
| 1 | 0 | 4 | 4 | 4 | 4 | 4 | 4 |
| 2 | — | 4 | 4 | 4 | 4 | 4 | 4 |
| 3 | — | 4 | 4 | 4 | 4 | 4 | 4 |
| 4 | — | 4 | 4 | 4 | 4 | 4 | 4 |

TABLE 2

Neutralisation of botulinum neurotoxin
in mice by non-immune guinea pig antiserum.

| Survivors On Day | Botulinum Toxin/mouse | | | | | | Control (no toxin) |
|---|---|---|---|---|---|---|---|
| | 0.5 μg | 0.005 μg | 0.0005 μg | 0.5 ng | 0.005 ng | 5 pg | |
| 1 | 0 | 0 | 0 | 0 | 0 | 2 | 4 |
| 2 | — | — | — | — | — | 0 | 4 |
| 3 | — | — | — | — | — | — | 4 |
| 4 | — | — | — | — | — | — | 4 |

Example 4
Expression of Recombinant $LH_{107}$/B in *E. coli*.

As an exemplification of the expression of a nucleic acid coding for a $LH_N$ of a clostridial neurotoxin of a serotype other than botulinum neurotoxin type A, the nucleic acid sequence (SEQ ID NO: 23) coding for the polypeptide $LH_{107}$/B (SEQ ID NO: 24) was inserted into the commercially available plasmid pET28a (Novogen, Madison, Wis., USA). The nucleic acid was expressed in *E. coli* BL21 (DE3) (New England BioLabs, Beverley, Mass., USA) as a fusion protein with a N-terminal T7 fusion peptide, under IPTG induction at 1 mM for 90 minutes at 37° C. Cultures were harvested and recombinant protein extracted as described previously for $LH_{423}$/A.

Recombinant protein was recovered and purified from bacterial paste lysates by immunoaffinity adsorption to an immobilised anti-T7 peptide monoclonal antibody using a T7 tag purification kit (New England bioLabs, Beverley, Mass., USA). Purified recombinant protein was analysed by gradient (4–20%) denaturing SDS-polyacrylamide get electrophoresis (Novex, San Diego, Calif., USA) and western blotting using polyclonal anti-botulinum neurotoxin type B antiserum or anti-T7 antiserum. Western blotting reagents were from Novex, immunostained proteins were visualised using the Enhanced Chemi-Luminescence system (ECL) from Amersham. The expression of an anti-T7 antibody and anti-botulinum neurotoxin type B antiserum reactive recombinant product is demonstrated in FIG. 13.

The recombinant product was soluble and retained that part of the light chain responsible for endopeptidase activity.

The invention thus provides recombinant polypeptides useful inter alia as immunogens, enzyme standards and components for synthesis of molecules as described in WO-A-94/21300.

What is claimed is:

1. A non-toxic polypeptide comprising first, second and third domains, wherein
   (a) said first domain comprises a botulinum toxin light chain and cleaves one or more vesicle or plasma-membrane associated proteins essential to exocytosis,
   (b) said second domain comprises the first 100 N-terminal amino acids of a botulinum toxin heavy chain and (i) translocates the polypeptide into a cell or (ii) increases the solubility of the polypeptide compared to the solubility of the first domain on its own or (iii) both translocates the polypeptide into a cell and increases the solubility of the polypeptide compared to the solubility of the first domain on its own,
   (c) said polypeptide is free of clostridial neurotoxin and free of clostridial neurotoxin precursor that can be converted into toxin by proteolytic action,
   (d) said polypeptide is a single polypeptide,
   (e) said third domain is a tandem repeat synthetic IgG binding domain derived from domain β of Staphylococcal protein A, and
   (f) said polypeptide lacks a portion designated $H_c$ of a botulinum toxin heavy chain.

2. A non-toxin polypeptide comprising first, second and third domains, wherein
   (a) said first domain comprises a botulinum toxin light chain and cleaves one or more vesicle or plasma-membrane associated proteins essential to exocytosis,
   (b) said second domain comprises the first 100 N-terminal amino acids of a botulinum toxin heavy chains and (i) translocates the polypeptide into a cell of (ii) increases the solubility of the polypeptide compared to the solubility of the first domain on its own or (iii) both translocates the polypeptide into a cell and increases the solubility of the polypeptide compared to the solubility of the first domain on its own,
   (c) said polypeptide is free of clostridial neurotoxin and free of clostridial neurotoxin precursor that can be converted into toxin by proteolytic action,
   (d) said polypeptide is a single polypeptide,
   (e) said third domain is insulin-like growth-factor-1 (IGF-1), and
   (f) said polypeptide lacks a portion designated $H_c$ of a botulinum toxin heavy chain.

3. A non-toxin polypeptide comprising first and second domains, wherein
   (a) said first domain is a botulinum toxin type A light chain variant comprising a sequence correspond to amino acids 1–448 of SEQ ID NO:2 wherein three amino acid residues have been altered compared to that sequence, namely at residue 2 a glutamate, at residue 26 a lysine and at residue 27 a tyrosine which first domain cleaves one or more vesicle or plasma-membrane associated proteins essential to exocytosis,
   (b) said second domain comprises the first 100 N-terminal amino acids of a botulinum toxin heavy chains and (i) translocates the polypeptide into a cell of (ii) increases the solubility of the polypeptide compared to the solubility of the first domain on its own or (iii) both translocates the polypeptide into a cell and increases the solubility of the polypeptide compared to the solubility of the first domain on its own,
   (c) said polypeptide is free of clostridial neurotoxin and free of clostridial neurotoxin precursor that can be converted into toxin by proteolytic action,
   (d) said polypeptide is a single polypeptide,
   (e) one or both of (i) the toxin light chain or fragment or variant of toxin light chain and (ii) the portion of the toxin heavy chain are of botulinum toxin type A, and
   (f) said polypeptide lacks a portion designated $H_c$ of a botulinum toxin heavy chain.

4. A non-toxin polypeptide comprising first and second domains, wherein
   (a) first domain comprises a botulinum toxin light chain and cleaves one or more vesicle or plasma-membrane associated proteins essential to exocytosis,
   (b) said second domain comprises the first 100 N-terminal amino acids of a botulinum toxin heavy chain and (i) translocates the polypeptide into a cell or (ii) increases the solubility of the polypeptide compared to the solubility of the first domain on its own or (iii) both translocates the polypeptide into a cell and increases the solubility of the polypeptide compared to the solubility of the first domain on its own, (c) said polypeptide is free of clostridial neurotoxin and free of clostridial neurotoxin precursor that can be converted into toxin by proteolytic action, (d) said polypeptide is a single polypeptide, and (e) said polypeptide lacks a portion designated $H_c$ of a botulinum toxin heavy chain.

5. A non-toxin polypeptide comprising first and second domains, wherein (a) said first domain comprises a botulinum toxin light chain and cleaves one or more vesicle or plasma-membrane associated proteins essential to exocytosis, (b) said second domain comprises the first 100 N-terminal amino acids of a botulinum toxin heavy chain and (i) translocates the polypeptide into a cell or (ii) increases the solubility of the polypeptide compared to the solubility of the first domain on its own or (iii) both translocates the polypeptide into a cell and increases the solubility of the polypeptide compared to the solubility of the first domain on its own, (c) said polypeptide is free of clostridial neurotoxin and free of clostridial neurotoxin precursor that can be converted into toxin by proteolytic action, (d) said polypeptide is a single polypeptide, (e) said second domain comprises a portion designated $H_N$ of the botulinum toxin heavy chain which consists of the 423 N-terminal amino acids of a botulinum toxin type A heavy chain, and (f) said polypeptide lacks a portion designated $H_c$ of a botulinum toxin heavy chain.

6. A polypeptide according to claim 5 wherein the first domain comprises a botulinum toxin type A light chain.

7. A polypeptide according to claim 5 wherein said first domain is a botulinum toxin type A light chain variant which comprises a sequence corresponding to amino acids 1–448 of SEQ ID NO:2 having at least three amino acid residues which are altered compared to that sequence, namely at residue 2 a glutamate, residue 26 a lysine and residue 27 a tyrosine, and wherein said polypeptide contains 423 N-terminal amino acids of a botulinum toxin type A heavy chain.

8. A polypeptide comprising a botulinum toxin light chain and a botulinum toxin heavy chain lacking a C-terminal part of the botulinum toxin heavy chain designated $H_c$ wherein said botulinum toxin heavy chain is not capable of binding to cell surface receptors.

9. A polypeptide according to claim 8 wherein said heavy chain lacks amino acid residues 872 –1296 of botulinum toxin A.

10. A polypeptide having an amino acid sequence selected from the group consisting of SEQ ID NO. 2, 4, 6, 10, 12, 14, 16, 18, 20, 22, 24, and 26.

* * * * *

UNITED STATES PATENT AND TRADEMARK OFFICE
CERTIFICATE OF CORRECTION

PATENT NO. : 6,461,617 B1
DATED : October 8, 2002
INVENTOR(S) : Shone et al.

It is certified that error appears in the above-identified patent and that said Letters Patent is hereby corrected as shown below:

Column 1,
Line 28, please delete "clostridiai" and insert therein -- clostridial --.
Line 41, please delete "iow" and insert therein -- low --.

Column 4,
Line 65, please delete "potypeptide" and insert therein -- polypeptide --.

Column 7,
Line 3, please delete "poiypeptides" and insert therein -- polypeptides --.

Column 14,
Line 4, please delete "equivalentto" and insert therein -- equivalent to --.

Column 167,
Line 51, please delete "non-toxin" and insert therein -- non-toxic --.
Line 57, please delete "chains" and insert therein -- chain --.
Line 58, please delete "of" and insert therein -- or --.

Column 168,
Lines 31 and 58, please delete "non-toxin" and insert therein -- non-toxic --.
Line 34, please delete "correspond" and insert therein -- corresponding --.
Line 42, please delete "chains" and insert therein -- chain --.
Line 43, please delete "of" and insert therein -- or --.
Line 60, please delete "(a) first" and insert therein -- (a) said first --.

Column 169,
Line 10, please delete "non-toxin" and insert therein -- non-toxic --.
Line 29, please delete "of the botulinum" and insert therein -- of a botulinum --.

Signed and Sealed this

Twelfth Day of August, 2003

JAMES E. ROGAN
*Director of the United States Patent and Trademark Office*